(12) United States Patent
Hresko et al.

(10) Patent No.: US 7,339,044 B2
(45) Date of Patent: Mar. 4, 2008

(54) NEMATODE PAN AND ZP RECEPTOR-LIKE SEQUENCES

(75) Inventors: Michelle Coutu Hresko, Chesterfield, MO (US); Merry B. McLaird, Kirkwood, MO (US); Deryck J. Williams, University City, MO (US); Anita M. Frevert, St. Louis, MO (US); Brandi Chiapelli, St. Louis, MO (US); Catherine Baublite, St. Louis, MO (US); Andrew P. Kloek, San Francisco, CA (US); Jennifer A. Davila-Aponte, St. Louis, MO (US); John D. Bradley, St. Louis, MO (US); Siqun Xu, Ballwin, MO (US)

(73) Assignee: Divergence, Inc., St. Louis, MO (US)

( * ) Notice: Subject to any disclaimer, the term of this patent is extended or adjusted under 35 U.S.C. 154(b) by 0 days.

(21) Appl. No.: 11/191,588

(22) Filed: Jul. 28, 2005

(65) Prior Publication Data
US 2005/0282222 A1    Dec. 22, 2005

Related U.S. Application Data

(62) Division of application No. 10/771,708, filed on Feb. 4, 2004, now Pat. No. 6,936,693.

(60) Provisional application No. 60/444,771, filed on Feb. 4, 2003.

(51) Int. Cl.
*C07H 21/04* (2006.01)
*C07K 14/00* (2006.01)

(52) U.S. Cl. ..................... 536/23.1; 530/350
(58) Field of Classification Search ............... 530/350; 435/69.1, 7.1; 514/12; 536/23.1
See application file for complete search history.

(56) References Cited

OTHER PUBLICATIONS

GenBank Accession No. AA471404 (gi:2199168); Blaxter et al., Jun. 17, 1997.
GenBank Accession No. BI500192 (gi:15339536); McCarter et al., Aug. 28, 2001.
GenBank Accession No. BE579677 (gi:9830619); McCarter et al., May 9, 2001.
GenBank Accession No. BI782938 (gi:15785830); McCarter et al., Sep. 26, 2001.
GenBank Accession No. BI744615 (gi:15766417); McCarter et al., Sep. 25, 2001.
GenBank Accession No. BI073876 (gi:14494496); McCarter et al., Jun. 19, 2001.
GenBank Accession No. BM952243 (gi:19435833); McCarter et al., Mar. 14, 2002.
GenBank Accession No. BE580180 (gi:9831122); McCarter et al., May 9, 2001.
GenBank Accession No. BG893830 (gi:14288440); McCarter et al., Jun. 4, 2001.
GenBank Accession No. BF060055 (gi:10818965); Blaxter et al., Oct. 16, 2000.
GenBank Accession No. NP_491706 (gi:17505859); Genome Sequencing Consortium, Dec. 3, 2001.
GenBank Accession No. BI142440 (gi:14624150); Williams et al., Jul. 5, 2001.
GenBank Accession No. NP_502699 (gi:17540572); Nov. 22, 2002.
GenBank Accession No. AA661399 (gi:2605443); Blaxter et al., Nov. 10, 1997.
GenBank Accession No. BE579237 (gi:9830179); McCarter et al., May 9, 2001.
GenBank Accession No. BE580410 (gi:9831352); McCarter et al., May 9, 2001.

*Primary Examiner*—Robert B. Mondesi
(74) *Attorney, Agent, or Firm*—Fish & Richardson P.C.

(57) ABSTRACT

Nucleic acid molecules from nematodes encoding PAN and ZP domain containing receptor polypeptides are described. PANZP polypeptide sequences are also provided, as are vectors, host cells, and recombinant methods for production of PANZP nucleotides and polypeptides. Also described are screening methods for identifying inhibitors and/or activators, as well as methods for antibody production.

7 Claims, 16 Drawing Sheets

```
1
cgactggagcacgaggacactgacatggactgaaggagtagaaaggtttaaaaaacccagtttgagaa ATG TCT AAG TCT GGG CTT CAT CTT
                                                                     M   S   K   S   G   L   H   L
93
GTA GCC TAC ATA TTA TTG ATA TTT TTA ATT TCA ACT AAT ATA GCA TCT AAA ATT TCT GGT GTT CCA TTA TGC AAC
 V   A   Y   I   L   L   I   F   L   I   S   T   N   I   A   S   K   I   S   G   V   P   L   C   N
168
AAA GAT ACT TCA CCA GTA TTT ACA CTT CAA CAT AAT TCT ACT AAT GGT ATT TTA GCT AGA TCT CTT CCA CAA CCA
 K   D   T   S   P   V   F   T   L   Q   H   N   S   T   N   G   I   L   A   R   S   L   P   Q   P
243
GGA TTA ATT GAT TGT TCA GAA CAT TGT TCC TCT TCG TCA GAT TGT ATT GGC GTT GAA TAT TGG CAG GGA ATT TGT
 G   L   I   D   C   S   E   H   C   S   S   S   S   D   C   I   G   V   E   Y   W   Q   G   I   C
318
AGA GTT ATT TCT CAA GAT AAA ACT TCT ATT TAT ACA CCA ACA GAT GAA ACT TCA ATA CTT TTA ACA AAA TCA TGT
 R   V   I   S   Q   D   K   T   S   I   Y   T   P   T   D   E   T   S   I   L   L   T   K   S   C
393
GTT AAA AGT GAT CGT ATA TGT TCA TCA CCA TTC CAT TTT GAT GTT TAT GAA CAA AAA ATA TTA GTT GGA TTT GCT
 V   K   S   D   R   I   C   S   S   P   F   H   F   D   V   Y   E   Q   K   I   L   V   G   F   A
468
AGA GAA GTT GTA CCA GCT GAG TCT ATT GAA ATT TGT ATG GCT GCT TGT TTG AAT GCT TTT GAT ACA TAT GGT TTT
 R   E   V   V   P   A   E   S   I   E   I   C   M   A   A   C   L   N   A   F   D   T   Y   G   F
543
GAA TGT GAA TCA GCT ATG TAT TAT CCA GTT GAT AGT GAA TGT ATT CTT AAT ACT GAA GAT AGA CTT GAT CGA CCA
 E   C   E   S   A   M   Y   Y   P   V   D   S   E   C   I   L   N   T   E   D   R   L   D   R   P
618
GAT CTT TTT GTT GTT GAA AAA GAA GAT GTT GTT TAT TAT CTT GAT TCT AAT TGT GCT GGT TCA CAA TGT TAT GCT
 D   L   F   V   V   E   K   E   D   V   V   Y   Y   L   D   S   N   C   A   G   S   Q   C   Y   A
693
CCA TAC ATT ACA CAA TAT ATT GCT GTT GAA AAT AAA CAA ATA GAA AAT GAA TTA GAT AGA AAA TTT GAA AAT ATT
 P   Y   I   T   Q   Y   I   A   V   E   N   K   Q   I   E   N   E   L   D   R   K   F   E   N   I
768
GAT TTC CAA ACA TGT GAA GAA TTA TGT ACT GGT AGA ATT ACT GTT ACA CAA AAT GAT TTT ACT TGT AAA TCA TTT
 D   F   Q   T   C   E   E   L   C   T   G   R   I   T   V   T   Q   N   D   F   T   C   K   S   F
843
ATG TAT AAT CCT GAA ACA AAA GTT TGT TAT CTT TCT GAT GAA CGT TCA AAG CCT CTT GGA CGG GCT AAA TTA AGT
 M   Y   N   P   E   T   K   V   C   Y   L   S   D   E   R   S   K   P   L   G   R   A   K   L   S
918
GAT GCT AAT GGA TTT ACT TAT TAT GAA AAA AAA TGT TTT GCA TCT CCA AGA ACA TGC CGT CAA ACA CCA TCA TTT
 D   A   N   G   F   T   Y   Y   E   K   K   C   F   A   S   P   R   T   C   R   Q   T   P   S   F
993
AAT AGA GTA CCA CAA ATG ATT CTT GTT GGT TTT GCT GCA TTT GTT ATG GAA AAT GTA CCA TCT GTT ACT ATG TGC
 N   R   V   P   Q   M   I   L   V   G   F   A   A   F   V   M   E   N   V   P   S   V   T   M   C
1068
CTT GAT CAA TGT ACA AAT CCA CCA CCA GAG ACA GGT GAA AAA TTT GTC TGT AAA TCT GTT ATG TAC TAT TAT AAT
 L   D   Q   C   T   N   P   P   P   E   T   G   E   K   F   V   C   K   S   V   M   Y   Y   Y   N
1143
GAA CAA GAA TGT ATT CTT AAT GCT GAA ACA AGA CAT ACA AAG CCA GAT CTT TTT ATT ACA GAA GGA GAT GAA TTT
 E   Q   E   C   I   L   N   A   E   T   R   H   T   K   P   D   L   F   I   T   E   G   D   E   F
1218
CTT GTT GAT TAT TTT GAT ATT TCA TGT CAT CTT GAA CCA GAA ACA TGT CCT AAA GGA ACA TAT TTA AAA GGA ATT
 L   V   D   Y   F   D   I   S   C   H   L   E   P   E   T   C   P   K   G   T   Y   L   K   G   I
1293
AAA TCT ATC AAT TCT GCA CTT CCT GAG GGT GAA GGC TCA CTT CAT GTT ATT GAG TCT GCT GGA AAA TCA TTA GAA
 K   S   I   N   S   A   L   P   E   G   E   G   S   L   H   V   I   E   S   A   G   K   S   L   E
1368
GAA TGT ATG GAA AAA TGT AAC CAA CTT CAT CCA GAA AAA TGT AGA TCA TTT AAT TTT GAA AAA TCA TCT GGA TTA
 E   C   M   E   K   C   N   Q   L   H   P   E   K   C   R   S   F   N   F   E   K   S   S   G   L
1443
TGT AAT CTT TTA TAT CTT GAT GGA AAA AAT ACT TTA AAA CCA TTT ATT AAA AAT GGA TTT GAT CTT GTT GAT TTA
 C   N   L   L   Y   L   D   G   K   N   T   L   K   P   F   I   K   N   G   F   D   L   V   D   L
```

FIG. 1A

```
1518
CAA TGT TTA TCA ACT AAA AAA GAT TGC TCT ACA AAA AAG AAT GAT ATT AAT TTT GTT AAA TAT CTT TAC TCT CAT
 Q   C   L   S   T   K   K   D   C   S   T   K   K   N   D   I   N   F   V   K   Y   L   Y   S   H
1593
TTT GTT AAA TAT CTT TAC TCT CAA CAA CCT GGA ATT CCA ACA AAA ACA GAA AAA GTT ATT GGT ATT TCT AAA TGT
 F   V   K   Y   L   Y   S   Q   Q   P   G   I   P   T   K   T   E   K   V   I   G   I   S   K   C
1668
CTT GAT TTA TGT ACT GAT AGT GAA CGT TGT GAA GGA CTT AAT TAT AAT AGA AGA ACT GGA GAA TGT CAA TTA TTT
 L   D   L   C   T   D   S   E   R   C   E   G   L   N   Y   N   R   R   T   G   E   C   Q   L   F
1743
GAA ATT ATT GAT GGA CCT TCT AAT CTT AAA AAA TCT GAG CAT ATA GAT TTT TAT CAA AAT CTT TGT TCT ACT AAA
 E   I   I   D   G   P   S   N   L   K   K   S   E   H   I   D   F   Y   Q   N   L   C   S   T   K
1818
GAA AAT GAA GCT GGT GTT TCA TCT GCA TTA AAT GTA CCA CAA TCA TCT GTT ATT CCT ATT TCA TCA TCA CAA AAT
 E   N   E   A   G   V   S   S   A   L   N   V   P   Q   S   S   V   I   P   I   S   S   S   Q   N
1893
ATT AGT AAA AGT GAT GTT TTT GCC AAA AAA AAT CTT AAT AAA GAT GGT AAT AAT CAA GTA AAC ATT TAT GAA CCA
 I   S   K   S   D   V   F   A   K   K   N   L   N   K   D   G   N   N   Q   V   N   I   Y   E   P
1968
GAA AAA AAA TAC CAT CCA AAA GGA TCA AAA AAT GAA ACA TCA TAT GAA ACA GGA ACT GTA AAT AAA TCA AAT GTT
 E   K   K   Y   H   P   K   G   S   K   N   E   T   S   Y   E   T   G   T   V   N   K   S   N   V
2043
GAA GAG GTT TCT GAA ACT TTA ACT AAT AGT GGA GTT GAA AGT GGA AGT CTT GAA AAA AAT ATT ATT ACA GCA CCA
 E   E   V   S   E   T   L   T   N   S   G   V   E   S   G   S   L   E   K   N   I   I   T   A   P
2118
CCA TCT ATA CCA AAA ATT CCT GAA GGT CCA CTA CCA GTG CCA ATT TTA ATT CCA GCT GAT CAA GTA CAA ACT ATT
 P   S   I   P   K   I   P   E   G   P   L   P   V   P   I   L   I   P   A   D   Q   V   Q   T   I
2193
TGT GAT TAT GAA GGT ATT AAA GTA CAA ATT AAA TCA CCA CAA TCA TTT ACT GGT GTT ATC TTT GTT AAA AAT CAC
 C   D   Y   E   G   I   K   V   Q   I   K   S   P   Q   S   F   T   G   V   I   F   V   K   N   H
2268
TAT GAA ACA TGT CGT GTT GAA GTT TCC AAC TCT GAT GCA GCT ACT CTT GAG CTT GGT CTT CCA GCT TCA TTT GGA
 Y   E   T   C   R   V   E   V   S   N   S   D   A   A   T   L   E   L   G   L   P   A   S   F   G
2343
ATG AAA CCA GTT ACA CTG TCT GCT ACA TCT TCA GAT TCT ACC TCT TCA CAG AAT ATT ACT TCT AAT AGT GGA CAT
 M   K   P   V   T   L   S   A   T   S   S   D   S   T   S   S   Q   N   I   T   S   N   S   G   H
2418
AAA GTT GTT GGA AGA GCA CGC CGT GAT ACA CAA GAA AAA TCT TGT GGT CTT ACA GAA ATT GAA AAT GGA AAA TAT
 K   V   V   G   R   A   R   R   D   T   Q   E   K   S   C   G   L   T   E   I   E   N   G   K   Y
2493
AAA AGT ACT GTT GTT ATA CAA ACA AAT AAC CTT GGA ATT CCT GGA CTT GTA ACA TCA ACA GAT CAA ATT TAT GAA
 K   S   T   V   V   I   Q   T   N   N   L   G   I   P   G   L   V   T   S   T   D   Q   I   Y   E
2568
ATT GGT TGT GAT TAT AGT AGT ATG TTA GGA GGA AAA ATT ACT ACA GCA GCT AAT ATG ACT GTA AAT GGA CCA ACA
 I   G   C   D   Y   S   S   M   L   G   G   K   I   T   T   A   A   N   M   T   V   N   G   P   T
2643
CCA ACT GAT ATT AAA CCT AGA GGT AAA ATT GAA CTT GGA AAT CCT GTT CTT ATG CAA ATG AAT GCT GGT ACA GGT
 P   T   D   I   K   P   R   G   K   I   E   L   G   N   P   V   L   M   Q   M   N   A   G   T   G
2718
GAT CAT CAG CCA ATT TTA CAA GCT AAA CTT GGA GAT ATT CTT GAA TTA AGA TGG GAA ATT ATG GCT ATG GAT GAA
 D   H   Q   P   I   L   Q   A   K   L   G   D   I   L   E   L   R   W   E   I   M   A   M   D   E
2793
GAA CTT GAT TTC TTT GTT AAA GAT TGT CAT GCA GAA CCT GGT ACT GGT GCT GGA GGA GAT GAA AAA CTT CAG CTT
 E   L   D   F   F   V   K   D   C   H   A   E   P   G   T   G   A   G   G   D   E   K   L   Q   L
2868
ATT GAA GGT GGA TGC CCA ACA CCA GCT GTT GCT CAA AAA CTT ATT CCA CAA CCA ATA AAA TTA CAA TCA TCA GCT
 I   E   G   G   C   P   T   P   A   V   A   Q   K   L   I   P   Q   P   I   K   L   Q   S   S   A
2943
GTC AAA ATT GCC CAT CTT CAA GCT TTC CGT TTT GAT TCA TCC TCT TCA GTT AGA ATA ACA TGT AAT ATT GAA ATT
 V   K   I   A   H   L   Q   A   F   R   F   D   S   S   S   S   V   R   I   T   C   N   I   E   I
3018
TGT AAG GGA GAT TGT AAA CCA GCA ACA TGT GAT ATG CAC GGA GAA TCA AAA CAA TCA TGG GGA AGA AAA AAG AGA
 C   K   G   D   C   K   P   A   T   C   D   M   H   G   E   S   K   Q   S   W   G   R   K   K   R
3093
CAT ATT GAA GAT GAT ACA ATT ACA GAA TTT GAG ACA AAT CGT TAT AAA GTT CCA AGA TTT TCA CAA GCA ACA ACA
 H   I   E   D   D   T   I   T   E   F   E   T   N   R   Y   K   V   P   R   F   S   Q   A   T   T
```

FIG. 1B

```
3168
TCT CTT TTA ATT CTT GAT CCA CTT CAA AAT AAC ATT GAA CCA GCA TCA TTA ATG TCA AAA GTA TCA TCT CTT GAT
 S   L   L   I   L   D   P   L   Q   N   N   I   E   P   A   S   L   M   S   K   V   S   S   L   D
3243
TTG TTA GCT GAA GAT CCT GCA AAA ACA TTA CTT AAG ATT AAA GAG ACT GCA CAT TTG AAT GGA AAT CTT TGT ATG
 L   L   A   E   D   P   A   K   T   L   L   K   I   K   E   T   A   H   L   N   G   N   L   C   M
3318
GGA AAA ATT ACA CTT TTC TCA GTA TTT GGT GTT CTT CTT TCA TTA ATT GTT GTT CAA GCA ATT GTC GTA ACA AAT
 G   K   I   T   L   F   S   V   F   G   V   L   L   S   L   I   V   V   Q   A   I   V   V   T   N
3393
TAT ATT TTT AAA AGA GTT ATG TCA AGC AGA AAG ATT ACC AAT TAAactttaataattaaacaataattataaatatgcctttatgt
 Y   I   F   K   R   V   M   S   S   R   K   I   T   N
3479
tctcaaaacgagtataatcctttttttttgttattaattttagtatcaaaatatatatacccgatggcatttacaataataataaatacaactgaagaaag
3579
ctataatatgaaaccgtgccagaaacttattcaaagttttaatctctctctctctctttctaatttcctttcaaaacattccatttttttttttttgttt
3679
ttatttaatcaaaaaataataattaaatagtaatttatgatatatcattaatattttataatatttttttg
```

FIG. 1C

```
1
ggcacgagaa ATG AAC TGG CTA TCT ATA GCT TCA ATT TGT ACA TTC TTA ATT ATA CCA ATA TCT GCT GTC TTT GAA
            M   N   W   L   S   I   A   S   I   C   T   F   L   I   I   P   I   S   A   V   F   E
77
TGT TCA GGA TCA GAA ACT ACA GCA TTT ATT AGA ATA TCC AGA GCA CGC CTT GAT GGG ACA CCA GTA GTT ATT TCT
C   S   G   S   E   T   T   A   F   I   R   I   S   R   A   R   L   D   G   T   P   V   V   I   S
152
ACA GCA GGA CAT GAC TTG ACT TGT GCA CAA TAT TGT AGA AAT AAT ATT GAA CCA ACA ACT GGT GCT CAA CGT GTC
T   A   G   H   D   L   T   C   A   Q   Y   C   R   N   N   I   E   P   T   T   G   A   Q   R   V
227
TGT GCA TCA TTT AAT TTT GAT GGT CGT GAA ACA TGC TAC TTT TTT GAT GAT GCT GCC TCA CCT GCT GGG ACT GGG
C   A   S   F   N   F   D   G   R   E   T   C   Y   F   F   D   D   A   A   S   P   A   G   T   G
302
GAG TTG AAT GAA GCA CCA TCA GCT AAT AAT TTT TAT TAT GAA AAA GTT TGC CTT CCA GCT ATC TCT GCT CAT GAA
E   L   N   E   A   P   S   A   N   N   F   Y   Y   E   K   V   C   L   P   A   I   S   A   H   E
377
GCA TGT ACT TAT AGA TCA TTT TCA TTT GAA AGA ACT AGA AAT ACT CAA TTA GAA GGT TTT GTT AAA AAA TCA CTA
A   C   T   Y   R   S   F   S   F   E   R   T   R   N   T   Q   L   E   G   F   V   K   K   S   L
452
CAA GTT ACA TCA CGT GAA GAA TGC CTT TCT ACA TGT TTA AAA GAA AGT GAA TTT GTA TGT AGA TCA GTT AAC TAT
Q   V   T   S   R   E   E   C   L   S   T   C   L   K   E   S   E   F   V   C   R   S   V   N   Y
527
AAT TAT GAA AAC TTT ATG TGT GAA CTT TCA ACA GAA AGA TCG CGT TCT AAA CCA CAA AAT ATG AGA ATG TCA GCA
N   Y   E   N   F   M   C   E   L   S   T   E   R   S   R   S   K   P   Q   N   M   R   M   S   A
602
GCT CCA GTT GAT TAT TAT GAT AAT AAT TGT TTA AAT AGA CAA AAT AGA TGT GGT GAA TCT GGT GGA AAT TTG ATT
A   P   V   D   Y   Y   D   N   N   C   L   N   R   Q   N   R   C   G   E   S   G   G   N   L   I
677
TTT ATT AAA ACA ACA CAA TTT GAA ATT CAT TAT TAT GAT CAT ACT CAA TCA ATG GAA GCA CAA GAA TCA TTC TGT
F   I   K   T   T   Q   F   E   I   H   Y   Y   D   H   T   Q   S   M   E   A   Q   E   S   F   C
752
TTA CAA AAA TGT TTA GAT TCA TTA AAC ACC TTC TGT AGA TCT GTT GAA TAT TCT CCA TCT GAA AAA AAT TGT ATT
L   Q   K   C   L   D   S   L   N   T   F   C   R   S   V   E   Y   S   P   S   E   K   N   C   I
827
GTT TCT GAT GAA GAT ACA TAT TCA AGA GCT GAT CAA CAA GGT GAA GTT AAT AAT AAA GAT TAT TAT GAA CCT GTT
V   S   D   E   D   T   Y   S   R   A   D   Q   Q   G   E   V   N   N   K   D   Y   Y   E   P   V
902
TGT GTT GCT GCT GAT CTT AGT TCA TCT ACA TGT CGT CAA CAA GCT GCT TTT GAA AGA TTT ATT GGT TCT GCT ATT
C   V   A   A   D   L   S   S   S   T   C   R   Q   Q   A   A   F   E   R   F   I   G   S   A   I
977
GAA GGT ACC CCA GTT GCT ACA GCA CAA CAA GTA ACC ATT TCT GAT TGT ATT TCA CTT TGT TTC CAA AAT TTG AAT
E   G   T   P   V   A   T   A   Q   Q   V   T   I   S   D   C   I   S   L   C   F   Q   N   L   N
1052
TGT AAA TCA ATT AAT TAT GAT CGT ACA CAA TCT ACA TGT TAT ATT TAT GCT GTT GGA AGA CAA GAA TCT AAT GTT
C   K   S   I   N   Y   D   R   T   Q   S   T   C   Y   I   Y   A   V   G   R   Q   E   S   N   V
1127
AAA AAT GAT GCA AGT TTC GAT TAT TAT GAA TTT ACA ATT ATT GAT AAT GGA TGC CCA AGA TAT CCT GCT CTT GTA
K   N   D   A   S   F   D   Y   Y   E   F   T   I   I   D   N   G   C   P   R   Y   P   A   L   V
1202
GGG CCA GTT TTA CAA GAT TTC GAC AAA AAT CGT CTT AAA TCT GAA ATG AAA GCA TTC CGT TTA GAT GGA TCA TAT
G   P   V   L   Q   D   F   D   K   N   R   L   K   S   E   M   K   A   F   R   L   D   G   S   Y
1277
GAT ATT CAA ATT GAA TGT TCT GTT ATG TTT TGT GCT GGT CCA ATG GGT TGT CCA CCA TCT AAT TGC CTT GAT TCA
D   I   Q   I   E   C   S   V   M   F   C   A   G   P   M   G   C   P   P   S   N   C   L   D   S
1352
GGA ACA AAT GAA TTA TTT GCT TCA CAT GGA AGA AAG AAA AGA AGT ATT GTT GAT TTC AAA AAT ACA ACA ACA TCT
G   T   N   E   L   F   A   S   H   G   R   K   K   R   S   I   V   D   F   K   N   T   T   T   S
1427
GCA GAA ACA TTA TCT GCT ATA ATT AGA GTA CTT GCT GCT GGA GAA GAA GAA TTA GAA GTT GAA GAA TTT TAT AGA
A   E   T   L   S   A   I   I   R   V   L   A   A   G   E   E   E   L   E   V   E   E   F   Y   R
1502
AAT GAT ACT AAT TTT AAA TAT GAT TCT GAA GAA AAT ATC TCA GCT CAT AAC TTA TAC TGT ATG TCT GAA ATG TGG
N   D   T   N   F   K   Y   D   S   E   E   N   I   S   A   H   N   L   Y   C   M   S   E   M   W
```

FIG. 2A

```
1577
TTT GTA TCA GGA ATT GTT TCA ATG GCT ATG ATC TGT CTT CTT CTT TCT GTT CTT ATA GTT ATG TGG GGC TGT CAT
 F   V   S   G   I   V   S   M   A   M   I   C   L   L   L   S   V   L   I   V   M   W   G   C   H
1652
TCA TTA AAT CAA TCT TCA AAA TTA CCA ATG TGAaggaagatctttcaacaaaaaaaaacgattaattttttaatatttctttaatatatac
 S   L   N   Q   S   S   K   L   P   M
1742
attccataatcagtatatactataataattgcaacataataatttattgtagaagtctgtttataaaatcaaatcacaaatttttcttttacagtactgt
1842
gcacaacaacaagaaattccaatctcttcctatattttgatgtcgtacacgtttataaaaacaaattcttttggtttttaatcagttttcagtttaca
1942
tttatataat
```

FIG. 2B 1
gcgtcgatagtccgatttttaaggtttaattacccaagcttaaggaatatttgaagcttattttaaagaaaaaataaattaaataagagattagcaca 101
acaacaacagaaatttttcttgaatttacaacaaaataattttttcttaattaaattcctttaaattatccacaacttct ATG GTT ACA AAA ATC
                                                                                  M   V   T   K   I
196
CCA ACT TTT CCC CTC CTT TTT ATT TTC CCA TTT TTA TTT ACA TTT TTA ACG ACA AAA TGT CAG GCT TAT TCT ATA
P   T   F   P   L   L   F   I   F   P   F   L   F   T   F   L   T   T   K   C   Q   A   Y   S   I
271
CCA TTA ATA TCA GAA TGT AAT TCG GAA GAA GCC CCA GTT TTT CTT TTG CAA CGG AAT GTT TCT TCT ATC GCC GGA
P   L   I   S   E   C   N   S   E   E   A   P   V   F   L   L   Q   R   N   V   S   S   I   A   G
346
ACT GAG CCT TTA AGA ACT GTT CCT GTT ACA GGG GGA TTT TTG GAA TGT GCG GAA CTT TGT TCA GCA GCA AAT AAT
T   E   P   L   R   T   V   P   V   T   G   G   F   L   E   C   A   E   L   C   S   A   A   N   N
421
TGT GTT GCT GTT AAA TTT TCT ATT GAA AAA CAA TGC CAA TTG TTG GGG AAA ACA ACT ATG ACA GCA ACA ACT TTA
C   V   A   V   K   F   S   I   E   K   Q   C   Q   L   L   G   K   T   T   M   T   A   T   T   L
496
TCT TTA CAA GAC ATT AAT TTG ACA CTA GCT AGA TTA GCT ACT AAA AGT TGT GTT AAG AGC AAA AAA ATC TGT TCT
S   L   Q   D   I   N   L   T   L   A   R   L   A   T   K   S   C   V   K   S   K   K   I   C   S
571
TCC CCC TTC CAT TTT GAT GTT CAC GAA CAA AAA ATA CTT GTT GGT TTT GCT AGA GAA GTT GTA TCA GCA GAA TCT
S   P   F   H   F   D   V   H   E   Q   K   I   L   V   G   F   A   R   E   V   V   S   A   E   S
646
ATA CAT CAA TGT TTA ACT GCT TGT TTA GAT GCT GTT GAT ACT TTT GGC TTT GAA TGC GAG TCA GTA ATG TAT TAT
I   H   Q   C   L   T   A   C   L   D   A   V   D   T   F   G   F   E   C   E   S   V   M   Y   Y
721
CCA TTG GAT GCC GAA TGT ATT TTA AAT ACA GAA GAC AGA CTT GAC CGT CCA GAT TTG TTT GTT GAT GAG AAG GAA
P   L   D   A   E   C   I   L   N   T   E   D   R   L   D   R   P   D   L   F   V   D   E   K   E
796
GAT ACT GTT GTT TAT TTG GAT AAT AAT TGT GCT GGA TCC CAA TGT CAT GCC CCT TAT GTA ACC CAA TAT GTA GCT
D   T   V   V   Y   L   D   N   N   C   A   G   S   Q   C   H   A   P   Y   V   T   Q   Y   V   A
871
GTT GAA GGA AAA CAA TTA GCT GAG GAA TTG GAT CAT AAT TTT GAG GGA ATG GAG TTG ACA GAA TGT GAA CAG CTT
V   E   G   K   Q   L   A   E   E   L   D   H   N   F   E   G   M   E   L   T   E   C   E   Q   L
946
TGT AAT CAA AGA TTG AGT GTT TCT GCA AAT GAC TTT AAT TGC AAA GCA TTT ATG TAC AAT AAC CAA ACA AGA TCT
C   N   Q   R   L   S   V   S   A   N   D   F   N   C   K   A   F   M   Y   N   N   Q   T   R   S
1021
TGT ATT CTT TCT GAT GAA CGT TCA AGA CCT TTG GGT AGA GCT AAT TTG ACA GAT GCT AAA GGA TGG ACT TAT CAC
C   I   L   S   D   E   R   S   R   P   L   G   R   A   N   L   T   D   A   K   G   W   T   Y   H
1096
GAG AAA AAA TGT TTT GCC TCC CCA CGT ACA TGC CGA AAT GTT CCT TCT TTT ACC CGC GTC CCT CAA ATG TTA TTA
E   K   K   C   F   A   S   P   R   T   C   R   N   V   P   S   F   T   R   V   P   Q   M   L   L
1171
GTT GGA TTT GCC TCT TTT GTA ATG GAA AAT GTC CCT TCA GTA ACT ATG TGT TTG GAT CAA TGT ACA AAT CCT CCC
V   G   F   A   S   F   V   M   E   N   V   P   S   V   T   M   C   L   D   Q   C   T   N   P   P
1246
CCA GAA ACT GGA CAA AGT TTT GTT TGT AAA TCT GTC ATG TAT TAT TAT AAT GAG CAA GAA TGT ATT TTA AAT GCT
P   E   T   G   Q   S   F   V   C   K   S   V   M   Y   Y   Y   N   E   Q   E   C   I   L   N   A
1321
GAA TCA CGT CAT TCC AAG CCA GAT TTA TTT ATT CCC GAA GAA GAC GAT TTT GTT GTA GAT TAT TTT GAT ATA AAT
E   S   R   H   S   K   P   D   L   F   I   P   E   E   D   D   F   V   V   D   Y   F   D   I   N
1396
TGC CGT CTA GAA CAA GAA CAA TGT ATC GAT GGA AGA ACG CCC CAA TTA GTT AGA ACA ATT AAT TCT GCA CTT CCA
C   R   L   E   Q   E   Q   C   I   D   G   R   T   P   Q   L   V   R   T   I   N   S   A   L   P
1471
GAA GGG GAG GGG TCT ATA CAT GTT TTG GAA ACA ATT AAG GGA GGA GTT CAG CAA TGT GCT AAA AAA TGT TCT GAA
E   G   E   G   S   I   H   V   L   E   T   I   K   G   G   V   Q   Q   C   A   K   K   C   S   E
1546

FIG. 3A

```
       CGC GCC CCA GAC AAA TGT CGC TCT TTC AAT TTT GAT AAA CAA GCT GGT AAT TGT AAT TTA CTT TAT TTG GAT GGA
       R   A   P   D   K   C   R   S   F   N   F   D   K   Q   A   G   N   C   N   L   L   Y   L   D   G
1621
CAA GGG TCT TTA CGA CCA GAG CAA AAG ACA CAA TTC GAT TTA TAC GAT GTT CAT TGT TTG AGT GGA ACA TCT CAA
Q   G   S   L   R   P   E   Q   K   T   Q   F   D   L   Y   D   V   H   C   L   S   G   T   S   Q
1696
CTT TTA GGA GAA AAT TCT AAA CAT TCT CCC TCT GCT TGT GTT GAC CCA GAA GGG GCT ATT TTT AGT CGT TTC CTC
L   L   G   E   N   S   K   H   S   P   S   A   C   V   D   P   E   G   A   I   F   S   R   F   L
1771
TAC ACT CGT TGG GTA GCA AAT TCT CCC AAT CGT GAA ATT TCA AGT TTA CCA CTT TCC AAA TGT TTA AAT CTT TGT
Y   T   R   W   V   A   N   S   P   N   R   E   I   S   S   L   P   L   S   K   C   L   N   L   C
1846
TCG GTT GGA GGA GAA CAA TGT GAG GGT GTT AAT TAC AAT CGC CGA AAT GGT TCT TGT CAA TTA TTT ACT TCC CTT
S   V   G   G   E   Q   C   E   G   V   N   Y   N   R   R   N   G   S   C   Q   L   F   T   S   L
1921
CTA TTA AAC TCT TCT CCA AAT TCT CAA CAA GAC AAA GAC GAA CAT GTT GAT TTT TAC AGA AAT ATT TGT AGA GTT
L   L   N   S   S   P   N   S   Q   Q   D   K   D   E   H   V   D   F   Y   R   N   I   C   R   V
1996
AAG GAA TCG AAA AGT GAT AGT GGG GCT GCT AAT GTA CCC AAA ACA CAA CAA GCA ACG GCT GCA CCT CCC CCT TCT
K   E   S   K   S   D   S   G   A   A   N   V   P   K   T   Q   Q   A   T   A   A   P   P   P   S
2071
GTT CAA TTA ACT ACT AAA CCT CCA CAA ATT CGT GAT TTA AAC AAC AAC AAT AAA ACA ACA CAC AAA GAA CCA AAT
V   Q   L   T   T   K   P   P   Q   I   R   D   L   N   N   N   N   K   T   T   H   K   E   P   N
2146
ATT AAA CTT CCA CCA CAA TCA GCA AAA CCT ATA AAT GGA AAA ACT GGA AAG GAA CAA CTT CCT GTA GGG TCA AAA
I   K   L   P   P   Q   S   A   K   P   I   N   G   K   T   G   K   E   Q   L   P   V   G   S   K
2221
TCT TTT GGG GTT ACT AAT ACG CGT GAT GAT GGG GAG AAT TCA ATA ACT GGA ACT GCT CCT CCT CCT GTA GAT GGC
S   F   G   V   T   N   T   R   D   D   G   E   N   S   I   T   G   T   A   P   P   P   V   D   G
2296
AAA TTA ATT ATT AAA CCT TCA CCA CAA GTT TCT ATT CCC TCC CCT GTA CTT ATT CCG GCA CAA GAA GTA CAT ACT
K   L   I   I   K   P   S   P   Q   V   S   I   P   S   P   V   L   I   P   A   Q   E   V   H   T
2371
ATT TGT AAT TAT GAA GGA ATT AGT GTT CAA ATT AAA CAT TCT TCT CCA TTC TCT GGC GTT GTT TTT GTT CGA AAT
I   C   N   Y   E   G   I   S   V   Q   I   K   H   S   S   P   F   S   G   V   V   F   V   R   N
2446
AAA TAT GAT ACT TGC CGT GTG AAG TTG AAG GAA AGG ACA GCG TTG TTT TGG TTT TGG GGC TTC CAG CAA ATT TTG
K   Y   D   T   C   R   V   K   L   K   E   R   T   A   L   F   W   F   W   G   F   Q   Q   I   L
2521
GAA ATG AAG CCA ATT GCT TTA ATT AAT TCA CAA AAA CAT GGA AAA GGG AAT AAA ACA CAC GGA GAT ACT TTA CTT
E   M   K   P   I   A   L   I   N   S   Q   K   H   G   K   G   N   K   T   H   G   D   T   L   L
2596
TCT ATT GAA GGT TCC AAA AAA CAA ATT GAA GGG GGT TCT TCA ACT GAA GAT ATT CAA TTA ATA AAT TCT CAA AAA
S   I   E   G   S   K   K   Q   I   E   G   G   S   S   T   E   D   I   Q   L   I   N   S   Q   K
2671
GAC CTT AAA CGT TCA AGA AGA CAA TTA CAA AGA GAT TGT GGA TTA CAA GAT ATG GAC AAT GGA ACT TAC AAA ACT
D   L   K   R   S   R   R   Q   L   Q   R   D   C   G   L   Q   D   M   D   N   G   T   Y   K   T
2746
GTT ATT GTT GTC CAA ACA AAT AAT TTG GGA ATT CCG GGA CTT GTT ACT TCT ATG GAC CAA CTT TAT GAG ATT TCC
V   I   V   V   Q   T   N   N   L   G   I   P   G   L   V   T   S   M   D   Q   L   Y   E   I   S
2821
TGT AAC TAT TCA AGT ATG TTG GGA GGC AAA GTC CAA ACA GCA GCT GCA TTA CGT GTT CAC GGT CCC CAA CCT TCA
C   N   Y   S   S   M   L   G   G   K   V   Q   T   A   A   A   L   R   V   H   G   P   Q   P   S
2896
CTA ATC CAG CCT CGC GGC AAA ATA GAA TTG GGA AAT CCT GTT TTG ATG CAA ATG GGG CCT GTA CGT AGT GAA AGG
L   I   Q   P   R   G   K   I   E   L   G   N   P   V   L   M   Q   M   G   P   V   R   S   E   R
2971
CAA AGT GGG GAA GGG CCT TTA ATT CAA GCT AAA TTG GGG GAT ATT CTT GAA TTA AAA TGG GAA ATT ATG GCA ATG
Q   S   G   E   G   P   L   I   Q   A   K   L   G   D   I   L   E   L   K   W   E   I   M   A   M
3046
GAT GAA GAA TTG GAC TTT TTA GTT CGT GAT TGT TTT GCA GAG CCG GGA ACT TCT GGA AAT CAA GGG GAA AGA CTT
D   E   E   L   D   F   L   V   R   D   C   F   A   E   P   G   T   S   G   N   Q   G   E   R   L
```

FIG. 3B

```
                          3121
CCT TTA ATT GAG AAT GGT TGT CCA ACA CCA GCA GTA GCA CAA AAA TTA ATT CCA AAT CCA ATA AAA GCA ATT AAT
 P   L   I   E   N   G   C   P   T   P   A   V   A   Q   K   L   I   P   N   P   I   K   A   I   N
3196
TCT GCA GTT AAA TTA ACT TAT TTA CAA GCA TTC AGA TTT GAC AGT TCT CCA GCT ATT AGA ATA ACT TGT CAT TTA
 S   A   V   K   L   T   Y   L   Q   A   F   R   F   D   S   S   P   A   I   R   I   T   C   H   L
3271
GAA TTA TGT AAA GAA AAT TGT AAA TCG GTT AAT TGT AAA TTT AAT GAT GGA ATT AAA GAA TCG TGG GGC AGA AAA
 E   L   C   K   E   N   C   K   S   V   N   C   K   F   N   D   G   I   K   E   S   W   G   R   K
3346
CGC CGT TTT GCT ATT GAC AAT AAC ATT AAT AGG AAA AAT GAA GTT AAA GAA TTC GAA ACT CGC CGT TTT GTC GTT
 R   R   F   A   I   D   N   N   I   N   R   K   N   E   V   K   E   F   E   T   R   R   F   V   V
3421
CCC CGT TTT GCC CAA GCA ACA ACT TCT TTA GTT ATT GTA GAC CCT TTA CAA CAA CAA AAT TCT GTT ATA AAA ACA
 P   R   F   A   Q   A   T   T   S   L   V   I   V   D   P   L   Q   Q   Q   N   S   V   I   K   T
3496
GAA CAA CAA CAA CAA CCA TTT ATT TCA CAT TCC TCA ATA TCT AAA CAA ATA TTT GAA AAT AAT AAA AAA GAA AAT
 E   Q   Q   Q   Q   P   F   I   S   H   S   S   I   S   K   Q   I   F   E   N   N   K   K   E   N
3571
AAT AAA AAT ATA ACA AAA ACA GCT AAA AAA TCC TCT TCT CTT TTT GAA GCT TTT ACT GAG GCT GCT GGT GGA AGG
 N   K   N   I   T   K   T   A   K   K   S   S   S   L   F   E   A   F   T   E   A   A   G   G   R
3646
AAA ATT AAT TTA GAA TTA ACA ACA ACA AAT TCA GAA CAA CAA CAA CTT TGT TTA CAT AAA TGG ACA CTT GGG GGT
 K   I   N   L   E   L   T   T   T   N   S   E   Q   Q   Q   L   C   L   H   K   W   T   L   G   G
3721
GTT TTT GGA ACT CTT TTA ACA TTA ATT GTT GTT CAA AGC GGG GTT GCT GCT AAA CAT TTA ATT AAT CGA TTT ATT
 V   F   G   T   L   L   T   L   I   V   V   Q   S   G   V   A   A   K   H   L   I   N   R   F   I
3796
GTT GGA AAA AGA ATT TAAaaaaaaaaaaaaaaagtactagtcgacgcgtggcc
 V   G   K   R   I
```

FIG. 3C

```
1
GAG CAG AAG ATT TTG GTG GGT TTC GCG CGG GAG GTG GTC TCC GCC GAC TCA GTC CAC CGC TGT CTG
 E   Q   K   I   L   V   G   F   A   R   E   V   V   S   A   D   S   V   H   R   C   L
67
TCC GCT TGT CTG AAT GCG TTC GAT ACG TTC GGC TTC GAA TGC GAG TCG GTC ATG TAT TAC CCT GTG GAC GCG GAA
 S   A   C   L   N   A   F   D   T   F   G   F   E   C   E   S   V   M   Y   Y   P   V   D   A   E
142
TGC ATT TTG AAC ACG GAG GAC CGA TTG GAT CGG CCT GAC CTT TTC GTG GAC GAG CAC GAG GAC ACG GTC ATC TAC
 C   I   L   N   T   E   D   R   L   D   R   P   D   L   F   V   D   E   H   E   D   T   V   I   Y
217
TTG GAC AAC AAT TGC GCC GGA TGT GAG TGC CAT TGG CAT TTT GAC AAT TTC AAA ACA AGC GGC ATT TTG AAC GAC
 L   D   N   N   C   A   G   C   E   C   H   W   H   F   D   N   F   K   T   S   G   I   L   N   D
292
CAA CAA TTC GCA ATT GCA GCA CAA TGT TAC GCA CCG TAC GTA ACG CAA TAC GTG GCG GTG GAA GGA CGC CAA TTG
 Q   Q   F   A   I   A   A   Q   C   Y   A   P   Y   V   T   Q   Y   V   A   V   E   G   R   Q   L
367
TCG GAC GAA TTG GAC CAC AGT TTT GAA GGG TTG GAG CTG AGC GAA TGT GAA GAG TTG TGC ACG CAA CGG TTA AGT
 S   D   E   L   D   H   S   F   E   G   L   E   L   S   E   C   E   E   L   C   T   Q   R   L   S
442
GTT ACG GCA AAC GAC TTC AAC TGC AAA TCG TTC ATG TAC AGT AAC TTG ACG CGC AGT TGC GTT TTG TCG GAC GAA
 V   T   A   N   D   F   N   C   K   S   F   M   Y   S   N   L   T   R   S   C   V   L   S   D   E
517
CGC TCG CGC CCT TTG GGC CGT GCC AAT TTG GCC GAA GTG CCG GGA TGG ACT TAT TTC GAG AGC CGC GGC GTT CCG
 R   S   R   P   L   G   R   A   N   L   A   E   V   P   G   W   T   Y   F   E   S   R   G   V   P
592
TCG TTT ACG CGA GTG CCG CAA ATG CTT TTG GTG GGC TTT GCC TCT TTT GTG ATG GAA AAT GTG CCG TCA GTG ACA
 S   F   T   R   V   P   Q   M   L   L   V   G   F   A   S   F   V   M   E   N   V   P   S   V   T
667
ATG TGT TTG GAC CAA TGC ACA AGC CCT CCT CCT GAG ACG GGA CAA AAC TTT GTG TGT AAA TCG GTG ATG TAC TAC
 M   C   L   D   Q   C   T   S   P   P   P   E   T   G   Q   N   F   V   C   K   S   V   M   Y   Y
742
TAC AAC GAG CA
 Y   N   E
```

FIG. 4

1
cgactggagcacgaggacactgacatggactgaaggagtagaaaatttctgttgttcatttcttatcagactgtcccattcatcatcgtgaccactacca
101
gtattacttcaggacagtaatattcgggtaaatttcggctgctcaatcggtaggaccgctttaat ATG CAT CTT TCC AAC CAT GCC TCA
                                                                   M   H   L   S   N   H   A   S
190
TCA CTT CTG CAT TAC TAT TCA CAT CTC ATC ATA ATT GCA TAC TTT TCT GTA TTT GCT TCA ATC GAA ATA CAA GAA
 S   L   L   H   Y   Y   S   H   L   I   I   I   A   Y   F   S   V   F   A   S   I   E   I   Q   E
265
ATT CCA TCA TAT CCA GCA TGT AGC AAT GGC GAA TCA CCT GTC TTT TTA CTC CAA CAC AAT GCT ACA GCA GGT AAT
 I   P   S   Y   P   A   C   S   N   G   E   S   P   V   F   L   L   Q   H   N   A   T   A   G   N
340
GTT CTG AAG CGA GCT TCA ACT TCA CAT CTG GTC GAC TGC ACT GAC CTT TGT TCA GCT AAC GAT GAA TGT TTG GCG
 V   L   K   R   A   S   T   S   H   L   V   D   C   T   D   L   C   S   A   N   D   E   C   L   A
415
ATA ACC TAT GAA GAT AAA GAA TGC AAA ATG TTG TCA AGC ATT GGA GAA TCG ACA GGA CAT TTA AAT GAT TAT GTA
 I   T   Y   E   D   K   E   C   K   M   L   S   S   I   G   E   S   T   G   H   L   N   D   Y   V
490
TTG CTG AGT AAA AAT TGT GCT AAA AGT GCG CGG ATC TGC TCA TCG CCA TTT CAA TTC GAT GTA CAC AGA CAA AAA
 L   L   S   K   N   C   A   K   S   A   R   I   C   S   S   P   F   Q   F   D   V   H   R   Q   K
565
ATT TTG GTT GGG TTT GCT CGC GAG GTT GTG TCA GCT GAT TCA TTA TCG TTA TGT CTA TCA GCT TGC TTG AAT GCA
 I   L   V   G   F   A   R   E   V   V   S   A   D   S   L   S   L   C   L   S   A   C   L   N   A
640
TTT GAT TCT TTC GGT TTT GAA TGT GAG TCG GTA ATG TAC TAT CCA GTT GAT TCA GAA TGC ATC CTA AAC ACC GAA
 F   D   S   F   G   F   E   C   E   S   V   M   Y   Y   P   V   D   S   E   C   I   L   N   T   E
715
GAT CGT CTG GAT CGA CCT GAC TTG TTT GGG GAT GAA TTA GAT GAT AAC GTC ATT TAT TTG GAT AAC AAC TGT GCT
 D   R   L   D   R   P   D   L   F   G   D   E   L   D   D   N   V   I   Y   L   D   N   N   C   A
790
GGA TCA CAG TGT TAT GCT CCA TAC ATA ACA CAA TAC ATT GCC GTC GCA AAT CGT CAG CTA GCT AAC GAG TTG GAC
 G   S   Q   C   Y   A   P   Y   I   T   Q   Y   I   A   V   A   N   R   Q   L   A   N   E   L   D
865
AGA CAA CTG ATC GCT GAT CGT GAA TCA TGC GAG TCG TTA TGT ACT CAG CGA CTG TCT ACA ACG ACA AAC GAT TTC
 R   Q   L   I   A   D   R   E   S   C   E   S   L   C   T   Q   R   L   S   T   T   T   N   D   F
940
AAC TGT AAA TCA TTT ATG CAT AAT CCG GAA ACT AAC GTT TGC ATA CTT TCT GAT GAA CGT TCT AAA CCA CTT GGT
 N   C   K   S   F   M   H   N   P   E   T   N   V   C   I   L   S   D   E   R   S   K   P   L   G
1015
CGA GGC AAT CTA GTG AAA GCT GAC GGT TTC ACA TAT TAT GAG AAG AAA TGT TTT GCA TCA CCA CGA ACA TGT CGC
 R   G   N   L   V   K   A   D   G   F   T   Y   Y   E   K   K   C   F   A   S   P   R   T   C   R
1090
AAT GTA CCG TCG TTT GAG CGC ATA CCT CAG ATG ATA CTT GTT GGT TTT GCT GCA TTT GTT ATG GAA AAT GTA CCT
 N   V   P   S   F   E   R   I   P   Q   M   I   L   V   G   F   A   A   F   V   M   E   N   V   P
1165
TCA GTA ACG ATG TGC CTC GAT CAG TGC ACA AAT CCT CCA CCG GAA ACT GGA GAA AAT TTC GAA TGC AAA TCT GTG
 S   V   T   M   C   L   D   Q   C   T   N   P   P   P   E   T   G   E   N   F   E   C   K   S   V
1240
ATG TAT TAT TAT AAC GAA CAG GAA TGT ATT TTA AAC GCT GAA ACA CGA GAA AAT AAA TCG GAA TTG TTT ATA CCG
 M   Y   Y   Y   N   E   Q   E   C   I   L   N   A   E   T   R   E   N   K   S   E   L   F   I   P
1315
GAG GGA GAA GAA TTC CAA GTC GAT TAT TTT GAT ATC ACT TGT CAT CTG CGC CCT GAA ACA TGT CCA AAT GGC ACA
 E   G   E   E   F   Q   V   D   Y   F   D   I   T   C   H   L   R   P   E   T   C   P   N   G   T
1390
ACA TTA CAT ACT GTA CGT ACG GTT AAT GCA GCA CTC CCT GAA GGC GAA GGA TCG ATC CAT ATT TTG CAG TCA GCC
 T   L   H   T   V   R   T   V   N   A   A   L   P   E   G   E   G   S   I   H   I   L   Q   S   A
1465
GGG AAT TCG GTT GCT GAT TGC ATG ACA AAA TGT TAC GAG ATG GCT CCC GAG AAA TGT CGC GCA TTC AAT TTT GAT
 G   N   S   V   A   D   C   M   T   K   C   Y   E   M   A   P   E   K   C   R   A   F   N   F   D

FIG. 5A

```
1540
AAG CAG ACA TCT GAC TGT GAC CTG CTG TAC GTT GAT GGG AAG ACA ACC TTA CGA CCA GCA GTC CAC TCG GGC ATT
 K   Q   T   S   D   C   D   L   L   Y   V   D   G   K   T   T   L   R   P   A   V   H   S   G   I
1615
GAT CTC TAC GAC CTT CAT TGC CTA GAG CAG ACA AAA GTT TGC GCT CAG AAA AAC AAC GTA ACA CGA TTT TCG AGA
 D   L   Y   D   L   H   C   L   E   Q   T   K   V   C   A   Q   K   N   N   V   T   R   F   S   R
1690
TAT TTG TAC AGT ATA TAT GAT GCA GTG CCA TCG CAA TTC TAC GAA GCA ACT GCC CTC ACA AAT TGT CTT AAT CTT
 Y   L   Y   S   I   Y   D   A   V   P   S   Q   F   Y   E   A   T   A   L   T   N   C   L   N   L
1765
TGC GCA TAT ACC GAG CGT TGC GAA GGT GTA AAT TAC AAC AGA AGG AAT GGT CGT TGT GAA TTA TTT GAT AAG GTC
 C   A   Y   T   E   R   C   E   G   V   N   Y   N   R   R   N   G   R   C   E   L   F   D   K   V
1840
GAA GGA AAT GGA AAG CCA AGT GAT TTC ACG GAT TTT TAC AAA AAT CTT TGT CTG GTG GAA GAA GTA GAA TCA GAA
 E   G   N   G   K   P   S   D   F   T   D   F   Y   K   N   L   C   L   V   E   E   V   E   S   E
1915
TAT AGC GCC GCA GCT AAT GTT CCC AAA CAT CTC CTT CCG AAT GTT TCA CAT TCT GCA GTT ACT CAG AAA CAA GAA
 Y   S   A   A   A   N   V   P   K   H   L   L   P   N   V   S   H   S   A   V   T   Q   K   Q   E
1990
GCT AAA TTA CAC ATT ATC TCA GCA AAA ACA AAG CCT TTC CTA CGC GAA CAG GAA GCA CAG CGA CGA GCT CCA GAA
 A   K   L   H   I   I   S   A   K   T   K   P   F   L   R   E   Q   E   A   Q   R   R   A   P   E
2065
ACA ATA ACA GCG AAG TCG TCT TCA GCT TCC GGA AAA GTA AGT GGT GAA GCA GGA TCA TCA ACT ACA TTC AGC ATT
 T   I   T   A   K   S   S   S   A   S   G   K   V   S   G   E   A   G   S   S   T   T   F   S   I
2140
TCT TCA TCC GGA AGG CTT CCA GGG CCA GTA GTC CAA ATT GCT CCA AAT GCA GTG CAA ACA GTT TGC AAT TAT GAA
 S   S   S   G   R   L   P   G   P   V   V   Q   I   A   P   N   A   V   Q   T   V   C   N   Y   E
2215
GGC ATC AAA GTG CAG ATG GAG AAC CCC AAA GCC TTT TCG GGA GTG ATA TTT GTT AAA AAT AGG TAT GAA ACC TGT
 G   I   K   V   Q   M   E   N   P   K   A   F   S   G   V   I   F   V   K   N   R   Y   E   T   C
2290
CGA GTA GAG GTT ACG GAT AGT GAA AGT GCA CCA CTA GTA ATT GGT TTA CCA CCG AAT TTT GGT TCA AAA ATG GTA
 R   V   E   V   T   D   S   E   S   A   P   L   V   I   G   L   P   P   N   F   G   S   K   M   V
2365
GCT GAT GAA AAG GTT GCC GCA AGC GAA GCA AAT ATT CAA CCA GAA ATA TCC GGA GGC GAC AAA CTG GAT AAA CCC
 A   D   E   K   V   A   A   S   E   A   N   I   Q   P   E   I   S   G   G   D   K   L   D   K   P
2440
GCT GAT GAA CTG CGC ATA AGA CGA CAA GCT TTA GAG CTA CAC AGA GAT TGC GGA ATC CAG GAT ATG AAC AAT GGT
 A   D   E   L   R   I   R   R   Q   A   L   E   L   H   R   D   C   G   I   Q   D   M   N   N   G
2515
ACT TAT AAA TCA ACG GTG GTT GTA CAA ACA AAT AAC TTG GGT ATA CCT GGA CTG GTA ACT TCC ATG GAT CAG ATT
 T   Y   K   S   T   V   V   V   Q   T   N   N   L   G   I   P   G   L   V   T   S   M   D   Q   I
2590
TTT GAA GTG AGC TGT GAT TAT AGT TCA ATG CTT GGT GGA AAA GTT ACT GCT GGT GCC AAT CTC ACA ATT GAT GGT
 F   E   V   S   C   D   Y   S   S   M   L   G   G   K   V   T   A   G   A   N   L   T   I   D   G
2665
CCC GAA GCA TCT CTT ATT CAA CCC CGA GGA AAA ATC GAA CTT GGT AAC CCG GTG CTT ATG CAG ATG TTG AGT GGA
 P   E   A   S   L   I   Q   P   R   G   K   I   E   L   G   N   P   V   L   M   Q   M   L   S   G
2740
CAA GGA GAA CCT GTC CTA CAA GCA AAA CTA GGT GAC ATT CTG CAG CTA CGA TGG GAA ATC ATG GCG ATG
 Q   G   E   P   V   L   Q   A   K   L   G   D   I   L   Q   L   R   W   E   I   M   A   M
```

```
SEQ_ID_NO_46   -MSPRVIFLLLGSFLTAQAVFECSSHETTAFVRIPRARLDGTPVVISTAGHDLTCAQYCRNNIEPTTGAQRVCASFNFDGRETCYFPDDAATPAGTSQLTANPSANNFYYEKTCIPNVSAHEACTYRSFS   129
SEQ_ID_NO_18   -MWG-VIFLLLSIVPAAQSVFECSSHETTAFVRIPRARLDGTPVVISTAGHDLTCAQYCRNNIEPTTGAQRVCASFNFDGRETCYFPDDAATPAGTSQLTANPSANNFYYEKTCIPNVSAHEACTYRSFS   128
SEQ_ID_NO_4    MNWLSIASICTFLIIPISAVFECSGSETTAFIRISRARLDGTPVVISTAGHDLTCAQYCRNNIEPTTGAQYCRNNIEPTTGAQRVCASFNFDGRETCYFPDDAASPAGTGELNEAPSANNFYYEKVCLPAISAHEACTYRSPS   130
ruler          1.........10........20........30........40........50........60........70........80........90.......100.......110.......120.......130

SEQ_ID_NO_46   FERARNTQLEGFVKKSVTVKNREHCLSACLKEKEFVCKSVNPHYENSLCELSVEDKRSKPTHVRMSEG-IDYYDNNCLSRQNRCGPSGGNLVFVKTNFEIRYYDHTQSVEAQESYCLQKCLDSLNTFCR   258
SEQ_ID_NO_18   FERARNTQLEGFVKKSVTVENREHCLSACLKEKEFVCKSVNFHYDTSLCELSVEDKRSKPTHVRMSEK-IDYYDNNCLSRQNRCGPSGGNLVFVKTNFEIRYYDHTQSVEAQESYCLQKCLDSLNTPCR   257
SEQ_ID_NO_4    FERTRNTQLEGFVKKSLQVTSREECLSTCLKESEFVCRSVNTNYENFMCELSTERSRSKPQNMRMSAAPVDYYDNNCLNRQNRCGESGGNLIPIKTQFEIHYYDHTQSMEAQSFCLQKCLDSLNTPCR   260
ruler          .........140.......150.......160.......170.......180.......190.......200.......210.......220.......230.......240.......250.......260

SEQ_ID_NO_46   SVEFNPKEKNCIVSDEDTFSRADQQGQVVGKDYYEPICVAADLSSSTCRQQAAFERFIGSSIEGEVVASAQGVTISDCISLCFQNLNCKSINYDRTASSCFIYAVGRQDANIKANPSMDYYEFNCESQPG   388
SEQ_ID_NO_18   SVEFNPKEKNCIVSDEDTFSRADQQGQVVGKDYYEPICVAADLSSSTCRQQAAFERFIGSSIEGEVVASAQGVTISDCISLCFQNLNCKSINYDRTASSCFIYAVGRQDANIKANPSMDYYEFNCESQPG   387
SEQ_ID_NO_4    SVEYSPSEKNCIVSDEDTYSRADQQGEVNNKDYYEPCVAATERFIGSAIEGTPVATAQQVTISDCISLCFQNLNCKSINYDRTQSTCYIYAVGRQESNVKNDASFDYYEF-----------------   383
ruler          .........270.......280.......290.......300.......310.......320.......330.......340.......350.......360.......370.......380.......390

SEQ_ID_NO_46   GMALCTNEGIRFIVNTKEPYTGAIYAAERFSTCSQVVENAKQISIFPPPTVTSDCGTVIRDGKMEALVVVSLDGVLPHQVTTEWDRFYRVSCDVSMDKMVKEGSVVVTTIYEASSQNTTVLDVATPPPV   518
SEQ_ID_NO_18   GMALCTNEGIRFIVNTKEPYTGAIYAAERFSTCSQVVENAKQISIFPPPTVSSDCGTVIRDGKMEALVVVSLDGVLPHQVTTEWDRFYRVSCDVSMDKMVKEGSVVVTTIYEASSQNTTVLDVATPPPV   517
SEQ_ID_NO_4    --------------------------------------------------------------------------------------------------------------------------------   383
ruler          .........400.......410.......420.......430.......440.......450.......460.......470.......480.......490.......500.......510.......520

SEQ_ID_NO_46   TAELQILNQLEEPLHKASIGDPLLLVITSEQAGPHNMVTECTATRVGGFGDTVPFTLIENGCPRYPALVGPVEQDFDKNRLKSDLRAFRLDGSYDVQIVCSIMFCAGPNGCPVSNCLDSGTNELFMSHG   648
SEQ_ID_NO_18   SAELQILNQLEEPLHKASIGDPLLLVITSEQAGPHNMVTECTATRVGGFGDTVPFTLIENGCPRYPALVGPVEQDFDKNRLKSDLRAFRLDGSYDVQIVCSIMFCAGPNGCPVSNCLDSGTNELFMSHG   647
SEQ_ID_NO_4    --------------------------------TIIDNGCPRYPALVGPVLQDFDKNRLKSEMKAFRLDGSYDIQIECSVMFCAGPMGCPPSNCLDSGTNELFASHG   457
ruler          .........530.......540.......550.......560.......570.......580.......590.......600.......610.......620.......630.......640.......650

SEQ_ID_NO_46   RKKRS-VDLEAGET-EERLSAIIRVPAKGEDEEBIEMG--NNTLMTSLAES----TDLLCIAEPFFVSSVVSLSVLCFALSAIIATWGCHAIHAKPTKQVAA   742
SEQ_ID_NO_18   RKKRS-ADLEAGET-EEKLSAIIRVPAKGEDEDEEMEMA--NNTMMTSMSDS----TELLCIAEPFFVSSVVSLSVLCFALSAIIAIWGCHSLHSKPVKQVAA   741
SEQ_ID_NO_4    RKKRSIVDFKNTTTSAETLSAIIRVLAAGEEELEVEFFYRNDTNFKYDSEENISAHNLYCMSEMWFVSGIVSMAMICLLLSVLIVMWGCHSLNQSSKLPM--   557
ruler          .........660.......670.......680.......690.......700.......710.......720.......730.......740.......750
```

NEMATODE PAN AND ZP RECEPTOR-LIKE SEQUENCES

RELATED APPLICATION INFORMATION

This application is a divisional of U.S. application Ser. No. 10/771,708, filed Feb. 4, 2004 now U.S. Pat. No. 6,936,693, which claims priority from U.S. provisional application Ser. No. 60/444,771, filed Feb. 4, 2003.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved to be very successful parasites of both plants and animals and are responsible for significant economic losses in agriculture and livestock and for morbidity and mortality in humans (Whitehead (1998) *Plant Nematode Control*, CAB International, New York).

Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) *California Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22-24; U.S. Pat. No. 6,048, 714). The few available broad-spectrum nematicides such as Telone (a mixture of 1,3-dichloropropene and chloropicrin) have significant restrictions on their use because of toxicological concerns (Carter (2001) *California Agriculture*, Vol. 55(3):12-18).

The macrocyclic lactones (e.g., avermectins and milbemycins) and delta-toxins from *Bacillus thuringiensis* (Bt) are nematicidal actives that in principle provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1-2):217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta toxins must be ingested to affect their target organ, the brush border of midgut epithelial cells (Marroquin et al. (2000) *Genetics*. 155(4):1693-1699). Consequently they are not anticipated to be effective against the dispersal, non-feeding, juvenile stages of plant parasitic nematodes in the field. Because juvenile stages only commence feeding when a susceptible host has been infected, nematicides may need to penetrate the plant cuticle to be effective. In addition, soil mobility of a relatively large 65-130 kDa protein—the size of typical Bt delta toxins—is expected to be poor and transgenic delivery in planta is likely to be constrained by the exclusion of large particles by the feeding tube of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Many plant species are known to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson. (1975) *J Nematol* 7(1):84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic. In many cases however, the active principle(s) for plant nematicidal activity has not been discovered and it remains difficult to derive commercially successful nematicidal products from these resistant plants or to transfer the resistance to agronomically important crops such as soybeans and cotton.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency leads to disease and stunted growth in livestock and companion animals. For instance, in cattle and dairy herds, a single untreated infection with the brown stomach worm can permanently restrict an animal's ability to convert feed into muscle mass or milk.

Two factors contribute to the need for novel anthelmintics and vaccines for control of parasitic nematodes of animals. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Some parasitic species have developed resistance to most of the anthelmintics (Geents et al. (1997) *Parasitology Today* 13:149-151; Prichard (1994) *Veterinary Parasitology* 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141-146). Secondly, there are some issues with toxicity for the major compounds currently available.

Infections by parasitic nematode worms result in substantial human mortality and morbidity, especially in tropical regions of Africa, Asia, and the Americas. The World Health Organization estimates 2.9 billion people are infected, and in some areas, 85% of the population carries worms. While mortality is rare in proportion to infections, morbidity is substantial and rivals diabetes and lung cancer in worldwide disability adjusted life year (DALY) measurements.

Examples of human parasitic nematodes include hookworms, filarial worms, and pinworms. Hookworms (1.3 billion infections) are the major cause of anemia in millions of children, resulting in growth retardation and impaired cognitive development. Filarial worm species invade the lymphatics, resulting in permanently swollen and deformed limbs (elephantiasis), and the eyes, causing African river blindness. The large gut roundworm *Ascaris lumbricoides* infects more than one billion people worldwide and causes malnutrition and obstructive bowel disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

Despite some advances in drug availability and public health infrastructure and the near elimination of one tropical nematode (the water-borne Guinea worm), most nematode diseases have remained intractable problems. Treatment of hookworm diseases with anthelmintic drugs, for instance, has not provided adequate control in regions of high incidence because rapid re-infection occurs after treatment. In fact, over the last 50 years, while nematode infection rates have fallen in the United States, Europe, and Japan, the overall number of infections worldwide has kept pace with the growing world population. Large scale initiatives by regional governments, the World Health Organization, foundations, and pharmaceutical companies are now underway attempting to control nematode infections with currently available tools, including three programs for control of Onchocerciasis (river blindness) in Africa and the Americas using ivermectin and vector control; The Global Alliance to Eliminate Lymphatic Filariasis using DEC, albendazole, and ivermectin; and the highly successful Guinea Worm Eradication Program.

The obvious missing weapons in the fight to control human parasitic nematodes are vaccines. Systematic vaccination against childhood diseases likes measles, mumps, polio, etc. has been among the most important and cost effective factors increasing lifespan and wellness in the developed world over the course of the 20th century. Expansion of these health gains into the developing world using existing vaccines, as the Gates Foundation is supporting, has the potential to capture immediate health gains. Such an approach could be equally effective for nematodes if such vaccines existed.

Research into vaccines for parasites, from malaria to nematode worms, has shown parasites to be challenging organisms to control by immunization since, unlike many viruses, antibody or cellular responses to most surface antigens fail to result in control. However, multiple vaccines for the control of nematode parasites in animals have shown efficacy either in testing or in veterinary use. For example, vaccination of dogs with irradiated hookworm larva results in high levels of protection to subsequent hookworm challenge. The same approach works for protection of gerbils from filarial worms. Unfortunately, parasitic nematodes cannot be grown in the quantities required for such a killed whole organism vaccination approach, with limited exceptions such as the Intervet niche product HuskVac™ for cattle lungworm. The greatest commercial success to date in immunization for veterinary parasites has come from the recombinant antigen vaccines TickGARD™ and Gavac™ for cattle which block the lifecycle of the ectoparasite *Boophilus microplus*, a bovine tick. Rather than utilizing a surface antigen, each of these vaccines targets an antigen, Bm86, expressed on the luminal surface of the tick mid-gut so that as the ectoparasite drinks the host's blood, it is exposed to antibodies that interfere with intestinal function. The same intestinal target approach has been successful in small-scale trials against the sheep parasitic nematode *Haemonchus*, a blood feeder similar to hookworms that can be controlled by vaccination with the purified parasite intestinal microvilli protein H11. Importantly, unlike a typical vaccine where the antigen is used to trigger a cascade of immune attack on the entire organism, the parasite intestinal approach utilizes an antibody response to "knockout" the function of a crucial nematode gene product, similar to the function of a drug.

Finding effective compounds and vaccines against parasitic nematodes has been complicated by the fact that the parasites have not been amenable to culturing in the laboratory. Parasitic nematodes are often obligate parasites (i.e., they can only complete their lifecycles in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.* 28(3):395-411). The genome of *C. elegans* has been completely sequenced and the nematode shares many general developmental and basic cellular processes with vertebrates (Ruvkin et al. (1998) *Science* 282:2033-41). This, together with its short generation time and ease of culturing, has made it a model system of choice for higher eukaryotes (Aboobaker et al. (2000) *Ann. Med.* 32:23-30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282:2028-33). The latter property is of particular relevance given that the avermectin class of drugs is thought to act at glutamate-gated chloride receptors and is highly selective for invertebrates (Martin (1997) *Vet. J.* 154:11-34).

A subset of the genes involved in nematode-specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode-specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500-10; Redmond et al. (2001) *Mol. Biochem. Parasitol.* 112:125-131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806-811; Montgomery et al. (1998) *Proc. Natl. Acad Sci USA* 95(26):15502-15507). Treatment of a nematode with double-stranded RNA of a selected gene triggers the destruction of expressed sequences transcribed from that gene, thus reducing or eliminating expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *Strongyloides stercoralis*, *Meloidogyne javanica*, *Heterodera glycines* and *Brugia malayi* PANZP proteins, e.g., PANZP1 and PANZP2. *S. stercoralis* is a nematode parasite that infects humans, primates, and dogs. It is one of the few nematodes that can multiply within its host and can multiply unchecked in immunosuppressed individuals. *M. javanica* is a Root Knot Nematode that causes substantial damage to several crops, including cotton, tobacco, pepper, and tomato. *H. glycines*, referred to as Soybean Cyst Nematode, is a major pest of soybean. *B. malayi*, is an arthropod vectored human parasite that is one of a causative agents of lymphatic filariasis, a disease that afflicts roughly 120 million people world wide. The PANZP proteins of the invention resemble the *Drosophila melanogaster* no-mechanoreceptor potential A (nompA) and Sp71 proteins. The PANZP proteins of the invention include Plasminogen Apple Nematode (PAN) and Zona Pellucida (ZP) domains.

The PANZP nucleic acids and polypeptides of the invention allow for the identification of nematode species. The nucleic acids and polypeptides of the invention also allow for the identification of compounds that bind to or alter the activity of PANZP polypeptides as well as compounds that alter the expression of PANZP polypeptides. Such compounds may provide a means for combating diseases and infestations caused by nematodes, particularly those caused by *S. stercoralis*, *M. javanica*, *H. glycines* and *B. malayi* (e.g., in mammals and plants). These nucleic acids and polypeptides also allow for the vaccination of animals and humans against nematode parasites. In addition, anti-nematode peptide or protein inhibitors and antibodies directed against nematode PAN and ZP containing proteins can be expressed in plants (plantibodies) to produce transgenic nematode resistance.

The invention is based, in part, on the identification of a cDNA encoding *S. stercoralis* PANZP1 (SEQ ID NO: 1). This 3750 nucleotide cDNA has a 3369 nucleotide open reading frame (SEQ ID NO: 5) encoding an 1122 amino acid polypeptide (SEQ ID NO: 3). The nucleotide and amino acid sequence of *S. stercoralis* PANZP1 is shown in FIGS. 1A-1C.

The invention is also based, in part, on the identification of a cDNA encoding *S. stercoralis* PANZP2 (SEQ ID NO: 2). This 1951 nucleotide cDNA has a 1674 nucleotide open reading frame (SEQ ID NO: 6) encoding a 557 amino acid polypeptide (SEQ ID NO: 4). The nucleotide and amino acid sequence of *S. stercoralis* PANZP2 is shown in FIGS. 2A-2B.

The invention is also based, in part, on the identification of a cDNA encoding *M. javanica* PANZP1 (SEQ ID NO: 7). This 3848 nucleotide cDNA has a 3633 nucleotide open reading frame (SEQ ID NO: 13) encoding a 1210 amino acid polypeptide (SEQ ID NO: 10). The nucleotide and amino acid sequence of *M. javanica* PANZP2 is shown in FIGS. 3A-3C.

The invention is also based, in part, on the identification of a partial cDNA fragment encoding *H. glycines* PANZP1 (SEQ ID NO: 8). This 752 nucleotide partial cDNA fragment has a 750 nucleotide open reading frame (SEQ ID NO: 14) encoding a 250 amino acid polypeptide (SEQ ID NO: 11). The nucleotide and amino acid sequence of *H. glycines* PANZP2 is shown in FIG. 4.

The invention is also based, in part, on the identification of a partial cDNA fragment encoding *B. malayi* PANZP1 (SEQ ID NO: 9). This 2808 nucleotide partial cDNA fragment has a 2643 nucleotide open reading frame (SEQ ID NO: 15) encoding a 881 amino acid polypeptide (SEQ ID NO: 12). The nucleotide and amino acid sequence of *B. malayi* PANZP2 is shown in FIGS. 5A-5B.

In one aspect, the invention features novel nematode PAN and ZP containing receptor-like polypeptides. Such polypeptides include purified polypeptides having the amino acid sequences set forth in SEQ ID NO: 3, 4, 10, 11 and/or 12. Also included are polypeptides having an amino acid sequence that is at least about 80%, 85%, 90%, 95%, or 98% identical to SEQ ID NO: 3, 4, 10, 11 and/or 12 as well as polypeptides having a sequence that differs from that of SEQ ID NO: 3, 4, 10, 11 and/or 12 at 20, 15, 10, 9, 8, 7, 6, 5, 4, 3, 2, or 1 residues (amino acids). The purified polypeptides can be encoded by a nematode gene, e.g., a nematode-gene other than a *C. elegans* gene. For example, the purified polypeptide has a sequence other than SEQ ID NO: 16, 17, and 18 (*C. elegans* PANZP1 and PANZP2 proteins). The purified polypeptides can further include a heterologous amino acid sequence, e.g., an amino-terminal or carboxy-terminal sequence. Also featured are purified polypeptide fragments of the aforementioned PANZP polypeptides, e.g., a fragment of at least about 20, 30, 40, 50, 75, 85, 104, 106, 113 150, 200, 250 amino acids. Non-limiting examples of such fragments include: fragments from about amino acid 20 to 110 and 100 to 210 of SEQ ID NO: 3, 4, 10, 11 and/or 12 and 200 to 310, 300 to 400 and 400 to 500 of SEQ ID NO: 3, 4, 10 and/or 12. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above. Certain PANZP polypeptides comprise a sequence of 600, 700, 800, 900, 1000, 1100, 1200, 1300 amino acids or fewer. The invention also features polypeptides comprising, consisting essentially of or consisting of the aforementioned polypeptides. Also within the invention are polypeptides, including immunogenic polypeptides comprising (or consisting of or consisting essentially of) a PAN or ZP domain of SEQ ID NO: 3, 4, 10, 11, or 12, e.g., a PAN or ZP domain listed in Table 3.

In another aspect, the invention features novel isolated nucleic acid molecules encoding nematode PAN and ZP containing receptor-like polypeptides. Such isolated nucleic acid molecules include nucleic acids having the nucleotide sequence set forth in SEQ ID NO: 1, 2, 7, 8 or SEQ ID NO: 9. Also included are isolated nucleic acid molecules having the same sequence as or encoding the same polypeptide as a nematode PAN and ZP containing receptor-like gene (other than a *C. elegans* PANZP genes).

Also featured are: 1) isolated nucleic acid molecules having a strand that hybridizes under low stringency conditions to a single stranded probe of the sequences of SEQ ID NO: 1, 2, 7, 8, 9, or their complements and, optionally, encodes polypeptides of between 500 and 1300 amino acids; 2) isolated nucleic acid molecules having a strand that hybridizes under high stringency conditions to a single stranded probe of the sequence of SEQ ID NO: 1, 2, 7, 8, 9 or their complements and, optionally, encodes polypeptides of between 500 and 1300 amino acids; 3) isolated nucleic acid fragments of a PANZP nucleic acid molecule, e.g., a fragment of SEQ ID NO:1, 2, 7, 8 or 9 that is about 50, 100, 150, 200, 250, 300, 350, 400, 450, 500, 1000, 1500, 2000, 2500, 3000 and 3500 or more nucleotides in length or ranges between such lengths; and 4) oligonucleotides that are complementary to a PANZP nucleic acid molecule or a PANZP nucleic acid complement, e.g., an oligonucleotide or probe of about 10, 15, 18, 20, 22, 24, 28, 30, 35, 40, 50, 60, 70, 80, or more nucleotides in length. Exemplary oligonucleotides are oligonucleotides which anneal to a site located between nucleotides about 1 to 96, 1 to 180, 1 to 270, 1 to 324, 96 to 324, 96 to 345, 324 to 345, 324 to 603, 345 to 603, 345 to 618, 603 to 618, 603 to 752 of SEQ ID NO: 1, 2, 7, 8 or 9; 618 to 1197, 906 to 1524, 1524 to 1951 of SEQ ID NO: 1, 2, 7 or 9; 1197 to 2124, 1524 to 2808 of SEQ ID NO: 1, 7, or 9; 1197 to 2124, 1524 to 3750 of SEQ ID NO: 1 or 7; 1197 to 2124, 1524 to 3848 of SEQ ID NO: 7. Nucleic acid fragments include the following non-limiting examples: nucleotides about 1 to 200 of SEQ ID NO: 1, 2, 7, 8, or 9, 100 to 300, 200 to 400, 300 to 500, 400 to 700, 500 to 800, 600 to 1200, 1200 to 1951 of SEQ ID NO: 1, 2, 7, or 9, 1200 to 2808 of SEQ ID NO: 1, 7 or 9; 1200 to 3750 of SEQ ID NO: 1 or 7, 1200 to 3848 of SEQ ID NO: 7. Also within the invention are nucleic acid molecules that hybridize under stringent conditions to nucleic acid molecule comprising SEQ ID NO: 1, 2, 7, 8 or 9 and comprise 4000, 3000, 2000, 1000 or fewer nucleotides. The isolated nucleic acid can further include a heterologous promoter or other sequences required for transcription or translation of the nucleic acid molecule in a cell, e.g., a mammalian or eukaryotic or prokaryotic cell, operably linked to the PANZP nucleic acid molecule. The isolated nucleic acid molecule can encode a polypeptide having PAN and ZP containing receptor-like function.

A molecule featured herein can be from a nematode of the class Araeolaimida, Ascaridida, Chromadorida, Desmodorida, Diplogasterida, Monhysterida, Mononchida, Oxyurida, Rhigonematida, Spirurida, Enoplia, Desmoscolecidae, Rhabditida, or Tylenchida. Alternatively, the molecule can be from a species of the class Rhabditida, particularly a species other than *C. elegans*.

In another aspect, the invention features a vector, e.g., a vector containing an aforementioned nucleic acid. The vector can further include one or more regulatory elements, e.g., a heterologous promoter or elements required for translation. The regulatory elements for directing transcription and translation elements can be suitable for expression in bacteria, plants, animals, or insects. The regulatory elements can be operably linked to the PAN and ZP containing receptor-like nucleic acid molecules in order to express a PANZP nucleic acid molecule. In yet another aspect, the invention features a transgenic cell or transgenic organism having in its genome a transgene containing an aforementioned PANZP nucleic acid molecule and a heterologous nucleic acid, e.g., a heterologous promoter.

In still another aspect, the invention features an antibody, e.g., an antibody, antibody fragment, or derivative thereof that binds specifically to an aforementioned polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from a PANZP polypeptide. The antibody need not include domain that trigger an immune response.

In another aspect, the invention features a method of screening for a compound that binds to a nematode PANZP polypeptide, e.g., an aforementioned polypeptide. The method includes providing the nematode polypeptide; contacting a test compound to the polypeptide; and detecting binding of the test compound to the nematode polypeptide. In one embodiment, the method further includes contacting the test compound to a mammalian PAN or ZP domain-containing polypeptide and detecting binding of the test compound to the mammalian PAN or ZP polypeptide in order to identify compounds with selective binding activity. A test compound that binds the nematode PANZP polypeptide with at least 2-fold, 5-fold, 10-fold, 20-fold, 50-fold, or 100-fold affinity greater relative to its affinity for the mammalian (e.g., a human) PAN or ZP polypeptide can be identified.

The invention also features methods for identifying compounds that alter (increases or decreases) the association of a nematode PAN and ZP containing domain receptor-like polypeptide with a substrate such as a small molecule or protein. The method includes contacting the test compound to the nematode PANZP polypeptide; and detecting a decrease in the binding of the PANZP protein to the substrate. A decrease in the level of PANZP polypeptide binding to the substrate relative to the PANZP polypeptide binding to the substrate in the absence of the test compound is an indication that the test compound is an inhibitor of the PANZP activity. The inhibitor can be a direct competitor of the binding or an allosteric inhibitor that prevents binding of the PANZP polypeptide to other molecules or proteins. Such inhibitory compounds are potential selective agents for reducing the viability of a nematode expressing a PANZP polypeptide, e.g., S. stercoralis, M. javanica, H. glycines and B. malayi. These methods can also include contacting the compound with a vertebrate PAN containing protein (e.g., human Factor XI) or a vertebrate ZP containing polypeptide (e.g., human uromodulin) and detecting binding of the compounds to the proteins. A compound that binds to the nematode PAN and ZP containing receptor-like polypeptides to a greater extent than it binds to vertebrate PAN or ZP polypeptides could be useful as a selective inhibitor of the nematode polypeptide. A desirable compound can exhibit 2-fold, 5-fold, 10-fold, 20-fold, 50-fold, 100-fold or greater selective affinity against the nematode polypeptide.

Another featured method is a method of screening for a compound that alters (increases or decreases) the binding of a PAN and ZP containing receptor-like polypeptide to a small molecule or protein substrate or alters the regulation of other polypeptides by the PANZP protein. The method includes providing the PANZP polypeptide; contacting a test compound to the PANZP polypeptide; and detecting an alteration of the binding activity or the activity of polypeptides regulated by the PANZP protein, wherein a change in binding activity of the PANZP polypeptides to its substrates or a change in the activity of other polypeptides downstream of the PANZP protein binding activity relative to the binding activity of the PANZP protein or the activity of downstream polypeptides in the absence of the test compound is an indication that the test compound alters the activity of the PANZP polypeptide(s). The method can further include contacting the test compound to a vertebrate PAN containing protein (e.g., human Factor XI) or a vertebrate ZP containing polypeptide (e.g., human uromodulin) and detecting binding of the compounds to the proteins and measuring the effects of the compounds on the activities of the vertebrate proteins. A test compound that alters the activity of the nematode PANZP polypeptide at a given concentration and that does not substantially alter the activity of the vertebrate PAN or ZP containing polypeptide or downstream polypeptides at the given concentration can be identified. An additional method includes screening for both binding to a PANZP polypeptide and for an alteration in the binding activity of a PANZP polypeptide. Yet another featured method is a method of screening for a compound that alters (increases or decreases) the viability or fitness of a transgenic cell or organism or nematode. The transgenic cell or organism has a transgene that expresses a PAN and ZP containing receptor-like polypeptide. The method includes contacting a test compound to the transgenic cell or organism and detecting changes in the viability or fitness of the transgenic cell or organism. This alteration in viability or fitness can be measured relative to an otherwise identical cell or organism that does not harbor the transgene.

Also featured is a method of screening for a compound that alters the expression of a nematode nucleic acid encoding a PAN and ZP containing receptor-like polypeptide, e.g., a nucleic acid encoding a S. stercoralis, M. javanica, H. glycines or B. malayi PANZP polypeptide. The method includes contacting a cell, e.g., a nematode cell, with a test compound and detecting expression of a nematode nucleic acid encoding a PANZP polypeptide, e.g., by hybridization to a probe complementary to the nematode nucleic acid encoding a PANZP polypeptide or by contacting polypeptides isolated from the cell with a compound, e.g., antibody that binds a PANZP polypeptide. Compounds identified by the method are also within the scope of the invention.

In yet another aspect, the invention features a method of treating a disorder (e.g., an infection) caused by a nematode, e.g., S. stercoralis, M. javanica, H. glycines or B. malayi in a subject, e.g., a host plant or host animal. The method includes administering to the subject an effective amount of an inhibitor of a PANZP polypeptide activity or an inhibitor of expression of a PANZP polypeptide. Non-limiting examples of such inhibitors include: an antisense nucleic acid (or PNA) to a PANZP nucleic acid, a double-stranded RNA inhibitor capable of triggering RNA interference, an antibody to a PANZP polypeptide, an inhibitory peptide or protein, or a small molecule identified as a PANZP polypeptide inhibitor by a method described herein.

Also featured is a method of preventing or treating a disorder (e.g., an infection) caused by a nematode (e.g., S. stercoralis or B. malayi) in a host animal by vaccinating the animal with nematode PANZP protein or nucleic acid (e.g., a PANZP DNA vaccine) or both. Also featured is a method of preventing infection of a plant host by a nematode (e.g., M. javanica or H. glycines) by expressing an antisense RNA or double-stranded RNA to the nematode PANZP nucleic acid or by expressing antibodies or other proteins which interfere with the function of the nematode PANZP protein.

In yet another aspect, the invention features methods for the production of nematode resistant transgenic plants by obtaining specific antibodies to nematode PANZP proteins, deriving the nucleic acid sequences that code for these antibodies and expressing these nucleic acids in plants under the control of appropriate promoters (e.g., constitutive or inducible, non-tissue specific, root specific, feeding site specific) and with other suitable control sequences (e.g., enhancers, introns, UTRs, terminators) to produce antibodies to the PANZP proteins in plants (plantibodies).

Also featured in this invention is a method of producing nematode resistant transgenic plants by the expression of nucleic acids coding for PANZP nematode proteins or portions of PANZP nematode proteins that can produce PANZP peptides or polypeptides capable of dominant negative interaction with endogenous nematode PAN and ZP containing receptor-like proteins upon ingestion by plant parasitic nematodes.

Also within the scope of this invention is the use of selection techniques like phage display or polysome display to generate peptides or proteins which bind to and inhibit the function of nematode PANZP proteins.

A "purified polypeptide", as used herein, refers to a polypeptide that has been separated from other proteins, lipids, and nucleic acids with which it is naturally associated. The polypeptide can constitute at least 10, 20, 50 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically; as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A percent identity for any subject nucleic acid or amino acid sequence (e.g., any of the PANZP polypeptides described herein) relative to another "target" nucleic acid or amino acid sequence can be determined as follows. First, a target nucleic acid or amino acid sequence of the invention can be compared and aligned to a subject nucleic acid or amino acid sequence, using the BLAST 2 Sequences (Bl2seq) program from the stand-alone version of BLASTZ containing BLASTN and BLASTP (e.g., version 2.0.14). The stand-alone version of BLASTZ can be obtained at or www.ncbi.nlm.nih.gov>. Instructions explaining how to use BLASTZ, and specifically the Bl2seq program, can be found in the 'readme' file accompanying BLASTZ. The programs also are described in detail by Karlin et al. (1990) *Proc. Natl. Acad. Sci.* 87:2264; Karlin et al. (1990) *Proc. Natl. Acad. Sci.* 90:5873; and Altschul et al. (1997) *Nucl. Acids Res.* 25:3389.

Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions, of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., α-helices, β-sheets, and loops).

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the Bl2seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180÷200×100=90).

It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The identification of conserved regions in a template, or subject, polypeptide can facilitate homologous polypeptide sequence analysis. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at http://www.sanger.ac.uk/Pfam/ and http://genome.wustl.edu/Pfam/. A description of the information included at the Pfam database is described in Sonnhammer et al. (1998) *Nucl. Acids Res.* 26: 320-322; Sonnhammer et al. (1997) *Proteins* 28:405-420; and Bateman et al. (1999) *Nucl. Acids Res.* 27:260-262. From the Pfam database, consensus sequences of protein motifs and domains can be aligned with the template polypeptide sequence to determine conserved region(s).

As used herein, the term "transgene" means a nucleic acid sequence (encoding, e.g., one or more subject polypeptides), which is partly or entirely heterologous, i.e., foreign, to the transgenic plant, animal, or cell into which it is introduced, or, is homologous to an endogenous gene of the transgenic plant, animal, or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which affects expression of the selected DNA sequence in specific cells of a tissue, such as a leaf, root, or stem.

As used herein the terms "hybridizes under stringent conditions" and "hybridizes under high stringency conditions" refer to conditions for hybridization in 6× sodium chloride/sodium citrate (SSC) buffer at about 45° C., followed by two washes in 0.2×SSC buffer, 0.1% SDS at 60° C. or 65° C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "anthelmintic activity" is an agent, which when tested, has measurable nematode-killing activity or results in infertility or sterility in the nematodes such that unviable or no offspring result. In the assay, the agent is combined with nematodes, e.g., in a well of microtiter dish having agar media or in the soil containing the agent. Staged adult nematodes are placed on the media. The time of survival, viability or number of offspring, and/or the movement of the nematodes are measured. An agent with "anthelmintic activity" reduces the survival time of adult nematodes relative to unexposed similarly staged adults, e.g., by about 20%, 40%, 60%, 80%, or more. In the alternative, an agent with "anthelmintic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently linked to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly a PANZP activity. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

In part, the nematode PAN and ZP containing receptor-like proteins and nucleic acids described herein are novel targets for anti-nematode vaccines, pesticides, and drugs. These polypeptides are also useful for the creation of nematode resistant transgenic plants. Inhibition of these molecules can provide means of inhibiting nematode metabolism and/or the nematode life-cycle.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1C depict the cDNA sequence of a *S. stercoralis* PAN and ZP containing receptor-like protein 1 (PANZP1) (SEQ ID NO: 1), its corresponding encoded amino acid sequence (SEQ ID NO: 3), and its open reading frame (SEQ ID NO: 5).

FIGS. 2A-2B depict the cDNA sequence of a *S. stercoralis* PAN and ZP containing receptor-like protein 2 (PANZP2) (SEQ ID NO: 2), its corresponding encoded amino acid sequence (SEQ ID NO: 4), and its open reading frame (SEQ ID NO: 6).

FIGS. 3A-3C depict the cDNA sequence of a *M. javanica* PAN and ZP containing receptor-like protein 1 (PANZP1) (SEQ ID NO: 7), its corresponding encoded amino acid sequence (SEQ ID NO: 10), and its open reading frame (SEQ ID NO: 13).

FIG. 4 depicts the partial cDNA fragment of the sequence of a *H. glycines* PAN and ZP containing receptor-like protein 1 (PANZP1) (SEQ ID NO: 8), its corresponding encoded amino acid sequence (SEQ ID NO: 11), and its open reading frame (SEQ ID NO: 14).

FIGS. 5A-5B depict the partial cDNA fragment of a sequence of a *B. malayi* PAN and ZP containing receptor-like protein 1 (PANZP1) (SEQ ID NO: 9), its corresponding encoded amino acid sequence (SEQ ID NO: 12), and its open reading frame (SEQ ID NO: 15).

FIG. 7 is an alignment of the sequences of *S. stercoralis, M. javanica, H. glycines* and *B. malayi* PAN and ZP containing receptor-like polypeptide proteins and fragments (PANZP1; SEQ ID NO: 3, 10, 11, 12), *C. elegans* PANZP1 polypeptides (SEQ ID NO: 16 and 17) and *C. briggsae* PANZP1 polypeptide (SEQ ID NO: 45).

FIG. 8 is an alignment of the sequences of *S. stercoralis* PAN and ZP containing receptor-like polypeptide protein 2 (PANZP2; SEQ ID NO: 4), *C. elegans* PANZP2 polypeptide (SEQ ID NO: 18) and *C. briggsae* PANZP2 (SEQ ID NO: 46).

DETAILED DESCRIPTION

Figure 6:
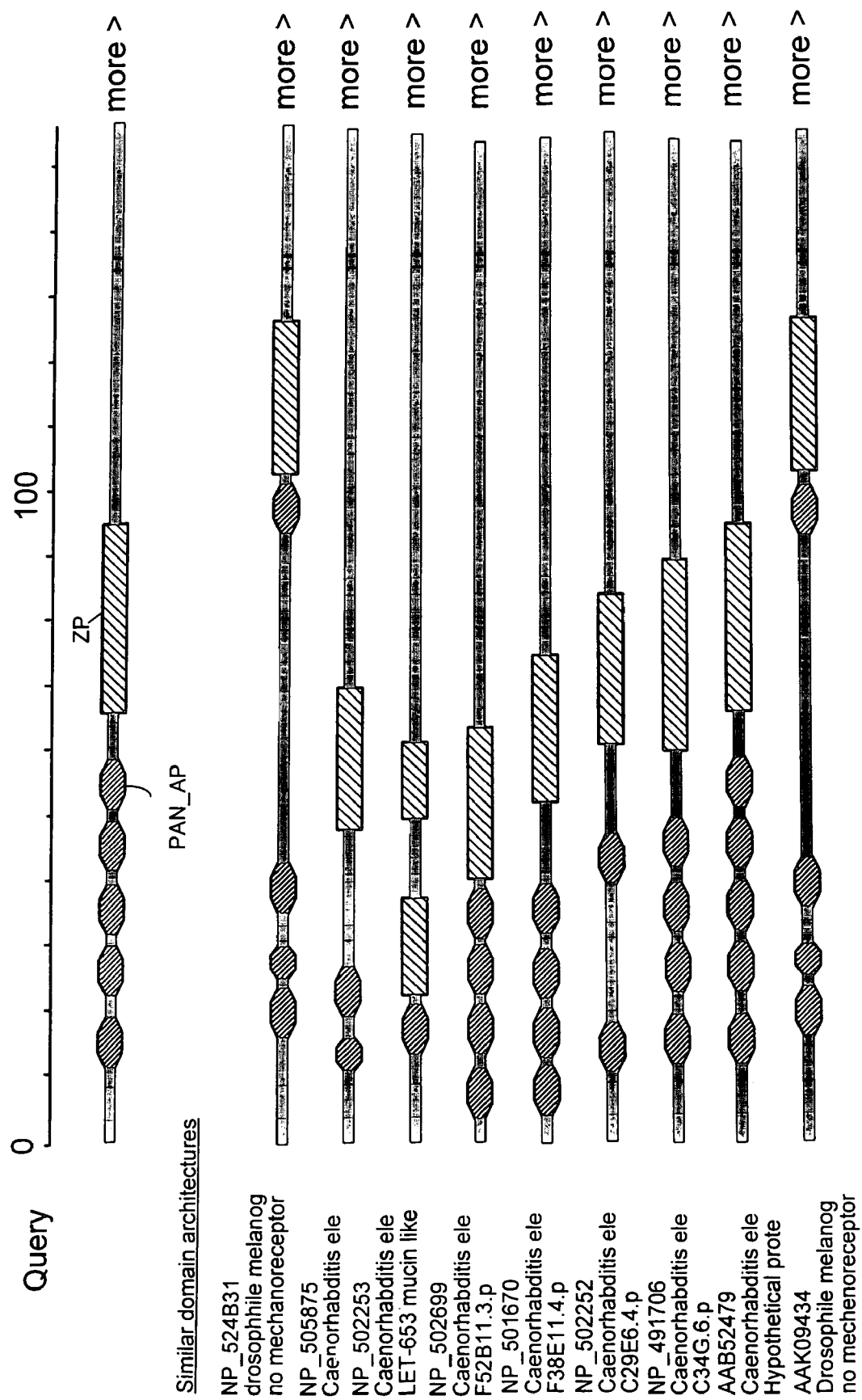
FIG. 6 depicts an alignment showing schematic depictions of a number of PAN and ZP domain containing proteins including: *D. melanogaster* GENBANK® Accession No. NP_524831, *C. elegans* GENBANK® Accession No. NP_505875, *C. elegans* GENBANK® Accession No. NP_502253, *C. elegans* GENBANK® Accession No. NP_505874, *C. elegans* GENBANK® Accession No. NP_502699, *C. elegans* GENBANK® Accession No. NP_501670, *C. elegans* GENBANK® Accession No. NP_502252, *C. elegans* GENBANK® Accession No. NP_491706, *C. elegans* GENBANK® Accession No. AAB52479, *D. melanogaster* GENBANK® Accession No. AAK09434.

An important step toward the development of new anthelmintic agents is the identification of nematode-specific gene products that can serve as targets for inhibitory peptides and proteins (e.g., antibodies) and antiparasitic chemicals. An ideal target gene would be essential for nematode viability, such that interference with the target would result in the arrest of parasite growth and reproduction. In addition, the protein product of the target gene should be accessible to drugs, small chemicals or antibodies. Finally, the ideal target should be specific to nematodes and not closely related to any gene in plants or animals. Based on these criteria, we have identified two *C. elegans* genes, PANZP1 (C34G6.6) and PANZP2 (F52B11.3), as important targets for the development of vaccines, small molecule anthelmintic chemicals for both human and animal parasites and nematicides for plant parasitic nematode control. In addition, inhibitors of PANZP1 and PANZP2 could be used in the design of transgenic plants producing anti-nematode peptides, small natural products with nematicidal activity, and antibodies (plantibodies) directed against endogenous nematode targets.

PANZP1 and PANZP2 are predicted to be secreted, membrane-bound proteins. Close homologs of the *C. elegans* PANZP1 genes were identified in an intestinal library from *Ascaris suum*, suggesting that these genes are expressed in the nematode gastrointestinal system. The presence of C-terminal transmembrane domains suggests that the proteins are anchored in the membrane. Domain analysis of the PANZP1 and PANZP2 sequences using TargetP (a secretion prediction tool available on the internet at cbs.dtu.dk/services/TargetP/), PFAM (a domain analysis tool available on the internet at pfam.wustl.edu;) and TMHMM (a transmembrane domain prediction tool available on the internet at cbs.dtu.dk/services/TMHMM) indicates the presence of a secretion leader, several Plasminogen Apple Nematode (PAN) domains and a single C-terminal Zona Pellucida (ZP) domain before the transmembrane helix which is followed by a short C-terminal tail. The domain architecture of PANZP1 and PANZP2 is illustrated at the top of FIG. 6 along with the domain structure of a number of *C. elegans* and *D. melanogaster* PAN and ZP domain-containing proteins. The *C. elegans* genome contains several predicted proteins with a similar modular arrangement to PANZP1 and PANZP2. Of these, two (C34G6.6a and C34G6.6b) appear to be isoforms of the same gene (C34G6.6[p] is an older gene prediction), but the others appear to represent unique loci. Additionally, homologs containing the same domain layout are found in *Drosophila melanogaster* and the *Anopheles gambiae* genomes.

PAN domains and the related PAN_AP domains are typically 80-90 amino acids in length and are defined by a characteristic pattern of six cysteine residues and conserved hydrophobic residues. The cysteine residues form three highly conserved disulfide bonds linking the first and sixth, second and fifth, and third and fourth cysteine residues present in each repeat (McMullen et al. (1991) *Biochemistry*, 30(8):2050-2056; Brown et al. (2001) *FEBS Lett.* 497(1)31-38). The conserved disulfide linkages give the PAN domains a characteristic apple-like globular structure. PAN domains were originally referred to as "Apple" domains based on this characteristic structure.

PAN and PAN_AP domains have been extensively studied in the mammalian blood coagulation proteins Factor XI (FXI), plasma pre-kallikrein (PK), and plasminogen. The specific involvement of the apple (or PAN) domains in protein-protein interactions that mediate blood clotting has been demonstrated (Baglia et al. (1995) *J. Biol. Chem.* 270(12):6734-6740; Sun & Gailani (1996) *J. Biol. Chem.* 271(46):29023-29028; Ho et al. (2000) *Biochemistry*, 39(2): 316-323; Renne et al. (2002) *J. Biol. Chem.* 277(7):4892-4899). PAN domains are also thought to mediate protein-protein or protein-carbohydrate interactions in adhesive proteins that are secreted by apicomplexan parasites, single-celled eukaryotic organisms that invade target host cells in order to replicate. PAN domain-containing proteins are secreted by these organisms and are thought to play a role in the recognition and attachment of the parasite to host cells (Brown et al. (2001) *FEBS Lett.* 497(1)31-38; Brecht et al. (2001) *J. Biol. Chem.* 276(6):4119-4127).

The *C. elegans* genome contains at least 20 predicted proteins that contain one or more PAN domains. Although the level of sequence percent identity is low among the PAN domain family members, the pattern of conserved cysteines and hydrophobic residues establishes the three dimensional structure that is characteristic of the domain (Tordai et al. (1999) *FEBS Lett.* 461(1-2):63-67). The possibility for a high degree of sequence diversity within the family enables the domain to mediate a large number of protein-protein interactions.

In addition to N-terminal PAN domains, PANZP1 and PANZP2 contain a C-terminal ZP (zona pellucida) domain. Many eukaryotic proteins contain ZP domains, including the mammalian sperm cell receptors ZP2 and ZP3 and other large modular transmembrane proteins such as the major urinary protein uromodulin (Tamm-Horsfall protein or THP), human alpha-tectorin, and *Drosophila* nompA. In all examples found to date, the ZP domain occurs at the C-terminus of the protein.

The ZP domain occurs in proteins that are known to polymerize to form filaments and matrices. For example, THP, the most abundant urinary protein, is a secreted protein that polymerizes into filaments that are thought to be responsible for the water-impermeability of the thick ascending limb of the loop of Henle (Kokot & Dulawa (2000) *Nephron*, 85(2):97-102). Mammalian sperm receptors ZP2 and ZP3 are secreted by oocytes and polymerize to form the thick extracellular matrix, the zona pellucida, which surrounds oocytes. Another ZP domain-containing protein, alpha-tectorin, is the primary non-collagenous component of the cochlear tectorial membrane, an extracellular matrix that is important in the transduction of sound into neuronal impulses. The requirement of the ZP domain for the assembly of THP and for ZP2 and ZP3 proteins into supramolecular filaments was recently demonstrated (Jovine et al. (2002) *Nat. Cell. Biol.* 4(6):457-461).

The *Drosophila* nompA gene has a similar domain arrangement to PANZP1 and PANZP2, and while overall sequence percent identity between the insect and nematode proteins is low, the nompA protein (along with Sp71) is one of the most closely related non-nematode sequences by BLAST analysis to (the *C. elegans* PAN-ZP containing proteins). Like PANZP1 and PANZP2, the *Drosophila* nompA (no-mechanoreceptor potential A) is a transmembrane protein with a large, modular extracellular segment that includes the PAN and ZP domains. NompA is localized in an extracellular matrix that is responsible for the transduction of mechanical stimuli to sensory processes in the peripheral nervous system (Chung et al. (2001) *Neuron* 29(2):415-428). Mutations in the no-mechanoreceptor-potential A (nompA) gene eliminate transduction in *Drosophila* mechanosensory organs by disrupting contacts between neuronal sensory endings and cuticular structures.

PANZP1 and PANZP2 are essential for nematode viability. RNAi-generated mutations of PANZP1 and PANZP2 result in larval arrest at the L2 stage. A related *C. elegans* PAN-domain containing protein, LET-653 (C29E6.1) has also been shown to be an essential gene (Clark & Baille (1992) *Mol. Gen. Genet.* 232(1):97-105). Mutations in the let-653 gene are lethal and are associated with the appearance of large vacuoles that suggest a dysfunction of the secretory/excretory apparatus (Jones & Baille (1995) *Mol. Gen. Genet.* 248(6):719-726). LET-653 has two N-terminal PAN domains and a weakly predicted C-terminal ZP domain that contains a region of low-complexity sequence. The function of LET-653 is unknown, but it has been speculated that it may be functionally similar to the mammalian ZP-domain containing GP2 protein (Tordai et al. (1999) *FEBS Lett.* 461(1-2):63-67; Wong & Lowe, (1996) *Gene*, 171(2): 311-312). GP2 plays an important role in the secretion of pancreatic digestive enzymes. GP2 is the major glycoprotein component of the zymogen granule membrane. Proteolytic processing of GP2 and its release from the zymogen granule membrane occur as part of the normal process of zymogen granule secretion in the pancreas (Fritz et al. (2002) *Pancreas*, 24(4):336-343).

Proteins such as PANZP1 and PANZP2 that are localized in the nematode gut are especially attractive targets for the development of vaccines. Although gut-localized proteins are accessible to antibodies, they are normally inaccessible to host immune surveillance that is required to mount an immune response. Nevertheless, these so-called "hidden antigens", when purified, can be used to stimulate highly effective antibody responses in animals, especially against blood-feeding nematodes (Munn (1997) *Int. J. Parasit.* 27(4):359-366); Newton & Munn (1999) *Parasitology Today*, 15:116-122).

The structural features of the PANZP1 and PANZP2 suggest possible strategies for the production of antibodies and for the rational design of peptide inhibitors that could interfere with the protein-protein interactions mediated by the PAN and ZP domain portions of the molecule. It has been shown in studies with blood coagulation factors that antibodies and peptides that compete for binding to PAN domains disrupt the normal protein-protein interactions, and prevent blood coagulation (Baglia et al. (1995) *J. Biol. Chem.* 270(12):6734-6740; Sun & Gailani (1996) *J. Biol. Chem.* 271(46):29023-29028; Renne et al. (2002) *J. Biol. Chem.* 277(7):4892-4899). Recombinant proteins containing the PAN domain only have been shown to assume the proper conformation, suggesting that it would be possible to purify amounts of PAN domains that could be used for the production of antibodies (Baglia & Walsh (1996) *J. Biol. Chem.* 271(7): 3652-3658; Baglia et al. (2000) *J. Biol. Chem* 275(41):31954-31962). It has also been demonstrated that synthetic peptides that are designed from conformationally constrained portions of the PAN domain sequence (i.e., peptides which have at least one of the conserved disulfide linkages) are effective inhibitors of the normal protein-protein interaction carried out by the whole protein. Nematode resistant transgenic plants may be created by the production of plantibodies capable of interfering with the function of PANZP1 or PANZP2 or the expression in plants of peptides or individual PAN or ZP domains that can interfere with the normal functioning of nematode PANZP1 or PANZP2 in dominant negative fashion. The small size of peptides or individual domains may be an advantage for applications against certain plant parasitic nematodes, which appear to have size exclusion constraints for oral uptake.

The present invention provides nucleic acid sequences from nematodes encoding PAN and ZP containing receptor-like polypeptides. The *S. stercoralis* nucleic acid molecule (SEQ ID NO: 1) and the encoded PANZP1 (SEQ ID NO: 3) are depicted in FIGS. 1A-1C. The *S. stercoralis* nucleic acid molecule (SEQ ID NO: 2) and the encoded PANZP2 (SEQ ID NO: 4) are depicted in FIGS. 2A-2B. The *M. javanica* nucleic acid molecule (SEQ ID NO: 7) and the encoded PANZP1 (SEQ ID NO: 10) are depicted in FIGS. 3A-3C. The partial *H. glycines* nucleic acid molecule (SEQ ID NO: 8) and the encoded PANZP1 (SEQ ID NO: 11) are depicted in FIG. 4. The partial *B. malayi* nucleic acid molecule (SEQ ID NO: 9) and the encoded PANZP1 (SEQ ID NO: 12) are depicted in FIGS. 5A-5B. Certain sequence information for the PANZP1 and PANZP2 genes described herein is summarized in Table 1, below.

TABLE 1

| Species | CDNA | ORF | Polypeptide | Figure |
| --- | --- | --- | --- | --- |
| S. stercoralis | SEQ ID NO: 1 | SEQ ID NO: 5 | SEQ ID NO: 3 | FIGS. 1A–1C |
| S. stercoralis | SEQ ID NO: 2 | SEQ ID NO: 6 | SEQ ID NO: 4 | FIGS. 2A–2B |
| M. javanica | SEQ ID NO: 7 | SEQ ID NO: 13 | SEQ ID NO: 10 | FIGS. 3A–3C |
| H. glycines | SEQ ID NO: 8 | SEQ ID NO: 14 | SEQ ID NO: 11 | FIG. 4 |
| B. malayi | SEQ ID NO: 9 | SEQ ID NO: 15 | SEQ ID NO: 12 | FIGS. 5A–5B |

The invention is based, in part, on the discovery of PANZP sequences from *S. stercoralis*, *M. javanica*, *H. glycines*, and *B. malayi*. The following examples are, therefore, to be construed as merely illustrative, and not limitative of the remainder of the disclosure in any way whatsoever. All of the publications cited herein are hereby incorporated by reference in their entirety.

EXAMPLES

A TBLASTN query with the *C. elegans* genes C34G6.6 (gi|17505859|ref|NP_491706.1|; PANZP1) and F52B11.3 (gi|17540572|ref|NP_502699.1|; PANZP2) identified multiple expressed sequence tags (ESTs are short nucleic acid fragment sequences from single sequencing reads) in dbest that are predicted to encode a portion of PANZP enzymes in multiple nematode species.

PANZP ESTs identified as similar to *C. elegans* C34G6.6 (*C. elegans* PANZP1) include but are not limited to *Brugia malayi* (gi|2199168|gb|AA471404.1|AA471404); *Pristionchus pacificus* (gi|15339536|gb|BI500192.1|BI500192), *Strongyloides stercoralis* (gi|9830619|gb|BE579677.1|BE579677); *Ascaris summ* (gi|15785830|gb|BI782938.1|BI782938); *Meloidogyne javanica* (gi|15766417|gb|BI744615.1|BI744615); *Strongyloides ratti* (gi|14494496|gb|BI073876.1|BI073876); and *Haemonchus contortus* (gi|10818965|gb|BF060055.1|BF060055).

PANZP ESTs identified as similar to *C. elegans* F52B11.3 (*C. elegans* PANZP2) include but are not limited to *Strongyloides ratti* (gi|14288440|gb|BG893830.1|BG893830); *Strongyloides stercoralis* (gi|9831122|gb|BE580180.1|BE-580180); *Meloidogyne hapla* (gi|19435833|gb|BM952243.-1|BM952243); *Brugia malayi* (gi|2605443|gb|AA661399.-1|AA661399); and *Onchocerca volvulus* (gi|14624150|gb|-BI142440.1|BI142440).

Full-Length PAN and ZP Containing Receptor-Like cDNA Sequences

Plasmid clone, Div3206, corresponding to the *S. stercoralis* EST sequence (GENBANK® Identification No: 9831352) was obtained from the Genome Sequencing Center (St. Louis, Mo.). The cDNA insert in the plasmid was sequenced in its entirety. Unless otherwise indicated, all nucleotide sequences determined herein were sequenced with an automated DNA sequencer (such as model 373 from Applied Biosystems, Inc.) using processes well-known to those skilled in the art. Primers used for sequencing are listed in Table 2 (see below). Partial sequence data for the *S. stercoralis* PANZP1 was obtained from Div3206, including nucleotide sequence for codons 141-1122 and additional 3' untranslated sequence. To obtain the missing 5'-sequence of the *S. stercoralis* PANZP1 gene, the 5'-oligo-capped RACE method (GENERACER™ kit from Invitrogen Life Technologies) was applied. This technique results in the selective ligation of an RNA oligonucleotide (SEQ ID NO: 22) to the 5'-ends of decapped mRNA using T4 RNA ligase. First strand cDNA synthesis from total *S. stercoralis* oligo-capped RNA was performed using an internal gene specific primer (PN1ss-5; SEQ ID NO: 23), designed from the known sequence, that anneals within the cDNA molecule of interest. The first strand cDNA was then directly PCR amplified using a nested gene specific primer (PN1ss-2; SEQ ID NO: 24) designed from known sequence that anneals within the cDNA molecule of interest, and the GENERACER™ 5' nested oligo (SEQ ID NO: 26), which is homologous to the 5'-end of all cDNAs amplified with the GENERACER™ oligo-capped RNA method. This procedure was performed to generate clone Div3577, which contains codons 1-184 in addition to 5'-untranslated sequences. Taken together, clones Div3206 and Div3577 contain sequences comprising the complete open reading frame of the PANZP1 gene of *S. stercoralis*.

Plasmid clone, Div3172, corresponding to the *S. stercoralis* EST sequence (GENBANK® Identification No: 9830179) was obtained from the Genome Sequencing Center (St. Louis, Mo.). The cDNA insert in the plasmid was sequenced in its entirety. Primers used for sequencing are listed in Table 2. Full sequence data for the *S. stercoralis* PANZP2 was obtained from Div3172, including nucleotide sequence for codons 1-557 and additional 5'- and 3'-untranslated sequences. Div3172 contains the complete open reading frame of the PANZP2 gene of *S. stercoralis*.

Plasmid clone, Div2577, corresponding to the *M. javanica* EST sequence (GENBANK® Identification No: 15766417) was obtained from the Genome Sequencing Center (St. Louis, Mo.). The cDNA insert in the plasmid was sequenced in its entirety. Partial sequence data for the *M. javanica* PANZP1 was obtained from Div2577, including nucleotide sequence for codons 100-233. The available sequence lacked the first 99 codons and the last 977 codons of the *M. javanica* PANZP1, as well as 5' and 3' untranslated regions. To obtain the middle region of the *M. javanica* PANZP1 gene, the 3' RACE technique was applied. First strand cDNA synthesis from total *M. javanica* RNA was performed using an oligo dT primer (SEQ ID NO: 21). The cDNA was then directly PCR amplified using a gene specific primer (PAN18; SEQ ID NO: 37) designed from the known sequence that anneals within the cDNA molecule of interest, and a degenerate primer (PAN25; SEQ ID NO: 38) designed to anneal to region of the gene predicted to exhibit strong homology shared across many nematode PANZP1 genes. This procedure was performed to generate clone Div3651, which contains codons 164-913.

To obtain the missing 5' end of the *M. javanica* PANZP1 gene, the 5' RACE technique was applied. First strand cDNA synthesis from total *M. javanica* RNA was performed using a gene specific primer (Mj-P1-R2; SEQ ID NO: 40). Single stranded cDNA was then dC-tailed and PCR amplified using a gene specific primer (Mj-P1-R3; SEQ ID NO: 41) and the AAP (abridged anchor primer) (SEQ ID NO: 50) A final nested PCR was performed using gene specific primer Mj-P1-R4 SEQ ID NO: 42) and AUAP (abridged universal primer) (SEQ ID NO: 19). This procedure was performed to generate clone Div4453, which contains codons 1-118.

To obtain the 3' end of the *M. javanica* PANZP1 gene, the 3' RACE technique was applied. First strand cDNA synthesis from *M. javanica* RNA was performed as described previously. The first strand cDNA was directly PCR amplified using a gene specific primer (P1-Mj-F2; SEQ ID NO: 39) designed from the known sequence that anneals within the first strand cDNA molecule of interest, and the AUAP primer (SEQ ID NO: 19), which is homologous to the 3' end of the cDNA of interest. This procedure was performed to generate clone Div4470, which contains codons 846-1210 in addition to 3' untranslated sequences. Taken together, clones Div2577, Div3651, Div4453, and Div4470 contain sequences comprising the complete open reading frame of the PANZP1 gene of *M. javanica*.

Partial-Length PAN and ZP Containing Receptor-Like cDNA Sequences

In an attempt to obtain the *H. glycines* PANZP1 gene, first strand cDNA derived from total *H. glycines* RNA by reverse transcription with the Oligo dT primer, was directly PCR amplified, using a degenerate primer (P1-10FA; SEQ ID NO: 43) designed to anneal to a region of strong homology shared across many nematode PANZP1 genes, and another degenerate primer (P1-02R; SEQ ID NO: 44). This procedure was performed to obtain clone Div4504, which contains codons 1-252. The *H. glycines* PANZP1 gene fragment within plasmid Div4504 is missing the 5' and 3' coding sequences. The encoded codons are arbitrarily numbered starting with number 1 for convenience. The codons contained in the *H. glycines* PANZP1 gene fragment correspond to codons 112-364 of the *C. elegans* PANZP1 gene.

Partial sequence data for the *B. malayi* PANZP1 was obtained from a *B. malayi* EST (GENBANK® Identification No: 2199168), including nucleotide sequence for codons 207-363. The available sequence lacked the first 206 codons and, approximately, the last 700 codons of the *B. malayi* PANZP1, as well as the 5' and 3' untranslated regions. Partial sequence data for the *B. malayi* PANZP1 was also obtained from the *B. malayi* EST (GENBANK® Identification No: 5342885), including nucleotide sequence for codons 256-386. The available sequence lacked the first 255 codons and, approximately, the last 680 codons of the *B. malayi* PANZP1, as well as the 5' and 3' untranslated regions.

To obtain the middle region of the *B. malayi* PANZP1 gene, the 3' RACE technique was applied. First strand cDNA synthesis from total *B. malayi* RNA was performed using an oligo dT primer (SEQ ID NO: 21). The cDNA was then directly PCR amplified using a gene specific primer (PNbm-3; SEQ ID NO: 36) designed from the known sequence that anneals within the cDNA molecule of interest, and a degenerate primer (PAN20; SEQ ID NO: 35) designed to anneal to region of strong homology shared across many nematode PANZP1 genes. This procedure was performed to generate clone Div3410, which contains codons 162-340. To obtain the 5' sequence of the B. malayi PANZP1 gene, the 5'-oligo-capped RACE method (GENERACER™ kit from Invitrogen Life Technologies) was applied. This technique results in the selective ligation of an RNA oligonucleotide (SEQ ID NO: 22) to the 5'-ends of decapped mRNA using T4 RNA ligase. First strand cDNA synthesis from total B. malayi oligo-capped RNA was performed using an internal gene specific primer (PNbm-GR; SEQ ID NO: 31), designed from the known sequence, that anneals within the cDNA molecule of interest. The first strand cDNA was then directly PCR amplified using a nested gene specific primer (PN1bm-GR-nest; SEQ ID NO: 32) designed from known sequence that anneals within the cDNA molecule of interest, and the GENERACER™ 5' nested oligo (SEQ ID NO: 26), which is homologous to the 5'-end of all cDNAs amplified with the GENERACER™ oligo-capped RNA method. This procedure was performed to generate clone Div3663, which contains codons 1-232, in addition to 5'-untranslated sequences. To obtain more of the 3' sequence of the B. malayi PANZP1 gene, the 3' RACE technique was applied. First strand cDNA synthesis from total B. malayi RNA was performed using an oligo dT primer (SEQ ID NO: 21). The cDNA was then directly PCR amplified using a gene specific primer (PNbm-5; SEQ ID NO: 33) designed from the known sequence that anneals within the cDNA molecule of interest, and a degenerate primer (PAN23; SEQ ID NO: 34) designed to anneal to region of strong homology shared across many nematode PANZP1 genes. This procedure was performed to generate clone Div3643, which contains codons 305-881. Taken together, clones Div3410, Div3663, and Div3643 contain sequences comprising approximately 75% of the complete B. malayi PANZP1 open reading frame. The 3' end sequence has yet to be completed.

TABLE 2

| Name | Sequence | SEQ ID NO | Homology to |
|---|---|---|---|
| AUAP | ggccacgcgtcgactagtac | 19 | abridged universal primer (homolgous to the 5' ends of primers Oligo dT and AAP) |
| SL1 | gggtttaattacccaagtttga | 20 | nematode transpliced leader |
| Oligo dT | ggccacgcgtcgactagtactttttttttttttttt | 21 | universal primer to poly A tail |
| RNA oligo | cgacuggagcacgaggacacugacauggacugaaggaguagaaa | 22 | GENERACER™ RNA oligo |
| PN1ss-5 | ccgtccaagaggctttgaac | 23 | Ss PANZP1 (codons 274–279) |
| PN1ss-2 | gatctggtcgatcaagtc | 24 | Ss PANZP1 (codons 180–184) |
| GR5 | cgactggagcacgaggacactga | 25 | GENERACER™ 5' primer |
| GR5n | ggacactgacatggactgaaggagta | 26 | GENERACER™ 5' nested primer |
| AN07.C09 | tcagtgacgttatgtcctcc | 27 | Ce PANZP1 genomic |
| AN07.D09 | tgacagatggaacattctcc | 28 | Ce PANZP1 genomic |
| AN08.A10 | acttcaggacacgacttgac | 29 | Ce PANZP2 genomic |
| AN08.B10 | caatcagagatggtaactcc | 30 | Ce PANZP2 genomic |
| PNbm-GR | cgttgtagacagtcgctgagtacata | 31 | Bm PANZP1 (codons 247–254) |
| PN1bm-GR-n | ccaactcgttagctagctgacg | 32 | Bm PANZP1 (codons 226–232) |
| PNbm-5 | cgaacatgtcgcaatgtac | 33 | Bm PANZP1 (codons 305–310) |
| PAN23 | catngccatdatytccca | 34 | PANZP1 degenerate (codons 876–881) |
| PAN20 | ttyggnttygartgygar | 35 | PANZP1 degenerate (codons 162–167) |
| PNbm-3 | gatcgaggcacatcgttac | 36 | Bm PANZP1 (codons 335–340) |
| PAN18 | gtttagatgctgttgatac | 37 | Mj PANZP1 (codons 164–168) |
| PAN25 | tcdatyttnccyctnggytg | 38 | Mj PANZP1 degenerate (codons 908–913) |
| P1-Mj-F2 | caagatatggacaatggaac | 39 | Mj PANZP1 (codons 846–851) |
| Mj-P1-R2 | atacattcggcatccaatgg | 40 | Mj PANZP1 (codons 181–186) |
| Mj-P1-R3 | actgactcgcattcaaagcc | 41 | Mj PANZP1 (codons 171–176) |
| Mj-P1-R4 | tagctaatctagctagtgtc | 42 | Mj PANZP1 (codons 113–118) |
| P1-10FA | garcaraaratgctngt | 43 | Hg PANZP1 (codons 1–6) |
| P1-02R | tgytcrttrtartartacat | 44 | Hg PANZP1 (codons 247–252) |
| T7 | gtaatacgactcactatagggc | 47 | vector polylinker primer |
| T3 | aattaaccctcactaaaggg | 48 | vector polylinker primer |
| SP6 | gatttaggtgacactatag | 49 | vector polylinker primer |
| AAP | ggccacgcgtcgactagtacggggggggg | 50 | abridged anchor primer |

Characterization of Nematode PAN and ZP Containing Receptor-Like Proteins

The sequences of the two PANZP-like nucleic acid molecules (PANZP1 and PANZP2 from S. stercoralis, respectively) are depicted in FIGS. 1A-1C and FIGS. 2A-2B as SEQ ID NO: 1 and SEQ ID NO: 2. The open reading frame of SEQ ID NO: 1 (SEQ ID NO: 5) contains an open reading frame encoding a 1122 amino acid polypeptide (SEQ ID NO:3). The open reading frame of SEQ ID NO: 2 (SEQ ID NO: 6) contains an open reading frame encoding a 557 amino acid polypeptide (SEQ ID NO: 4).

Figure 7C:
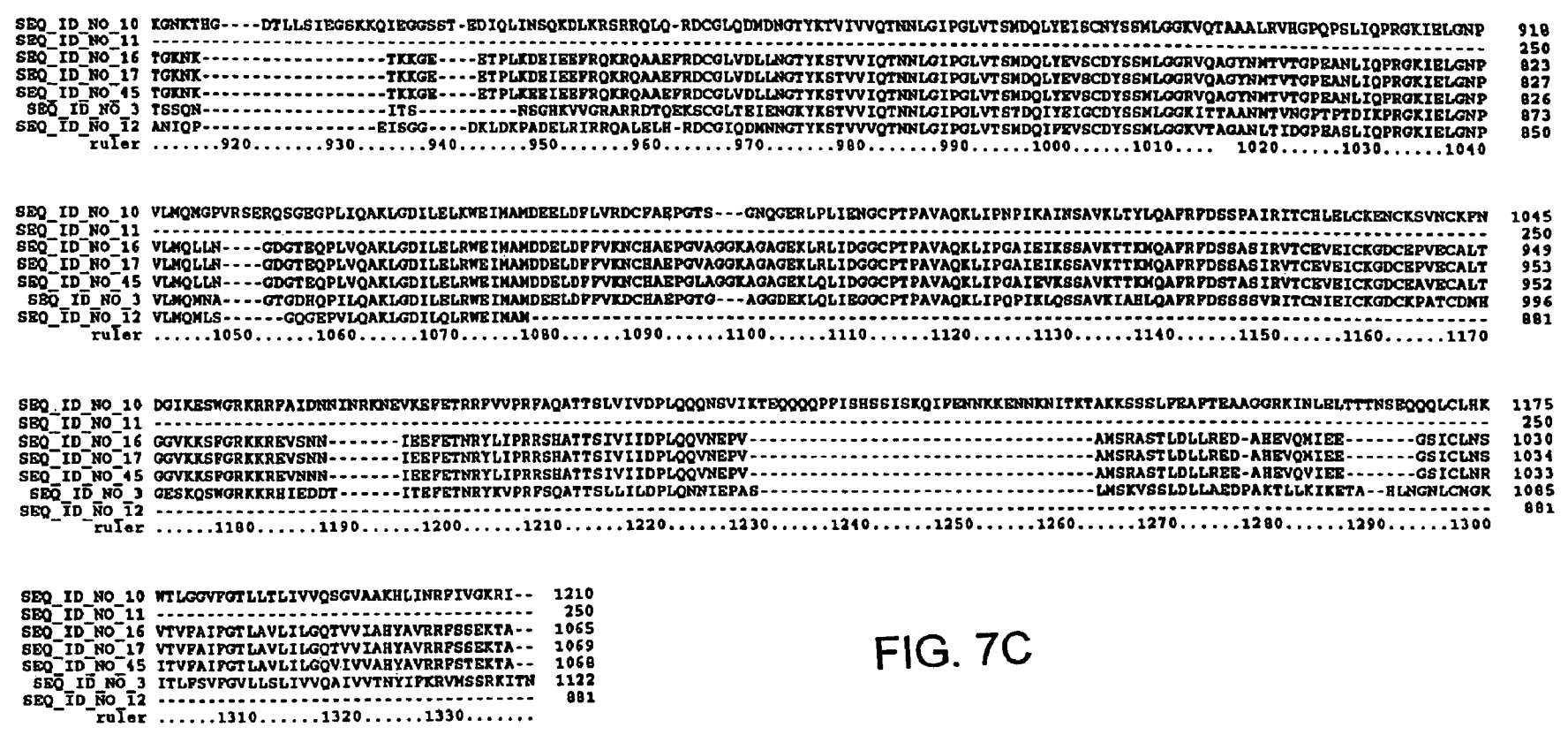

The S. stercoralis PANZP1 protein (FIGS. 1A-1C: SEQ ID NO: 3) is approximately 54% identical (in the region of shared homology) to the C. elegans PANZP1 proteins (FIG. 4; SEQ ID NOs: 7 and 8). The similarity between the PANZP1 proteins from S. stercoralis and from C. elegans is presented as a multiple alignment generated by the ClustalX multiple alignment program as described below (FIG. 7).

The S. stercoralis PANZP2 protein (FIGS. 2A-2B; SEQ ID NO: 4) is approximately 79% identical (in the region of shared homology) to the C. elegans PANZP2 protein (FIGS. 5A-5B; SEQ ID NO: 9). The similarity between the PANZP2 proteins from S. stercoralis and from C. elegans is presented as a multiple alignment generated by the ClustalX multiple alignment program as described below (FIG. 8).

The sequences of PANZP1-like nucleic acid molecules from M. javanica, H. glycines, and B. malayi are depicted in FIGS. 3A-3C, 4, and 5 as SEQ ID NO: 7, 8, and 9 respectively. The open reading frames within SEQ ID NO:

7-9 are shown as SEQ ID NO: 13-15 respectively. The *M. javanica* PANZP1-like sequence encodes a predicted polypeptide of 1210 amino acids (SEQ ID NO: 10). The partial *H. glycines* PANZP1-like sequence encodes a predicted polypeptide of 250 amino acids (SEQ ID NO: 11). The partial *B. malayi* PANZP1-like sequence encodes a predicted polypeptide of 881 amino acids (SEQ ID NO: 12).

PANZP proteins have different numbers of PAN domains (e.g., *C. elegans* PANZP2 has four PAN domains) but the overall module arrangement is the same (i.e., secretion leader, $(PAN)_X$, ZP, $T_M$). In PANZP1 the seven domains are referred to as PAN1, PAN2, PAN3, PAN4, PAN5, PAN6 and ZP. The predicted amino acid positions of these domains in the PANZP proteins are listed in the table below.

TABLE 3

Amino Acid positions of conserved PAN and ZP motifs in Nematode PANZP proteins

| Nematode | PAN1 | PAN2 | PAN3 | PAN4 | PAN5 | PAN6 | ZP |
| --- | --- | --- | --- | --- | --- | --- | --- |
| *S. stercoralis* PANZP1 (SEQ ID NO: 3) | 32–108 | 115–201 | 206–295 | 302–392 | 399–485 | 508–580 | 708–999 |
| *M. javanica* PANZP1 (SEQ ID NO: 10) | 36–122 | 129–215 | 220–309 | 316–406 | 413–499 | 520–603 | 731–1045 |
| *H. glycines* PANZP1 (SEQ ID NO: 11) |  | 1–77 | 106–196 | 198–250 |  |  |  |
| *B. malayi* PANZP1 (SEQ ID NO: 12) | 40–114 | 121–207 | 212–300 | 307–397 | 404–490 | 497–575 |  |
| *C. elegans*$_a$ PANZP1 | 25–97 | 104–190 | 212–300 | 307–397 | 404–491 | 504–576 | 652–953 |
| *C. elegans*$_b$ PANZP1 | 25–97 | 104–190 | 212–300 | 307–397 | 404–491 | 508–580 | 656–957 |
| *C. briggsae* PANZP1 | 25–97 | 104–190 | 211–299 | 306–396 | 403–490 | 507–579 | 655–956 |
| *S. stercoralis* PANZP2 (SEQ ID NO: 4) | 23–114 | 124–207 | 215–298 | 308–385 |  |  | 384–442 |
| *C. elegans* PANZP2 | 21–112 | 122–204 | 212–295 | 305–382 |  |  | 391–632 |
| *C. briggsae* PANZP2 | 22–113 | 123–205 | 213–296 | 306–383 |  |  | 392–633 |

The *M. javanica* PANZP1 protein (FIGS. 3A-3C: SEQ ID NO: 10) is approximately 46% identical (in the region of shared homology) to the *C. elegans* PANZP1 proteins (FIG. 7; SEQ ID NO: 17). The similarity between the PANZP1 proteins from *M. javanica* and from *C. elegans* is presented as a multiple alignment generated by the ClustalX multiple alignment program as described below (FIG. 7).

The *H. glycines* PANZP1 protein (FIG. 4: SEQ ID NO: 11) is approximately 65% identical (in the region of shared homology) to the *C. elegans* PANZP1 proteins (FIG. 7; SEQ ID NO: 17). The similarity between the PANZP1 proteins from *H. glycines* and from *C. elegans* is presented as a multiple alignment generated by the ClustalX multiple alignment program as described below (FIG. 7).

The *B. malayi* PANZP1 protein (FIGS. 5A-5B: SEQ ID NO: 12) is approximately 56% identical (in the region of shared homology) to the *C. elegans* PANZP1 proteins (FIG. 7; SEQ ID NO: 17). The similarity between the PANZP1 proteins from *B. malayi* and from *C. elegans* is presented as a multiple alignment generated by the ClustalX multiple alignment program as described below (FIG. 7).

Hidden Markov Model based domain analysis of the nematode PAN and ZP containing receptor-like proteins using the PFAM database (available on the internet at pfam.wustl.edu) shows that the nematode PANZP1 proteins contain six PAN domains and a single ZP domain. Different The similarity between *S. stercoralis*, *M. javanica*, *H. glycines*, and *B. malayi* PANZP sequences and other sequences was also investigated by comparison to sequence databases using BLASTP analysis against nr (a non-redundant protein sequence database available on the internet at ncbi.nlm.nih.gov) and TBLASTN analysis against dbest (an EST sequence database available on the internet at ncbi.nlm.nih.gov; top 500 hits; E=1e-4). The "Expect (E) value" is the number of sequences that are predicted to align by chance to the query sequence with a score S or greater given the size of the database queried. This analysis was used to determine the potential number of plant and vertebrate homologs for each of the nematode PANZP polypeptides described above. None of the PANZP sequences described above had high scoring vertebrate hits in nr or dbest having sufficient sequence similarity to meet the threshold E value of 1e-4 (this E value approximately corresponds to a threshold for removing sequences having a sequence identity of less than about 25% over approximately 100 amino acids). Accordingly, the PANZP enzymes of this invention do not appear to share significant sequence similarity with common vertebrate PAN containing proteins such as the *Homo sapiens* Plasminogen (gi|4505881|ref|NP_000292.1|) or ZP containing proteins such as the *Homo sapiens* Zona Pellucida 2 glycoprotein (gi|4508045|ref|NP_003451.1|).

On the basis of the lack of similarity to vertebrate PAN or ZP containing proteins and the lack of significant plant homologs, the PANZP enzymes are useful targets of inhibitory (small molecule, peptide or protein) compounds selective for nematodes over their hosts (e.g., humans, animals, and plants).

Functional predictions were made using BLAST with the default parameters on the nr database. BLAST searches and multiple alignment construction with CLUSTALX demonstrated that the C. elegans genes C34G6.6a, C34G6.6b and F52B11.3 define a family of PAN and ZP containing proteins found in nematodes and arthropods (e.g., Anopheles gambiae, C. briggsae and Drosophila melanogaster). Reciprocal blast searches and phylogenetic trees confirm that the nucleotide sequences from S. stercoralis, M. javanica, H. glycines, and B. malayi are orthologs of the C. elegans and C. briggsae genes and are therefore members of the same PANZP family of proteins. Protein localizations were predicted using the TargetP server (available on the internet at cbs.dtu.dk/services/TargetP) and transmembrane domains with the TMHMM server (available on the internet at cbs.dtu.dk/services/TMHMM). The nematode PANZP polypeptides (SEQ ID NO: 3.4, 10, 11, and 12), like the C. elegans and C. briggsae proteins (SEQ ID NO: 7, 8, 9, 45 and 46), are likely extracellular transmembrane proteins because of the presence of strong secretion leaders, C-terminal transmembrane domains and PAN and ZP domains that are likely glycosylated. Additionally, some fraction of the PANZP proteins may be cleaved from the membrane (e.g., at a polybasic site after the ZP domain) by the action of an endoproteinases (e.g., a furin-type endopeptidase).

RNA Mediated Interference (RNAi)

A double stranded RNA (dsRNA) molecule can be used to inactivate a gene encoding a PAN and ZP domain protein (PANZP) in a cell by a process known as RNA mediated-interference (Fire et al. (1998) Nature 391:806-811, and Gönczy et al. (2000) Nature 408:331-336). The dsRNA molecule can have the nucleotide sequence of a PANZP nucleic acid (preferably exonic) or a fragment thereof. For example, the molecule can comprise at least 50, at least 100, at least 200, at least 300, or at least 500 or more contiguous nucleotides of a PANZP gene. The dsRNA molecule can be delivered to nematodes via direct injection, by soaking nematodes in aqueous solution containing concentrated dsRNA, or by raising bacteriovorous nematodes on E. coli genetically engineered to produce the dsRNA molecule (Kamath et al. (2000) Genome Biol. 2; Tabara et al. (1998) Science 282:430-431).

PANZP RNAi by Feeding

C. elegans were grown on lawns of E. coli genetically engineered to produce double-stranded RNA (dsRNA) designed to inhibit PANZP1 or PANZP2 expression in order to investigate whether PANZP1 or PANZP2 expression is essential. Briefly, E. coli were transformed with genomic fragments encoding portions of the C. elegans PANZP1 or the PANZP2 gene. A 1048 nucleotide fragment was amplified from the PANZP1 gene using oligo-nucleotide primers containing the sequences 5'-TCAGTGACGTTATGTC-CTCC-3' (SEQ ID NO: 51) and 5'-TGACAGATGGAA-CATTCTCC-3' (SEQ ID NO: 52). A 926 nucleotide fragment was amplified from the PANZP2 gene using oligo-nucleotide primers containing the sequences 5'-ACTTCAGGACACGACTTGAC-3' (SEQ ID NO: 53) and 5'-CAATCAGAGATGGTAACTCC-3' (SEQ ID NO: 54) respectively. The cloned PANZP1 and PANZP2 genomic fragments were cloned separately into an E. coli expression vector between opposing T7 polymerase promoters. The expression clones were separately transformed into a strain of E. coli that carries an IPTG-inducible T7 polymerase. As a control, E. coli was transformed with a gene encoding the Green Fluorescent Protein (GFP).

Feeding RNAi was initiated from C. elegans L4 larvae at 23° C. on NGM plates containing IPTG and E. coli expressing the C. elegans PANZP1 dsRNA, PANZP2 dsRNA or GFP dsRNA. C. elegans exposed to E. coli expressing PANZP1 dsRNA or PANZP2 dsRNA exhibited severe reduction in brood size of the fed or P0 animal. In addition, of the eggs laid, only a fraction hatched, and the hatched animals died at the L1 or L2 larval stage. The sequence of the PANZP1 and PANZP2 genes is of sufficiently high complexity (i.e., unique) such that the RNAi is not likely to represent cross reactivity with other genes.

C. elegans cultures grown in the presence of E. coli expressing dsRNA from the PANZP1 or the PANZP2 gene were strongly impaired indicating that the PANZP genes provide essential functions in nematodes and that dsRNA from the PAN and ZP containing receptor-like genes is lethal when ingested by C. elegans. These results demonstrate that PANZPs are important for the viability of C. elegans and suggest that they are useful targets for the development of compounds (small molecule, peptide, protein or otherwise) that reduce the viability of nematodes.

Orthologs of PANZP1 are Present in Intestinal cDNA Libraries

An expressed sequence tag (EST) apparently encoding an orthologue of PANZP1 was identified from an Ascaris suum intestinal cDNA. The presence of a PANZP1 orthologue in an intestinal library suggests PANZP1 is expressed in the nematode intestine. In addition, the PANZP1 protein sequence contains sequences suggesting that PANZP1 is a transmembrane protein and that the PAN domains are extracellular. Together, these observations indicate that the PAN domains of PANZP1 may be accessible to drugs, peptides or proteins (e.g., antibodies) ingested by the worm.

PAN domains have been shown to be involved in protein-protein interactions in other systems (Renne et al. (2002) J. Biol. Chem. 277(7):4892-9). Therefore, one approach to inactivating the function of PANZP polypeptides is to interfere with protein-protein interactions using an antibody against a PAN domain, a peptide comprising a PAN domain or a portion of a PAN domain, or any peptide capable of strong intereaction with a native PAN domain. These entities may act as dominant negatives that will block the function of PANZP1 proteins. The intact protein fragments thereof can, for example, be over-expressed in plants where they could negatively interact with PANZP proteins of plant parasitic nematodes upon ingestion by the nematodes. Alternatively the intact proteins or fragments could be injected into or fed to a host animal and thus disrupt the function of animal parasitic nematode PANZP proteins upon ingestion by the nematodes. Since PANZP1 performs an essential function, entities that disrupt its function will have anthelmintic properties.

Identification of Additional PAN and ZP Domain Containing Receptor-Like Sequences A skilled artisan can utilize the methods provided in the example above to identify additional nematode PAN and ZP domain containing receptor-like sequences, e.g., PANZP sequences from nematodes other than S. stercoralis, M. javanica, H. glycines, B. malayi, or C. elegans. In addition, nematode PANZP sequences can be identified by a variety of methods including computer-based database searches, hybridization-based methods, and functional complementation.

Database Identification A nematode PAN and ZP containing receptor-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute (NCBI; Altschul et al. (1997) *Nucl. Acids Research* 25:3389-3402). A PAN and ZP containing receptor-like sequence of the invention can be used to query a sequence database, such as nr, dbest (expressed sequence tag (EST) sequences), and htgs (high-throughput genome sequences), using a computer-based search, e.g., FASTA, BLAST, or PSI-BLAST search. Homologous sequences in other species (e.g., plants and animals) can be detected in a PSI-BLAST search of a database such as nr (E value=10, H value=1e-2, using, for example, four iterations; available at www.ncbi.nlm.nih.gov). Sequences so obtained can be used to construct a multiple alignment, e.g., a ClustalX alignment, and/or to build a phylogenetic tree, e.g., in ClustalX using the Neighbor-Joining method (Saitou et al. (1987) *Mol. Biol. Evol.* 4:406-425) and bootstrapping (1000 replicates; Felsenstein (1985) *Evolution* 39:783-791). Distances may be corrected for the occurrence of multiple substitutions [$D_{corr}=-\ln(1-D-D^2/5)$ where D is the fraction of amino acid differences between two sequences] (Kimura (1983) *The Neutral Theory of Molecular Evolution*, Cambridge University Press).

The aforementioned search strategy can be used to identify PAN and ZP domain containing receptor-like sequences in nematodes of the following non-limiting, exemplary genera: Plant-parasitic nematode genera: *Afrina, Anguina, Aphelenchoides, Belonolaimus, Bursaphelenchus, Cacopaurus, Cactodera, Criconema, Criconemoides, Cryphodera, Ditylenchus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylenchus, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema*.

Animal- and human-parasitic nematode genera: *Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome* species (Small Strongyles), *Dictyocaulus, Dioctophyma, Dipetalonema, Dirofiliaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muellerius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanoflaria, Strongyloides, Strongylus, Spirocerca, Syngamus, Teladorsagia, Thelazia, Toxascaris, Toxocara, Trichinella, Trichostrongylus, Trichuris, Uncinaria,* and *Wuchereria*.

Particularly preferred nematode genera include: Plant: *Anguina, Aphelenchoides, Belonolaimus, Bursaphelenchus,* *Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema*.

Animal and human: *Ancylostoma, Ascaris, Brugia, Capillaria, Cooperia, Cyathostome* species, *Dictyocaulus, Dirofiliaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris,* and *Wuchereria*.

Particularly preferred nematode species include: Plant: *Anguina tritici, Aphelenchoides fragariae, Belonolaimus longicaudatus, Bursaphelenchus xylophilus, Ditylenchus destructor, Ditylenchus dipsaci Dolichodorus heterocephalous, Globodera pallida, Globodera rostochiensis, Globodera tabacum, Heterodera avenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acronea, Meloidogyne arenaria, Meloidogyne chitwoodi, Meloidogyne exigua, Meloidogyne graminicola, Meloidogyne hapla, Meloidogyne incognita, Meloidogyne javanica, Meloidogyne nassi, Nacobbus batatiformis, Pratylenchus brachyurus, Pratylenchus coffeae, Pratylenchus penetrans, Pratylenchus scribneri, Pratylenchus zeae, Radopholus similis, Rotylenchus reniformis, Tylenchulus semipenetrans, Xiphinema americanum*.

Animal and human: *Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillaria plica, Capillaria feliscati, Cooperia oncophora, Cooperia punctata, Cyathostome* species, *Dictyocaulus filaria, Dictyocaulus viviparus, Dictyocaulus arnfieldi, Dirofiliaria immitis, Dracunculus insignis, Enterobius vermicularis, Haemonchus contortus, Haemonchus placei, Necator americanus, Nematodirus helvetianus, Oesophagostomum radiatum, Onchocerca volvulus, Onchocerca cervicalis, Ostertagia ostertagi, Ostertagia circumcincta, Oxyuris equi, Parascaris equorum, Strongvloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura,* and *Wuchereria bancrofti*.

Further, a PAN and ZP domain containing receptor-like sequence can be used to identify additional PANZP sequence homologs within a genome. Multiple homologous copies of a PANZP sequence can be present. For example, a nematode PANZP sequence can be used as a seed sequence in an iterative PSI-BLAST search (default parameters, substitution matrix=Blosum62, gap open=11, gap extend=1) of a non redundant database such as wormpep (E value=1e-2, H value=1e-4, using, for example 4 iterations) to determine the number of homologs in a database, e.g., in a database containing the complete genome of an organism. A nematode PANZP sequence can be present in a genome along with 1, 2, 3, 4, 5, 6, 8, 10, or more homologs.

Hybridization Methods A nematode PAN and ZP domain containing receptor-like sequence can be identified by a hybridization-based method using a sequence provided herein as a probe. For example, a library of nematode genomic or cDNA clones can be hybridized under low stringency conditions with the probe nucleic acid. Stringency conditions can be modulated to reduce background signal and increase signal from potential positives. Clones so identified can be sequenced to verify that they encode PANZP sequences.

Another hybridization-based method utilizes an amplification reaction (e.g., the polymerase chain reaction (PCR)). Oligonucleotides, e.g., degenerate oligonucleotides, are designed to hybridize to a conserved region of a PANZP sequence (e.g., a region conserved in the nematode sequences depicted in FIGS. 7 and 8). The oligonucleotides are used as primers to amplify a PANZP sequence from template nucleic acid from a nematode, e.g., a nematode other than S. stercoralis, M. javanica, H. glycines, B. malayi, or C. elegans. The amplified fragment can be cloned and/or sequenced.

Full-length cDNA and Sequencing Methods The following methods can be used, e.g., alone or in combination with another method described herein, to obtain full-length nematode PANZP genes and determine their sequences.

Plant parasitic nematodes are maintained on greenhouse pot cultures depending on nematode preference. Root Knot Nematodes (Meloidogyne sp) are propagated on Rutgers tomato (Burpee), while Soybean Cyst Nematodes (Heterodera sp) are propagated on soybean. Total nematode RNA is isolated using the TRIZOL reagent (Gibco BRL). Briefly, 2 ml of packed worms are combined with 8 ml TRIZOL reagent and solubilized by vortexing. Following 5 minutes of incubation at room temperature, the samples are divided into smaller volumes and spun at 14,000×g for 10 minutes at 4° C. to remove insoluble material. The liquid phase is extracted with 200 μl of chloroform, and the upper aqueous phase is removed to a fresh tube. The RNA is precipitated by the addition of 500 μl of isopropanol and centrifuged to pellet. The aqueous phase is carefully removed, and the pellet is washed in 75% ethanol and spun to re-collect the RNA pellet. The supernatant is carefully removed, and the pellet is air dried for 10 minutes. The RNA pellet is resuspended in 50 μl of DEPC-$H_2O$ and analyzed by spectrophotometry at λ 260 and 280 nm to determine yield and purity. Yields can be 1-4 mg of total RNA from 2 ml of packed worms.

Full-length cDNAs can be generated using 5' and 3' RACE techniques in combination with EST sequence information. The molecular technique 5' RACE (Life Technologies, Inc., Rockville; Md.) can be employed to obtain complete or near-complete 5' ends of cDNA sequences for nematode PANZP cDNA sequences. Briefly, following the instructions provided by Life Technologies, first strand cDNA is synthesized from total nematode RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a GlassMAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequencing.

The molecular technique, 3' RACE (Life Technologies, Inc., Rockville, Md.), can be employed to obtain complete or near-complete 3' ends of cDNA sequences for nematode PANZP cDNA sequences. Briefly, following the instructions provided by Life Technologies (Rockville, Md.), first strand cDNA synthesis is performed on total nematode RNA using SuperScript™ Reverse Transcriptase and an oligo-dT primer that anneals to the polyA tail. Following degradation of the original mRNA template with RNase H, the first strand cDNA is directly PCR amplified without further purification using Taq DNA polymerase, a gene specific primer designed from available EST sequences to anneal to a site located within the first strand cDNA molecule, and a "universal" primer which contains sequence identity to 5' end of the oligo-dT primer. 3' RACE PCR amplification products are cloned into a suitable vector for further analysis and sequencing.

Nucleic Acid Variants

Isolated nucleic acid molecules of the present invention include nucleic acid molecules that have an open reading frame encoding a PANZP polypeptide. Such nucleic acid molecules include molecules having: the sequences recited in SEQ ID NO: 1, 2, 7, 8, and 9 and the sequence coding for the PANZP proteins recited in SEQ ID NO: 3, 4, 10, 11, and 12. These nucleic acid molecules can be used, for example, in a hybridization assay to detect the presence of a S. stercoralis, M. javanica, H. glycines, or B. malayi nucleic acid in a sample.

The present invention includes nucleic acid molecules such as the ones shown in SEQ ID NO: 1, 2, 7, 8, and 9 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., a PANZP activity, is not impaired. A conservative amino acid substitution results in the alteration of an amino acid for a similar acting amino acid, or amino acid of like charge, polarity, or hydrophobicity, e.g., an amino acid substitution listed in Table 4 below. At some positions, even conservative amino acid substitutions can disrupt the activity of the polypeptide.

TABLE 4

Conservative Amino Acid Replacements

| Amino acid | Code | Replace with any of |
| --- | --- | --- |
| Alanine | Ala | Gly, Cys, Ser |
| Arginine | Arg | Lys, His |
| Asparagine | Asn | Asp, Glu, Gln, |

TABLE 4-continued

Conservative Amino Acid Replacements

| Amino acid | Code | Replace with any of |
|---|---|---|
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode PANZP sequences.

Another aspect of the present invention embodies a polypeptide-encoding nucleic acid molecule that is capable of hybridizing under conditions of low stringency (or high stringency) to the nucleic acid molecule put forth in SEQ ID NO: 1, 2, 7, 8, and 9 or their complements.

The nucleic acid molecules that encode for PAN and ZP domain containing receptor-like polypeptides may correspond to the naturally occurring nucleic acid molecules or may differ by one or more nucleotide substitutions, deletions, and/or additions. Thus, the present invention extends to genes and any functional mutants, derivatives, parts, fragments, naturally occurring polymorphisms, homologs or analogs thereof or non-functional molecules. Such nucleic acid molecules can be used to detect polymorphisms of PANZP genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO: 1, 2, 7, 8, and 9, a nucleic acid molecule encoding an PANZP molecule may be obtained using standard cloning and a screening techniques, such as a method described herein.

Nucleic acid molecules of the present invention can be in the form of RNA, such as mRNA, or in the form of DNA, including, for example, cDNA and genomic DNA obtained by cloning or produced synthetically. The DNA may be double-stranded or single-stranded. The nucleic acids may be in the form of RNA/DNA hybrids. Single-stranded DNA or RNA can be the coding strand, also referred to as the sense strand, or the non-coding strand, also known as the anti-sense strand.

One embodiment of the present invention includes a recombinant nucleic acid molecule, which includes the isolated nucleic acid molecules depicted in SEQ ID NO: 1, 2, 7, 8, and 9, inserted in a vector capable of delivering and maintaining the nucleic acid molecule into a cell. The DNA molecule may be inserted into an autonomously replicating vector (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, prokaryotic, eukaryotic, or viral. Vectors can include transposons, viral vectors, episomes, (e.g., plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, E. coli. Suitable eukaryotic hosts include yeast such as S. cerevisiae, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic-acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

In an alternative embodiment, the DNA molecule is fused to a reporter gene such as β-glucuronidase gene, β-galactosidase (lacZ), chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptide affinity tag, e.g. glutathione S-transferase (GST), maltose E binding protein, protein A, FLAG tag, hexa-histidine, or the influenza HA tag. The affinity tag or reporter fusion joins the reading frames of SEQ ID NO: 1, 2, 7, 8, and/or 9 to the reading frame of the reporter gene encoding the affinity tag such that a translational fusion is generated. Expression of the fusion gene results in translation of a single polypeptide that includes both a nematode PANZP region and reporter protein or affinity tag. The fusion can also join a fragment of the reading frame of SEQ ID NO: 1, 2, 7, 8, and/or 9. The fragment can encode a functional region of the PANZP polypeptides, a structurally intact domain, or an epitope (e.g., a peptide of about 8, 10, 20, or 30 or more amino acids). A nematode PANZP nucleic acid that includes at least one of a regulatory region (e.g., a 5'-regulatory region, a promoter, an enhancer, a 5'-untranslated region, a translational start site, a 3'-untranslated region, a polyadenylation site, or a 3'-regulatory region) can also be fused to a heterologous nucleic acid. For example, the promoter of a PANZP nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant or transgenic cell. Suitable cells can either be untransformed cells or cells that have already been transformed with at least one nucleic acid molecule. Suitable cells for transformation according to the present invention can either be: (i) endogenously capable of expressing the PANZP protein or; (ii) capable of producing such protein after transformation with at least one nucleic acid molecule of the present invention.

In an exemplary embodiment, a nucleic acid of the invention is used to generate a transgenic nematode strain, e.g., a transgenic *C. elegans* strain. To generate such a strain, nucleic acid is injected into the gonad of a nematode, thus generating a heritable extrachromosomal array containing the nucleic acid (see, e.g., Mello et al. (1991) *EMBO J.* 10:3959-3970). The transgenic nematode can be propagated to generate a strain harboring the transgene. Nematodes of the strain can be used in screens to identify inhibitors specific for a *S. stercoralis, M. javanica, H. glycines*, or *B. malayi* PANZP polypeptide.

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode PANZP protein activity or production (e.g., antisense, triplex formation, ribozyme, and/or RNA drug-based reagents). The present invention includes oligonucleotides of RNA (ssRNA and dsRNA), DNA, or derivatives of either. The invention extends to the use of such oligonucleotides to protect non-nematode organisms (for example e.g., plants and animals) from disease by reading the viability of infecting nematodes, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify a PAN and ZP domain containing receptor-like nucleic acid or fragment thereof. For example, at least 10 cycles of PCR amplification can be used to obtain such an amplified nucleic acid. Primers can be at least about 8-40, 10-30 or 14-25 nucleotides in length, and can anneal to a nucleic acid "template molecule", e.g., a template molecule encoding an PANZP genetic sequence, or a functional part thereof, or its complementary sequence. The nucleic acid primer molecule can be any nucleotide sequence of at least 10 nucleotides in length derived from, or contained within sequences depicted in SEQ ID NO: 1, 2, 7, 8, and/or 9 and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any PAN and ZP domain containing receptor-like sequences that are used to identify and isolate similar genes from other organisms, including nematodes, prokaryotic organisms, and other eukaryotic organisms, such as other animals and/or plants.

In another embodiment, the invention provides oligonucleotides that are specific for a *S. stercoralis, M. javanica, H. glycines*, and *B. malayi* PANZP nucleic acid molecule. Such oligonucleotides can be used in a PCR test to determine if a *S. stercoralis, M. javanica, H. glycines*, and/or *B. malayi* derived nucleic acid is present in a sample, e.g., to monitor a disease caused *S. stercoralis, M. javanica, H. glycines*, and/or *B. malayi*.

Protein Production

Isolated PAN and ZP domain containing receptor-like proteins from nematodes can be produced in a number of ways, including production and recovery of the recombinant proteins and/or chemical synthesis of the protein. In one embodiment, an isolated nematode PANZP protein is produced by culturing a cell, e.g., a bacterial, fungal, plant, or animal cell, capable of expressing the protein, under conditions for effective production and recovery of the protein. The nucleic acid can be operably linked to a heterologous promoter, e.g., an inducible promoter or a constitutive promoter. Effective growth conditions are typically, but not necessarily, in liquid media comprising salts, water, carbon, nitrogen, phosphate sources, minerals, and other nutrients, but may be any solution in which PANZP proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The PAN and ZP domain containing receptor-like polypeptide can be fused to an affinity tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies Against PAN and ZP Domain Containing Receptor-Like Polypeptides

Recombinant PAN and ZP domain containing receptor-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO: 3, 4, 10, 11 and/or 12, or that has at least 80% similarity over 50 or more amino acids to these sequences. In a preferred embodiment, the antibody specifically binds to a polypeptide having the amino acid sequence recited in SEQ ID NO: 3, 4, 10, 11 and/or 12. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant PANZP protein.

Antibodies can be derived by immunization with a recombinant or purified PANZP gene or gene product. As used herein, the term "antibody" refers to an immunoglobulin, or fragment thereof. Examples of antibody fragments include F(ab) and F(ab')$_2$ fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length PANZP protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating PAN and ZP domain containing receptor-like antibodies can be about 8, 10, 15, 20, 30 or more amino acid residues in length, e.g., a peptide of such length obtained from SEQ ID NO: 3, 4, 10, 11 and/or 12. Useful peptides include those containing a PAN or ZP domain, e.g., a PAN or ZP domain listed in Table 3. Peptides or epitopes can also be selected from regions exposed on the surface of the protein, e.g., hydrophilic or amphipathic regions. An epitope in the vicinity of an active or binding site can be selected such that an antibody binding such an epitope would block access to the active site or prevent binding. Antibodies reactive with, or specific for, any of these regions, or other regions or domains described herein are provided. An antibody to a PANZP protein can modulate a PANZP binding activity.

Monoclonal antibodies, which can be produced by routine methods, are obtained in abundance and in homogenous form from hybridomas formed from the fusion of immortal cell lines (e.g., myelomas) with lymphocytes immunized with PANZP polypeptides such as those set forth in SEQ ID NO: 3, 4, 10, 11 and/or 12.

In addition, antibodies can be engineered, e.g., to produce a single chain antibody. (see, for example, Colcher et al. (1999) Ann N Y Acad Sci 880: 263-280; and Reiter (1996) Clin Cancer Res 2: 245-252). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of PANZP protein; (v) as PANZP inhibitors/activators that can be expressed or introduced into plants or animals for therapeutic purposes.

An antibody against a PAN and ZP domain containing receptor-like protein can be produced in a plant cell, e.g., in a transgenic plant or in culture (see, e.g., U.S. Pat. No. 6,080,560).

Antibodies that specifically recognize a S. stercoralis, M. javanica, H. glycines, and/or B. malayi PANZP proteins can be used to identify S. stercoralis, M. javanica, H. glycines, and/or B. malayi nematodes, and, thus, can be used to diagnose and/or monitor a disease caused by S. stercoralis, M. javanica, H. glycines, and/or B. malayi.

Immunization

The PANZP proteins of the invention and fragments thereof (e.g., a fragment that includes one or more PAN or ZP domains) can be used to immunize a mammal, e.g., a human, primate, or dog. The protein or peptide fragment can be introduced into a mammal as a unit dose inoculum in combination with any physiologically suitable diluent. One or more inoculums can be administered. Each inoculum can contain an amount of polypeptide effective to elicit an immune response, preferably a protective immune response that reduces the occurrence of subsequent infection by a nematode, e.g., S. steroralis or B. malayi. A unit dose can contain, e.g., at least 0.1, preferably at least 0.5 milligrams/kg of body weight of host.

The PANZP peptide immunogen can contain 10, 20, 30, 50, 100 or more amino acids and can include all or part of a PAN or ZP domain, e.g., a PAN or ZP domain listed in Table 3. The PANZP peptide immunogen can include 2, 3, 4, or more PANZP peptides that are the same or different. Moreover, the PANZP peptides can be flanked by other amino acid sequences. Thus, the immunogen can contain, e.g., two copies of a given PAN domain separated by a linker. The immunogen can include one or more portions of one, two or more PANZP proteins. Thus, the immunogen can include a portion of S. steroralis or B. malayi PANZP1 and a portion of S. steroralis PANZP2. The inoculum can include two or more non-contiguous portions of a PANZP protein, e.g., two or more portions including PAN domains.

The inoculum can include an adjuvant, e.g., complete or incomplete Freund's adjuvant. The PANZP peptide can be linked to a carrier such as tetanus toxoid, human BSA, or KLH. The inoculum can include stabilizers (e.g., sugars, preservatives, wetting agents, emulsifying agents, buffering agents, dyes, and additives) that improve viscosity of syringability. The inoculum can be administered once or multiple times (e.g., a prime and a boost).

A mammal can be inoculated by intravenous, intraperitoneal, intradermal, subcutaneous, or intramuscular method. Inoculation can be via a needle or needleless means.

Nucleic Acids Agents

Also featured are isolated nucleic acids that are antisense to nucleic acids encoding nematode PAN and ZP domain containing receptor-like proteins. An "antisense" nucleic acid includes a sequence that is complementary to the coding strand of a nucleic acid encoding a PANZP protein. The complementarity can be in a coding region of the coding strand or in a noncoding region, e.g., a 5'- or 3'-untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes The antisense nucleic acid can be a ribozyme. The ribozyme can be designed to specifically cleave RNA, e.g., a PANZP mRNA. Methods for designing such ribozymes are described in U.S. Pat. No. 5,093,246 or Haseloff and Gerlach (1988) Nature 334:585-591. For example, the ribozyme can be a derivative of Tetrahymena L-19 IVS RNA in which the nucleotide sequence of the active site is modified to be complementary to a PANZP nucleic acid (see, e.g., Cech et al. U.S. Pat. No. 4,987,071; and Cech et al. U.S. Pat. No. 5,116,742).

Peptide Nucleic acid (PNA) An antisense agent directed against an PAN and ZP domain containing receptor-like nucleic acid can be a peptide nucleic acid (PNA). See Hyrup et al. (1996) Bioorganic & Medicinal Chemistry 4: 5-23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup et al. (1996) supra and Perry-O'Keefe et al. *Proc. Natl. Acad. Sci.* 93: 14670-14675.

RNA Mediated Interference (RNAi) A double stranded RNA (dsRNA) molecule can be used to inactivate a PAN and ZP domain containing receptor-like gene in a cell by a process known as RNA mediated-interference (RNAi; e.g., Fire et al. (1998) *Nature* 391:806-811, and Gönczy et al. (2000) *Nature* 408:331-336). The dsRNA molecule can have the nucleotide sequence of a PANZP nucleic acid described herein or a fragment thereof. The molecule can be injected into a cell, or a syncytium, e.g., a nematode gonad as described in Fire et al., supra. Alternatively, the molecule can be used to eradicate a nematode infection in vertebrates or other animals by delivery to a nematode-infected animal by injection or oral dosing.

Transgenic RNAi A double stranded RNA (dsRNA) molecule can be used to inactivate a PAN and ZP domain containing receptor-like gene in a cell by a process known as RNA mediated-interference (RNAi; e.g., Fire et al. (1998) *Nature* 391:806-811, and Gönczy et al. (2000) *Nature* 408: 331-336). The dsRNA molecule can have the nucleotide sequence of all or a portion of a PANZP nucleic acid described herein or a fragment thereof. The RNAi triggering molecule can be produced by a transgenic plant engineered to produce dsRNA homologous to a PAN ZP domain-containing receptor-like gene and delivered to a plant parasitic nematode when it attacks and/or feeds on the transgenic plant. Various techniques are known in the art for expressing in plants nucleic acid molecule that inactivate a selected gene, including a nematode gene via RNAi or a related mechanism (see, e.g., Boutla et al. (2002) *Nucl. Acids Res.* 30:1688; and Wesley et al. (2001) *Plant J.* 27:581).

Screening Assays

Another embodiment of the present invention is a method of identifying a compound capable of altering (e.g., inhibiting or enhancing) the activity of PANZP molecules. This method, also referred to as a "screening assay," herein, includes, but is not limited to, the following procedure: (i) contacting an isolated PANZP protein (or a portion thereof, e.g., a PAN or ZP domain) with a test inhibitory compound under conditions in which, in the absence of the test compound, the protein has PANZP activity; and (ii) determining if the test compound alters the PANZP activity (i.e., binding of PANZP to its substrates). Suitable inhibitors or activators that alter a nematode PANZP activity include compounds that interface directly with a nematode PANZP protein substrate binding interaction. Compounds can also interact with other regions of the nematode PANZP protein outside the binding interface and enhance or interfere with PANZP-substrate interactions (e.g., allosteric effects).

Compounds A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds). Compounds and components for synthesis of compounds can be obtained from a commercial chemical supplier, e.g., Sigma-Aldrich Corp. (St. Louis, Mo.). The test compound or compounds can be naturally occurring, synthetic, or both. A test compound can be the only substance assayed by the method described herein. Alternatively, a collection of test compounds can be assayed either consecutively or concurrently by the methods described herein.

Compounds can act by allosteric inhibition or by directly by preventing the substrate PANZP interaction.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. A library can be designed and synthesized to cover such classes of chemicals, e.g., as described in DeWitt et al. (1993) *Proc. Natl. Acad. Sci. U.S.A.* 90:6909-6913; Erb et al. (1994) *Proc. Natl. Acad. Sci. USA* 91:11422-11426; Zuckermann et al. (1994) *J. Med. Chem.* 37:2678-2685; Cho et al. (1993) *Science* 261:1303-1305; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233-1251.

Organism-based Assays Organisms can be grown in microtiter plates, e.g., 6-well, 32-well, 64-well, 96-well, 384-well plates.

In one embodiment, the organism is a nematode. The nematodes can be genetically modified. Non-limiting examples of such modified nematodes include: 1) nematodes or nematode cells (*S. stercoralis, M. javanica, H. glycines, B. malayi* and/or *C. elegans*) having one or more PANZP genes inactivated (e.g., using RNA mediated interference); 2) nematodes or nematode cells expressing a heterologous PANZP gene, e.g., an PANZP gene from another species; and 3) nematodes or nematode cells having one or more endogenous PANZP genes inactivated and expressing a heterologous PANZP gene, e.g., a *S. stercoralis. M. javanica, H. glycines, B. malayi* and/or *C. elegans* PANZP gene as described herein.

A plurality of candidate compounds, e.g., a combinatorial library, can be screened. The library can be provided in a format that is amenable for robotic manipulation, e.g., in microtitre plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the compounds can be tested on a microorganism or a eukaryotic or mammalian cell line, e.g., rabbit skin cells, Chinese hamster ovary cells (CHO), and/or Hela cells. For example, CHO cells absent for PANZP genes, but expressing a nematode PANZP gene can be used. The generation of such strains is routine in the art. As described above for nematodes and nematode cells, the cell lines can be grown in microtitre plates, each well having a different candidate compound or pool of candidate compounds. Growth is monitored during or after the assay to determine if the compound or pool of compounds is a modulator of a nematode PANZP polypeptide.

In Vitro Binding Assays The screening assay can also be a cell-free binding assay, e.g., an assay to identify compounds that bind a nematode PANZP polypeptide. For example, a nematode PANZP polypeptide can be purified and labeled. The labeled polypeptide is contacted to beads; each bead has a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay to determine if the compound alters the activity of the PANZP polypeptide.

Optimization of a Compound Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above-described assays can be delineated by examination of structure-activity relationships (SAR) as is commonly practiced in the art. One can modify moieties on a lead compound and measure the effects of the modification on the efficacy of the compound to thereby produce derivatives with increased potency. For an example, see Nagarajan et al. (1988) *J. Antibiot.* 41:1430-1438. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software to do this is commercially available (e.g., Molecular Simulations, Inc.). "SAR by NMR," as described in Shuker et al. (1996) *Science* 274:1531-1534, can be used to design ligands with increased affinity, by joining lower-affinity ligands.

A preferred compound is one that interferes with the function of a nematode PAN and ZP domain containing receptor-like polypeptide and that is not substantially toxic to plants, animals, or humans. By "not substantially toxic" it is meant that the compound does not substantially affect the activity of animal, or human PAN or ZP containing proteins. Thus, particularly desirable inhibitors of *S. stercoralis, M. javanica, H. glycines, B. malayi* and/or *C. elegans* PANZP do not substantially inhibit human plasminogen, hepatycyte growth factor, Factor XI, or uromodulin activity of vertebrates, e.g., humans for example.

Standard pharmaceutical procedures can be used to assess the toxicity and therapeutic efficacy of a modulator of a PANZP activity. The LD50 (the dose lethal to 50% of the population) and the ED50 (the dose therapeutically effective in 50% of the population can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective PANZP inhibitor, while not causing undue toxicity or side effects to a subject (e.g., a host plant or host animal).

Alternatively, the ability of a candidate compound to modulate a non-nematode PAN or ZP containing polypeptide is assayed, e.g., by a method described herein. For example, the binding affinity of a candidate compound for a mammalian PAN containing polypeptide can be measured and compared to the binding affinity for a nematode PANZP polypeptide.

The aforementioned analyses can be used to identify and/or design a modulator with specificity for nematode PAN and ZP domain containing receptor-like polypeptide over vertebrate or other animal (e.g., mammalian) PAN or ZP containing polypeptides. Suitable nematodes to target are any nematodes with the PANZP proteins or proteins that can be targeted by compounds that otherwise inhibit, reduce, activate, or generally effect the activity of nematode PANZP proteins.

Inhibitors of nematode PAN and ZP domain containing receptor-like proteins can also be used to identify PAN and ZP domain containing receptor-like proteins in the nematode or other organisms using procedures known in the art, such as affinity chromatography. For example, a specific antibody may be linked to a resin and a nematode extract passed over the resin, allowing any PANZP proteins that bind the antibody to bind the resin. Subsequent biochemical techniques familiar to those skilled in the art can be performed to purify and identify bound PANZP proteins.

Agricultural Compositions

A compound that is identified as a PAN and ZP domain containing receptor-like polypeptide inhibitor can be formulated as a composition that is applied to plants, soil, or seeds in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such as another anthelmintic agent, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid molecule comprising a nucleotide sequence encoding the amino acid sequence of SEQ ID NO:11.

2. An isolated nucleic acid molecule comprising a nucleotide sequence encoding a polipeptide comprising an amino acid sequence that is at least 95% identical to the amino acid sequence of SEQ ID NO:11, wherein the polipeptide comprises three PAN domains and is a secreted membrane-bound protein.

3. The isolated nucleic acid molecule of claim 2 wherein the amino acid sequence is at least 98% identical to the amino acid sequence SEQ ID NO:11.

4. An isolated nucleic acid molecule which hybridizes to a nucleic acid molecule consisting of SEQ ID NO:14 under conditions of hybridization in 6×SSC buffer at 45° C. followed by two washes in 0.2×SSC, 0.1% SDS at 60° C., wherein the nucleic acid molecule encodes a polipeptide comprising three PAN domains and is a secreted membrane-bound protein.

5. An isolate nucleic acid molecule comprising the nucleotide sequence of SEQ ID NO:14.

6. A vector comprising the isolated nucleic acid molecule of any of claims 1, 2, 4, and 5.

7. An isolated cell comprising the vector of claim 6.

* * * * *

UNITED STATES PATENT AND TRADEMARK OFFICE
CERTIFICATE OF CORRECTION

PATENT NO. : 7,339,044 B2  Page 1 of 1
APPLICATION NO. : 11/191588
DATED : March 4, 2008
INVENTOR(S) : Michelle Coutu Hresko It is certified that error appears in the above-identified patent and that said Letters Patent is hereby corrected as shown below:

Column 135, line 7, delete "polipeptide" and replace with --polypeptide--.

Column 135, line 9, delete "polipeptide" and replace with --polypeptide--.

Column 135, line 14, between "sequence" and "SEQ" insert --of--.

Column 136, line 5, delete "polipeptide" and replace with --polypeptide--.

Column 136, line 8, delete "isolate" and replace with --isolated--.

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 54

<210> SEQ ID NO 1
<211> LENGTH: 3750
<212> TYPE: DNA
<213> ORGANISM: Strongyloides stercoralis
<220> FEATURE:
<221> NAME/KEY: CDS
<222> LOCATION: (69)...(3434)

<400> SEQUENCE: 1
cgactggagc acgaggacac tgacatggac tgaaggagta gaaaggttta aaaaacccag      60 tttgagaa atg tct aag tct ggg ctt cat ctt gta gcc tac ata tta ttg     110
         Met Ser Lys Ser Gly Leu His Leu Val Ala Tyr Ile Leu Leu
           1               5                  10 ata ttt tta att tca act aat ata gca tct aaa att tct ggt gtt cca     158
Ile Phe Leu Ile Ser Thr Asn Ile Ala Ser Lys Ile Ser Gly Val Pro
 15                  20                  25                  30 tta tgc aac aaa gat act tca cca gta ttt aca ctt caa cat aat tct     206
Leu Cys Asn Lys Asp Thr Ser Pro Val Phe Thr Leu Gln His Asn Ser
                 35                  40                  45 act aat ggt att tta gct aga tct ctt cca caa cca gga tta att gat     254
Thr Asn Gly Ile Leu Ala Arg Ser Leu Pro Gln Pro Gly Leu Ile Asp
             50                  55                  60 tgt tca gaa cat tgt tcc tct tcg tca gat tgt att ggc gtt gaa tat     302
Cys Ser Glu His Cys Ser Ser Ser Ser Asp Cys Ile Gly Val Glu Tyr
         65                  70                  75 tgg cag gga att tgt aga gtt att tct caa gat aaa act tct att tat     350
Trp Gln Gly Ile Cys Arg Val Ile Ser Gln Asp Lys Thr Ser Ile Tyr
     80                  85                  90 aca cca aca gat gaa act tca ata ctt tta aca aaa tca tgt gtt aaa     398
Thr Pro Thr Asp Glu Thr Ser Ile Leu Leu Thr Lys Ser Cys Val Lys
 95                 100                 105                 110 agt gat cgt ata tgt tca tca cca ttc cat ttt gat gtt tat gaa caa     446
Ser Asp Arg Ile Cys Ser Ser Pro Phe His Phe Asp Val Tyr Glu Gln
                115                 120                 125 aaa ata tta gtt gga ttt gct aga gaa gtt gta cca gct gag tct att     494
Lys Ile Leu Val Gly Phe Ala Arg Glu Val Val Pro Ala Glu Ser Ile
            130                 135                 140 gaa att tgt atg gct gct tgt ttg aat gct ttt gat aca tat ggt ttt     542
Glu Ile Cys Met Ala Ala Cys Leu Asn Ala Phe Asp Thr Tyr Gly Phe
        145                 150                 155 gaa tgt gaa tca gct atg tat tat cca gtt gat agt gaa tgt att ctt     590
Glu Cys Glu Ser Ala Met Tyr Tyr Pro Val Asp Ser Glu Cys Ile Leu
    160                 165                 170 aat act gaa gat aga ctt gat cga cca gat ctt ttt gtt gtt gaa aaa     638
Asn Thr Glu Asp Arg Leu Asp Arg Pro Asp Leu Phe Val Val Glu Lys
175                 180                 185                 190 gaa gat gtt gtt tat tat ctt gat tct aat tgt gct ggt tca caa tgt     686
Glu Asp Val Val Tyr Tyr Leu Asp Ser Asn Cys Ala Gly Ser Gln Cys
                195                 200                 205 tat gct cca tac att aca caa tat att gct gtt gaa aat aaa caa ata     734
Tyr Ala Pro Tyr Ile Thr Gln Tyr Ile Ala Val Glu Asn Lys Gln Ile
            210                 215                 220
```

| | | |
|---|---|---|
| gaa aat gaa tta gat aga aaa ttt gaa aat att gat ttc caa aca tgt<br>Glu Asn Glu Leu Asp Arg Lys Phe Glu Asn Ile Asp Phe Gln Thr Cys<br>225 230 235 | 782 | |
| gaa gaa tta tgt act ggt aga att act gtt aca caa aat gat ttt act<br>Glu Glu Leu Cys Thr Gly Arg Ile Thr Val Thr Gln Asn Asp Phe Thr<br>240 245 250 | 830 | |
| tgt aaa tca ttt atg tat aat cct gaa aca aaa gtt tgt tat ctt tct<br>Cys Lys Ser Phe Met Tyr Asn Pro Glu Thr Lys Val Cys Tyr Leu Ser<br>255 260 265 270 | 878 | |
| gat gaa cgt tca aag cct ctt gga cgg gct aaa tta agt gat gct aat<br>Asp Glu Arg Ser Lys Pro Leu Gly Arg Ala Lys Leu Ser Asp Ala Asn<br>275 280 285 | 926 | |
| gga ttt act tat tat gaa aaa aaa tgt ttt gca tct cca aga aca tgc<br>Gly Phe Thr Tyr Tyr Glu Lys Lys Cys Phe Ala Ser Pro Arg Thr Cys<br>290 295 300 | 974 | |
| cgt caa aca cca tca ttt aat aga gta cca caa atg att ctt gtt ggt<br>Arg Gln Thr Pro Ser Phe Asn Arg Val Pro Gln Met Ile Leu Val Gly<br>305 310 315 | 1022 | |
| ttt gct gca ttt gtt atg gaa aat gta cca tct gtt act atg tgc ctt<br>Phe Ala Ala Phe Val Met Glu Asn Val Pro Ser Val Thr Met Cys Leu<br>320 325 330 | 1070 | |
| gat caa tgt aca aat cca cca cca gag aca ggt gaa aaa ttt gtc tgt<br>Asp Gln Cys Thr Asn Pro Pro Pro Glu Thr Gly Glu Lys Phe Val Cys<br>335 340 345 350 | 1118 | |
| aaa tct gtt atg tac tat tat aat gaa caa gaa tgt att ctt aat gct<br>Lys Ser Val Met Tyr Tyr Tyr Asn Glu Gln Glu Cys Ile Leu Asn Ala<br>355 360 365 | 1166 | |
| gaa aca aga cat aca aag cca gat ctt ttt att aca gaa gga gat gaa<br>Glu Thr Arg His Thr Lys Pro Asp Leu Phe Ile Thr Glu Gly Asp Glu<br>370 375 380 | 1214 | |
| ttt ctt gtt gat tat ttt gat att tca tgt cat ctt gaa cca gaa aca<br>Phe Leu Val Asp Tyr Phe Asp Ile Ser Cys His Leu Glu Pro Glu Thr<br>385 390 395 | 1262 | |
| tgt cct aaa gga aca tat tta aaa gga att aaa tct atc aat tct gca<br>Cys Pro Lys Gly Thr Tyr Leu Lys Gly Ile Lys Ser Ile Asn Ser Ala<br>400 405 410 | 1310 | |
| ctt cct gag ggt gaa ggc tca ctt cat gtt att gag tct gct gga aaa<br>Leu Pro Glu Gly Glu Gly Ser Leu His Val Ile Glu Ser Ala Gly Lys<br>415 420 425 430 | 1358 | |
| tca tta gaa gaa tgt atg gaa aaa tgt aac caa ctt cat cca gaa aaa<br>Ser Leu Glu Glu Cys Met Glu Lys Cys Asn Gln Leu His Pro Glu Lys<br>435 440 445 | 1406 | |
| tgt aga tca ttt aat ttt gaa aaa tca tct gga tta tgt aat ctt tta<br>Cys Arg Ser Phe Asn Phe Glu Lys Ser Ser Gly Leu Cys Asn Leu Leu<br>450 455 460 | 1454 | |
| tat ctt gat gga aaa aat act tta aaa cca ttt att aaa aat gga ttt<br>Tyr Leu Asp Gly Lys Asn Thr Leu Lys Pro Phe Ile Lys Asn Gly Phe<br>465 470 475 | 1502 | |
| gat ctt gtt gat tta caa tgt tta tca act aaa aaa gat tgc tct aca<br>Asp Leu Val Asp Leu Gln Cys Leu Ser Thr Lys Lys Asp Cys Ser Thr<br>480 485 490 | 1550 | |
| aaa aag aat gat att aat ttt gtt aaa tat ctt tac tct cat ttt gtt<br>Lys Lys Asn Asp Ile Asn Phe Val Lys Tyr Leu Tyr Ser His Phe Val<br>495 500 505 510 | 1598 | |
| aaa tat ctt tac tct caa caa cct gga att cca aca aaa aca gaa aaa<br>Lys Tyr Leu Tyr Ser Gln Gln Pro Gly Ile Pro Thr Lys Thr Glu Lys<br>515 520 525 | 1646 | |
| gtt att ggt att tct aaa tgt ctt gat tta tgt act gat agt gaa cgt<br>Val Ile Gly Ile Ser Lys Cys Leu Asp Leu Cys Thr Asp Ser Glu Arg | 1694 | |

-continued

|     |     | 530 |     |     |     | 535 |     |     |     | 540 |     |      |
|-----|-----|-----|-----|-----|-----|-----|-----|-----|-----|-----|-----|------|
| tgt | gaa | gga | ctt | aat | tat | aat | aga | aga | act | gga | gaa | tgt caa tta ttt | 1742 |
| Cys | Glu | Gly | Leu | Asn | Tyr | Asn | Arg | Arg | Thr | Gly | Glu | Cys Gln Leu Phe |
|     |     | 545 |     |     |     | 550 |     |     |     | 555 |     |      |

```
tgt gaa gga ctt aat tat aat aga aga act gga gaa tgt caa tta ttt      1742
Cys Glu Gly Leu Asn Tyr Asn Arg Arg Thr Gly Glu Cys Gln Leu Phe
        545                 550                 555 gaa att att gat gga cct tct aat ctt aaa aaa tct gag cat ata gat      1790
Glu Ile Ile Asp Gly Pro Ser Asn Leu Lys Lys Ser Glu His Ile Asp
560                 565                 570 ttt tat caa aat ctt tgt tct act aaa gaa aat gaa gct ggt gtt tca     1838
Phe Tyr Gln Asn Leu Cys Ser Thr Lys Glu Asn Glu Ala Gly Val Ser
575                 580                 585                 590 tct gca tta aat gta cca caa tca tct gtt att cct att tca tca tca     1886
Ser Ala Leu Asn Val Pro Gln Ser Ser Val Ile Pro Ile Ser Ser Ser
                595                 600                 605 caa aat att agt aaa agt gat gtt ttt gcc aaa aaa aat ctt aat aaa     1934
Gln Asn Ile Ser Lys Ser Asp Val Phe Ala Lys Lys Asn Leu Asn Lys
            610                 615                 620 gat ggt aat aat caa gta aac att tat gaa cca gaa aaa aaa tac cat     1982
Asp Gly Asn Asn Gln Val Asn Ile Tyr Glu Pro Glu Lys Lys Tyr His
        625                 630                 635 cca aaa gga tca aaa aat gaa aca tca tat gaa aca gga act gta aat     2030
Pro Lys Gly Ser Lys Asn Glu Thr Ser Tyr Glu Thr Gly Thr Val Asn
640                 645                 650 aaa tca aat gtt gaa gag gtt tct gaa act tta act aat agt gga gtt     2078
Lys Ser Asn Val Glu Glu Val Ser Glu Thr Leu Thr Asn Ser Gly Val
655                 660                 665                 670 gaa agt gga agt ctt gaa aaa aat att att aca gca cca cca tct ata     2126
Glu Ser Gly Ser Leu Glu Lys Asn Ile Ile Thr Ala Pro Pro Ser Ile
                675                 680                 685 cca aaa att cct gaa ggt cca cta cca gtg cca att tta att cca gct     2174
Pro Lys Ile Pro Glu Gly Pro Leu Pro Val Pro Ile Leu Ile Pro Ala
            690                 695                 700 gat caa gta caa act att tgt gat tat gaa ggt att aaa gta caa att     2222
Asp Gln Val Gln Thr Ile Cys Asp Tyr Glu Gly Ile Lys Val Gln Ile
        705                 710                 715 aaa tca cca caa tca ttt act ggt gtt atc ttt gtt aaa aat cac tat     2270
Lys Ser Pro Gln Ser Phe Thr Gly Val Ile Phe Val Lys Asn His Tyr
720                 725                 730 gaa aca tgt cgt gtt gaa gtt tcc aac tct gat gca gct act ctt gag     2318
Glu Thr Cys Arg Val Glu Val Ser Asn Ser Asp Ala Ala Thr Leu Glu
735                 740                 745                 750 ctt ggt ctt cca gct tca ttt gga atg aaa cca gtt aca ctg tct gct     2366
Leu Gly Leu Pro Ala Ser Phe Gly Met Lys Pro Val Thr Leu Ser Ala
                755                 760                 765 aca tct tca gat tct acc tct tca cag aat att act tct aat agt gga     2414
Thr Ser Ser Asp Ser Thr Ser Ser Gln Asn Ile Thr Ser Asn Ser Gly
            770                 775                 780 cat aaa gtt gtt gga aga gca cgc cgt gat aca caa gaa aaa tct tgt     2462
His Lys Val Val Gly Arg Ala Arg Arg Asp Thr Gln Glu Lys Ser Cys
        785                 790                 795 ggt ctt aca gaa att gaa aat gga aaa tat aaa agt act gtt gtt ata     2510
Gly Leu Thr Glu Ile Glu Asn Gly Lys Tyr Lys Ser Thr Val Val Ile
800                 805                 810 caa aca aat aac ctt gga att cct gga ctt gta aca tca aca gat caa     2558
Gln Thr Asn Asn Leu Gly Ile Pro Gly Leu Val Thr Ser Thr Asp Gln
815                 820                 825                 830 att tat gaa att ggt tgt gat tat agt agt atg tta gga gga aaa att     2606
Ile Tyr Glu Ile Gly Cys Asp Tyr Ser Ser Met Leu Gly Gly Lys Ile
                835                 840                 845 act aca gca gct aat atg act gta aat gga cca aca cca act gat att     2654
```

```
                Thr Thr Ala Ala Asn Met Thr Val Asn Gly Pro Thr Pro Thr Asp Ile
                            850                 855                 860 aaa cct aga ggt aaa att gaa ctt gga aat cct gtt ctt atg caa atg    2702
Lys Pro Arg Gly Lys Ile Glu Leu Gly Asn Pro Val Leu Met Gln Met
        865                 870                 875 aat gct ggt aca ggt gat cat cag cca att tta caa gct aaa ctt gga    2750
Asn Ala Gly Thr Gly Asp His Gln Pro Ile Leu Gln Ala Lys Leu Gly
            880                 885                 890 gat att ctt gaa tta aga tgg gaa att atg gct atg gat gaa gaa ctt    2798
Asp Ile Leu Glu Leu Arg Trp Glu Ile Met Ala Met Asp Glu Glu Leu
895                 900                 905                 910 gat ttc ttt gtt aaa gat tgt cat gca gaa cct ggt act ggt gct gga    2846
Asp Phe Phe Val Lys Asp Cys His Ala Glu Pro Gly Thr Gly Ala Gly
                915                 920                 925 gga gat gaa aaa ctt cag ctt att gaa ggt gga tgc cca aca cca gct    2894
Gly Asp Glu Lys Leu Gln Leu Ile Glu Gly Gly Cys Pro Thr Pro Ala
            930                 935                 940 gtt gct caa aaa ctt att cca caa cca ata aaa tta caa tca tca gct    2942
Val Ala Gln Lys Leu Ile Pro Gln Pro Ile Lys Leu Gln Ser Ser Ala
        945                 950                 955 gtc aaa att gcc cat ctt caa gct ttc cgt ttt gat tca tcc tct tca    2990
Val Lys Ile Ala His Leu Gln Ala Phe Arg Phe Asp Ser Ser Ser Ser
    960                 965                 970 gtt aga ata aca tgt aat att gaa att tgt aag gga gat tgt aaa cca    3038
Val Arg Ile Thr Cys Asn Ile Glu Ile Cys Lys Gly Asp Cys Lys Pro
975                 980                 985                 990 gca aca tgt gat atg cac gga gaa tca aaa caa tca tgg gga aga aaa    3086
Ala Thr Cys Asp Met His Gly Glu Ser Lys Gln Ser Trp Gly Arg Lys
                995                 1000                1005 aag aga cat att gaa gat gat aca att aca gaa ttt gag aca aat cgt    3134
Lys Arg His Ile Glu Asp Asp Thr Ile Thr Glu Phe Glu Thr Asn Arg
            1010                1015                1020 tat aaa gtt cca aga ttt tca caa gca aca aca tct ctt tta att ctt    3182
Tyr Lys Val Pro Arg Phe Ser Gln Ala Thr Thr Ser Leu Leu Ile Leu
        1025                1030                1035 gat cca ctt caa aat aac att gaa cca gca tca tta atg tca aaa gta    3230
Asp Pro Leu Gln Asn Asn Ile Glu Pro Ala Ser Leu Met Ser Lys Val
    1040                1045                1050 tca tct ctt gat ttg tta gct gaa gat cct gca aaa aca tta ctt aag    3278
Ser Ser Leu Asp Leu Leu Ala Glu Asp Pro Ala Lys Thr Leu Leu Lys
1055                1060                1065                1070 att aaa gag act gca cat ttg aat gga aat ctt tgt atg gga aaa att    3326
Ile Lys Glu Thr Ala His Leu Asn Gly Asn Leu Cys Met Gly Lys Ile
                1075                1080                1085 aca ctt ttc tca gta ttt ggt gtt ctt ctt tca tta att gtt gtt caa    3374
Thr Leu Phe Ser Val Phe Gly Val Leu Leu Ser Leu Ile Val Val Gln
            1090                1095                1100 gca att gtc gta aca aat tat att ttt aaa aga gtt atg tca agc aga    3422
Ala Ile Val Val Thr Asn Tyr Ile Phe Lys Arg Val Met Ser Ser Arg
        1105                1110                1115 aag att acc aat taaactttaa taattaaaca ataattataa atatgccttt        3474
Lys Ile Thr Asn
    1120 atgttctcaa aacgagtata atcctttttt ttgttattaa ttttagtatc aaaatatata    3534 tacccgatgg catttacaat aataataaat acaactgaag aaagctataa tatgaaaccg    3594 tgccagaaac ttattcaaag ttttaatcct ctctctctct ctttctaatt tcctttcaaa    3654 acattccatt ttttttttt gttttatttt aatcaaaaaa taataattaa atagtaattt    3714
```

-continued

```
atgatatatc attaatattt ttataatatt tttttg                                    3750
```

<210> SEQ ID NO 2
<211> LENGTH: 1951
<212> TYPE: DNA
<213> ORGANISM: Strongyloides stercoralis
<220> FEATURE:
<221> NAME/KEY: CDS
<222> LOCATION: (11)...(1681)

<400> SEQUENCE: 2

```
ggcacgagaa atg aac tgg cta tct ata gct tca att tgt aca ttc tta         49
            Met Asn Trp Leu Ser Ile Ala Ser Ile Cys Thr Phe Leu
              1               5                  10 att ata cca ata tct gct gtc ttt gaa tgt tca gga tca gaa act aca        97
Ile Ile Pro Ile Ser Ala Val Phe Glu Cys Ser Gly Ser Glu Thr Thr
 15                  20                  25 gca ttt att aga ata tcc aga gca cgc ctt gat ggg aca cca gta gtt       145
Ala Phe Ile Arg Ile Ser Arg Ala Arg Leu Asp Gly Thr Pro Val Val
 30                  35                  40                  45 att tct aca gca gga cat gac ttg act tgt gca caa tat tgt aga aat       193
Ile Ser Thr Ala Gly His Asp Leu Thr Cys Ala Gln Tyr Cys Arg Asn
             50                  55                  60 aat att gaa cca aca act ggt gct caa cgt gtc tgt gca tca ttt aat       241
Asn Ile Glu Pro Thr Thr Gly Ala Gln Arg Val Cys Ala Ser Phe Asn
         65                  70                  75 ttt gat ggt cgt gaa aca tgc tac ttt ttt gat gat gct gcc tca cct       289
Phe Asp Gly Arg Glu Thr Cys Tyr Phe Phe Asp Asp Ala Ala Ser Pro
     80                  85                  90 gct ggg act ggg gag ttg aat gaa gca cca tca gct aat aat ttt tat       337
Ala Gly Thr Gly Glu Leu Asn Glu Ala Pro Ser Ala Asn Asn Phe Tyr
 95                 100                 105 tat gaa aaa gtt tgc ctt cca gct atc tct gct cat gaa gca tgt act       385
Tyr Glu Lys Val Cys Leu Pro Ala Ile Ser Ala His Glu Ala Cys Thr
110                 115                 120                 125 tat aga tca ttt tca ttt gaa aga act aga aat act caa tta gaa ggt       433
Tyr Arg Ser Phe Ser Phe Glu Arg Thr Arg Asn Thr Gln Leu Glu Gly
            130                 135                 140 ttt gtt aaa aaa tca cta caa gtt aca tca cgt gaa gaa tgc ctt tct       481
Phe Val Lys Lys Ser Leu Gln Val Thr Ser Arg Glu Glu Cys Leu Ser
        145                 150                 155 aca tgt tta aaa gaa agt gaa ttt gta tgt aga tca gtt aac tat aat       529
Thr Cys Leu Lys Glu Ser Glu Phe Val Cys Arg Ser Val Asn Tyr Asn
    160                 165                 170 tat gaa aac ttt atg tgt gaa ctt tca aca gaa aga tcg cgt tct aaa       577
Tyr Glu Asn Phe Met Cys Glu Leu Ser Thr Glu Arg Ser Arg Ser Lys
175                 180                 185 cca caa aat atg aga atg tca gca gct cca gtt gat tat tat gat aat       625
Pro Gln Asn Met Arg Met Ser Ala Ala Pro Val Asp Tyr Tyr Asp Asn
190                 195                 200                 205 aat tgt tta aat aga caa aat aga tgt ggt gaa tct ggt gga aat ttg       673
Asn Cys Leu Asn Arg Gln Asn Arg Cys Gly Glu Ser Gly Gly Asn Leu
            210                 215                 220 att ttt att aaa aca aca caa ttt gaa att cat tat tat gat cat act       721
Ile Phe Ile Lys Thr Thr Gln Phe Glu Ile His Tyr Tyr Asp His Thr
        225                 230                 235 caa tca atg gaa gca caa gaa tca ttc tgt tta caa aaa tgt tta gat       769
Gln Ser Met Glu Ala Gln Glu Ser Phe Cys Leu Gln Lys Cys Leu Asp
    240                 245                 250 tca tta aac acc ttc tgt aga tct gtt gaa tat tct cca tct gaa aaa       817
Ser Leu Asn Thr Phe Cys Arg Ser Val Glu Tyr Ser Pro Ser Glu Lys
```

-continued

```
                255                 260                 265
aat tgt att gtt tct gat gaa gat aca tat tca aga gct gat caa caa      865
Asn Cys Ile Val Ser Asp Glu Asp Thr Tyr Ser Arg Ala Asp Gln Gln
270                 275                 280                 285 ggt gaa gtt aat aat aaa gat tat tat gaa cct gtt tgt gtt gct gct      913
Gly Glu Val Asn Asn Lys Asp Tyr Tyr Glu Pro Val Cys Val Ala Ala
                290                 295                 300 gat ctt agt tca tct aca tgt cgt caa caa gct gct ttt gaa aga ttt      961
Asp Leu Ser Ser Ser Thr Cys Arg Gln Gln Ala Ala Phe Glu Arg Phe
            305                 310                 315 att ggt tct gct att gaa ggt acc cca gtt gct aca gca caa caa gta     1009
Ile Gly Ser Ala Ile Glu Gly Thr Pro Val Ala Thr Ala Gln Gln Val
        320                 325                 330 acc att tct gat tgt att tca ctt tgt ttc caa aat ttg aat tgt aaa     1057
Thr Ile Ser Asp Cys Ile Ser Leu Cys Phe Gln Asn Leu Asn Cys Lys
    335                 340                 345 tca att aat tat gat cgt aca caa tct aca tgt tat att tat gct gtt     1105
Ser Ile Asn Tyr Asp Arg Thr Gln Ser Thr Cys Tyr Ile Tyr Ala Val
350                 355                 360                 365 gga aga caa gaa tct aat gtt aaa aat gat gca agt ttc gat tat tat     1153
Gly Arg Gln Glu Ser Asn Val Lys Asn Asp Ala Ser Phe Asp Tyr Tyr
                370                 375                 380 gaa ttt aca att att gat aat gga tgc cca aga tat cct gct ctt gta     1201
Glu Phe Thr Ile Ile Asp Asn Gly Cys Pro Arg Tyr Pro Ala Leu Val
            385                 390                 395 ggg cca gtt tta caa gat ttc gac aaa aat cgt ctt aaa tct gaa atg     1249
Gly Pro Val Leu Gln Asp Phe Asp Lys Asn Arg Leu Lys Ser Glu Met
        400                 405                 410 aaa gca ttc cgt tta gat gga tca tat gat att caa att gaa tgt tct     1297
Lys Ala Phe Arg Leu Asp Gly Ser Tyr Asp Ile Gln Ile Glu Cys Ser
    415                 420                 425 gtt atg ttt tgt gct ggt cca atg ggt tgt cca cca tct aat tgc ctt     1345
Val Met Phe Cys Ala Gly Pro Met Gly Cys Pro Pro Ser Asn Cys Leu
430                 435                 440                 445 gat tca gga aca aat gaa tta ttt gct tca cat gga aga aag aaa aga     1393
Asp Ser Gly Thr Asn Glu Leu Phe Ala Ser His Gly Arg Lys Lys Arg
                450                 455                 460 agt att gtt gat ttc aaa aat aca aca aca tct gca gaa aca tta tct     1441
Ser Ile Val Asp Phe Lys Asn Thr Thr Thr Ser Ala Glu Thr Leu Ser
            465                 470                 475 gct ata att aga gta ctt gct gct gga gaa gaa gaa tta gaa gtt gaa     1489
Ala Ile Ile Arg Val Leu Ala Ala Gly Glu Glu Glu Leu Glu Val Glu
        480                 485                 490 gaa ttt tat aga aat gat act aat ttt aaa tat gat tct gaa gaa aat     1537
Glu Phe Tyr Arg Asn Asp Thr Asn Phe Lys Tyr Asp Ser Glu Glu Asn
    495                 500                 505 atc tca gct cat aac tta tac tgt atg tct gaa atg tgg ttt gta tca     1585
Ile Ser Ala His Asn Leu Tyr Cys Met Ser Glu Met Trp Phe Val Ser
510                 515                 520                 525 gga att gtt tca atg gct atg atc tgt ctt ctt ctt tct gtt ctt ata     1633
Gly Ile Val Ser Met Ala Met Ile Cys Leu Leu Leu Ser Val Leu Ile
                530                 535                 540 gtt atg tgg ggc tgt cat tca tta aat caa tct tca aaa tta cca atg     1681
Val Met Trp Gly Cys His Ser Leu Asn Gln Ser Ser Lys Leu Pro Met
            545                 550                 555 tgaaggaaga tctttcaaca aaaaaaaacg attaatttt aatatttctt taatatatac    1741
attccataat cagtatatac tataataatt gcaacataat aatttattgt agaagtctgt   1801
ttataaaatc aaatcacaaa ttttctcttt acagtactgt gcacaacaac aagaaattcc   1861
```

-continued

```
aatctcttcc tatattttga tgtcgtacac acgtttataa aaacaaattc ttttggtttt      1921
taatcagttt tcagtttaca tttatataat                                       1951
```

<210> SEQ ID NO 3
<211> LENGTH: 1122
<212> TYPE: PRT
<213> ORGANISM: Strongyloides stercoralis

<400> SEQUENCE: 3

| Met | Ser | Lys | Ser | Gly | Leu | His | Leu | Val | Ala | Tyr | Ile | Leu | Leu | Ile | Phe |
|---|---|---|---|---|---|---|---|---|---|---|---|---|---|---|---|
| 1 | | | | 5 | | | | | 10 | | | | | 15 | |

Leu Ile Ser Thr Asn Ile Ala Ser Lys Ile Ser Gly Val Pro Leu Cys
            20                  25                  30

Asn Lys Asp Thr Ser Pro Val Phe Thr Leu Gln His Asn Ser Thr Asn
        35                  40                  45

Gly Ile Leu Ala Arg Ser Leu Pro Gln Pro Gly Leu Ile Asp Cys Ser
    50                  55                  60

Glu His Cys Ser Ser Ser Asp Cys Ile Gly Val Glu Tyr Trp Gln
65                  70                  75                  80

Gly Ile Cys Arg Val Ile Ser Gln Asp Lys Thr Ser Ile Tyr Thr Pro
                85                  90                  95

Thr Asp Glu Thr Ser Ile Leu Leu Thr Lys Ser Cys Val Lys Ser Asp
            100                 105                 110

Arg Ile Cys Ser Ser Pro Phe His Phe Asp Val Tyr Glu Gln Lys Ile
        115                 120                 125

Leu Val Gly Phe Ala Arg Glu Val Val Pro Ala Glu Ser Ile Glu Ile
    130                 135                 140

Cys Met Ala Ala Cys Leu Asn Ala Phe Asp Thr Tyr Gly Phe Glu Cys
145                 150                 155                 160

Glu Ser Ala Met Tyr Tyr Pro Val Asp Ser Glu Cys Ile Leu Asn Thr
                165                 170                 175

Glu Asp Arg Leu Asp Arg Pro Asp Leu Phe Val Val Glu Lys Glu Asp
            180                 185                 190

Val Val Tyr Tyr Leu Asp Ser Asn Cys Ala Gly Ser Gln Cys Tyr Ala
        195                 200                 205

Pro Tyr Ile Thr Gln Tyr Ile Ala Val Glu Asn Lys Gln Ile Glu Asn
    210                 215                 220

Glu Leu Asp Arg Lys Phe Glu Asn Ile Asp Phe Gln Thr Cys Glu Glu
225                 230                 235                 240

Leu Cys Thr Gly Arg Ile Thr Val Thr Gln Asn Asp Phe Thr Cys Lys
                245                 250                 255

Ser Phe Met Tyr Asn Pro Glu Thr Lys Val Cys Tyr Leu Ser Asp Glu
            260                 265                 270

Arg Ser Lys Pro Leu Gly Arg Ala Lys Leu Ser Asp Ala Asn Gly Phe
        275                 280                 285

Thr Tyr Tyr Glu Lys Lys Cys Phe Ala Ser Pro Arg Thr Cys Arg Gln
    290                 295                 300

Thr Pro Ser Phe Asn Arg Val Pro Gln Met Ile Leu Val Gly Phe Ala
305                 310                 315                 320

Ala Phe Val Met Glu Asn Val Pro Ser Val Thr Met Cys Leu Asp Gln
                325                 330                 335

Cys Thr Asn Pro Pro Glu Thr Gly Glu Lys Phe Val Cys Lys Ser
            340                 345                 350

-continued

```
Val Met Tyr Tyr Tyr Asn Glu Gln Glu Cys Ile Leu Asn Ala Glu Thr
            355                 360                 365

Arg His Thr Lys Pro Asp Leu Phe Ile Thr Glu Gly Asp Glu Phe Leu
        370                 375                 380

Val Asp Tyr Phe Asp Ile Ser Cys His Leu Glu Pro Glu Thr Cys Pro
385                 390                 395                 400

Lys Gly Thr Tyr Leu Lys Gly Ile Lys Ser Ile Asn Ser Ala Leu Pro
                405                 410                 415

Glu Gly Glu Gly Ser Leu His Val Ile Glu Ser Ala Gly Lys Ser Leu
            420                 425                 430

Glu Glu Cys Met Glu Lys Cys Asn Gln Leu His Pro Glu Lys Cys Arg
        435                 440                 445

Ser Phe Asn Phe Glu Lys Ser Ser Gly Leu Cys Asn Leu Leu Tyr Leu
        450                 455                 460

Asp Gly Lys Asn Thr Leu Lys Pro Phe Ile Lys Asn Gly Phe Asp Leu
465                 470                 475                 480

Val Asp Leu Gln Cys Leu Ser Thr Lys Lys Asp Cys Ser Thr Lys Lys
                485                 490                 495

Asn Asp Ile Asn Phe Val Lys Tyr Leu Tyr Ser His Phe Val Lys Tyr
            500                 505                 510

Leu Tyr Ser Gln Gln Pro Gly Ile Pro Thr Lys Thr Glu Lys Val Ile
        515                 520                 525

Gly Ile Ser Lys Cys Leu Asp Leu Cys Thr Asp Ser Glu Arg Cys Glu
        530                 535                 540

Gly Leu Asn Tyr Asn Arg Arg Thr Gly Glu Cys Gln Leu Phe Glu Ile
545                 550                 555                 560

Ile Asp Gly Pro Ser Asn Leu Lys Lys Ser Glu His Ile Asp Phe Tyr
                565                 570                 575

Gln Asn Leu Cys Ser Thr Lys Glu Asn Glu Ala Gly Val Ser Ser Ala
            580                 585                 590

Leu Asn Val Pro Gln Ser Ser Val Ile Pro Ile Ser Ser Gln Asn
        595                 600                 605

Ile Ser Lys Ser Asp Val Phe Ala Lys Lys Asn Leu Asn Lys Asp Gly
        610                 615                 620

Asn Asn Gln Val Asn Ile Tyr Glu Pro Glu Lys Lys Tyr His Pro Lys
625                 630                 635                 640

Gly Ser Lys Asn Glu Thr Ser Tyr Glu Thr Gly Thr Val Asn Lys Ser
                645                 650                 655

Asn Val Glu Glu Val Ser Glu Thr Leu Thr Asn Ser Gly Val Glu Ser
            660                 665                 670

Gly Ser Leu Glu Lys Asn Ile Ile Thr Ala Pro Pro Ser Ile Pro Lys
        675                 680                 685

Ile Pro Glu Gly Pro Leu Pro Val Pro Ile Leu Ile Pro Ala Asp Gln
        690                 695                 700

Val Gln Thr Ile Cys Asp Tyr Glu Gly Ile Lys Val Gln Ile Lys Ser
705                 710                 715                 720

Pro Gln Ser Phe Thr Gly Val Ile Phe Val Lys Asn His Tyr Glu Thr
                725                 730                 735

Cys Arg Val Glu Val Ser Asn Ser Asp Ala Ala Thr Leu Glu Leu Gly
            740                 745                 750

Leu Pro Ala Ser Phe Gly Met Lys Pro Val Thr Leu Ser Ala Thr Ser
        755                 760                 765

Ser Asp Ser Thr Ser Ser Gln Asn Ile Thr Ser Asn Ser Gly His Lys
```

```
                    770             775             780
Val Val Gly Arg Ala Arg Arg Asp Thr Gln Glu Lys Ser Cys Gly Leu
785             790             795             800

Thr Glu Ile Glu Asn Gly Lys Tyr Lys Ser Thr Val Val Ile Gln Thr
            805             810             815

Asn Asn Leu Gly Ile Pro Gly Leu Val Thr Ser Thr Asp Gln Ile Tyr
        820             825             830

Glu Ile Gly Cys Asp Tyr Ser Ser Met Leu Gly Gly Lys Ile Thr Thr
            835             840             845

Ala Ala Asn Met Thr Val Asn Gly Pro Thr Pro Thr Asp Ile Lys Pro
850             855             860

Arg Gly Lys Ile Glu Leu Gly Asn Pro Val Leu Met Gln Met Asn Ala
865             870             875             880

Gly Thr Gly Asp His Gln Pro Ile Leu Gln Ala Lys Leu Gly Asp Ile
            885             890             895

Leu Glu Leu Arg Trp Glu Ile Met Ala Met Asp Glu Glu Leu Asp Phe
            900             905             910

Phe Val Lys Asp Cys His Ala Glu Pro Gly Thr Gly Ala Gly Gly Asp
            915             920             925

Glu Lys Leu Gln Leu Ile Glu Gly Gly Cys Pro Thr Pro Ala Val Ala
        930             935             940

Gln Lys Leu Ile Pro Gln Pro Ile Lys Leu Gln Ser Ser Ala Val Lys
945             950             955             960

Ile Ala His Leu Gln Ala Phe Arg Phe Asp Ser Ser Ser Val Arg
            965             970             975

Ile Thr Cys Asn Ile Glu Ile Cys Lys Gly Asp Cys Lys Pro Ala Thr
            980             985             990

Cys Asp Met His Gly Glu Ser Lys Gln Ser Trp Gly Arg Lys Lys Arg
            995            1000            1005

His Ile Glu Asp Asp Thr Ile Thr Glu Phe Glu Thr Asn Arg Tyr Lys
           1010            1015            1020

Val Pro Arg Phe Ser Gln Ala Thr Thr Ser Leu Leu Ile Leu Asp Pro
1025            1030            1035            1040

Leu Gln Asn Asn Ile Glu Pro Ala Ser Leu Met Ser Lys Val Ser Ser
           1045            1050            1055

Leu Asp Leu Leu Ala Glu Asp Pro Ala Lys Thr Leu Leu Lys Ile Lys
           1060            1065            1070

Glu Thr Ala His Leu Asn Gly Asn Leu Cys Met Gly Lys Ile Thr Leu
           1075            1080            1085

Phe Ser Val Phe Gly Val Leu Leu Ser Leu Ile Val Gln Ala Ile
           1090            1095            1100

Val Val Thr Asn Tyr Ile Phe Lys Arg Val Met Ser Ser Arg Lys Ile
1105            1110            1115            1120

Thr Asn

<210> SEQ ID NO 4
<211> LENGTH: 557
<212> TYPE: PRT
<213> ORGANISM: Strongyloides stercoralis

<400> SEQUENCE: 4

Met Asn Trp Leu Ser Ile Ala Ser Ile Cys Thr Phe Leu Ile Ile Pro
1               5               10              15

Ile Ser Ala Val Phe Glu Cys Ser Gly Ser Glu Thr Thr Ala Phe Ile
```

-continued

```
                20                  25                  30
Arg Ile Ser Arg Ala Arg Leu Asp Gly Thr Pro Val Val Ile Ser Thr
            35                  40                  45
Ala Gly His Asp Leu Thr Cys Ala Gln Tyr Cys Arg Asn Asn Ile Glu
        50                  55                  60
Pro Thr Thr Gly Ala Gln Arg Val Cys Ala Ser Phe Asn Phe Asp Gly
65                  70                  75                  80
Arg Glu Thr Cys Tyr Phe Phe Asp Asp Ala Ser Pro Ala Gly Thr
                85                  90                  95
Gly Glu Leu Asn Glu Ala Pro Ser Ala Asn Asn Phe Tyr Tyr Glu Lys
            100                 105                 110
Val Cys Leu Pro Ala Ile Ser Ala His Glu Ala Cys Thr Tyr Arg Ser
            115                 120                 125
Phe Ser Phe Glu Arg Thr Arg Asn Thr Gln Leu Glu Gly Phe Val Lys
        130                 135                 140
Lys Ser Leu Gln Val Thr Ser Arg Glu Glu Cys Leu Ser Thr Cys Leu
145                 150                 155                 160
Lys Glu Ser Glu Phe Val Cys Arg Ser Val Asn Tyr Asn Tyr Glu Asn
                165                 170                 175
Phe Met Cys Glu Leu Ser Thr Glu Arg Ser Arg Ser Lys Pro Gln Asn
            180                 185                 190
Met Arg Met Ser Ala Ala Pro Val Asp Tyr Tyr Asp Asn Asn Cys Leu
        195                 200                 205
Asn Arg Gln Asn Arg Cys Gly Glu Ser Gly Asn Leu Ile Phe Ile
        210                 215                 220
Lys Thr Thr Gln Phe Glu Ile His Tyr Tyr Asp His Thr Gln Ser Met
225                 230                 235                 240
Glu Ala Gln Glu Ser Phe Cys Leu Gln Lys Cys Leu Asp Ser Leu Asn
                245                 250                 255
Thr Phe Cys Arg Ser Val Glu Tyr Ser Pro Ser Glu Lys Asn Cys Ile
            260                 265                 270
Val Ser Asp Glu Asp Thr Tyr Ser Arg Ala Asp Gln Gln Gly Glu Val
        275                 280                 285
Asn Asn Lys Asp Tyr Tyr Glu Pro Val Cys Val Ala Ala Asp Leu Ser
        290                 295                 300
Ser Ser Thr Cys Arg Gln Gln Ala Ala Phe Glu Arg Phe Ile Gly Ser
305                 310                 315                 320
Ala Ile Glu Gly Thr Pro Val Thr Ala Gln Val Thr Ile Ser
                325                 330                 335
Asp Cys Ile Ser Leu Cys Phe Gln Asn Leu Asn Cys Lys Ser Ile Asn
            340                 345                 350
Tyr Asp Arg Thr Gln Ser Thr Cys Tyr Ile Tyr Ala Val Gly Arg Gln
        355                 360                 365
Glu Ser Asn Val Lys Asn Asp Ala Ser Phe Asp Tyr Tyr Glu Phe Thr
        370                 375                 380
Ile Ile Asp Asn Gly Cys Pro Arg Tyr Pro Ala Leu Val Gly Pro Val
385                 390                 395                 400
Leu Gln Asp Phe Asp Lys Asn Arg Leu Lys Ser Glu Met Lys Ala Phe
                405                 410                 415
Arg Leu Asp Gly Ser Tyr Asp Ile Gln Ile Glu Cys Ser Val Met Phe
            420                 425                 430
Cys Ala Gly Pro Met Gly Cys Pro Pro Ser Asn Cys Leu Asp Ser Gly
        435                 440                 445
```

```
Thr Asn Glu Leu Phe Ala Ser His Gly Arg Lys Lys Arg Ser Ile Val
    450                 455                 460

Asp Phe Lys Asn Thr Thr Thr Ser Ala Glu Thr Leu Ser Ala Ile Ile
465                 470                 475                 480

Arg Val Leu Ala Ala Gly Glu Glu Leu Glu Val Glu Glu Phe Tyr
                485                 490                 495

Arg Asn Asp Thr Asn Phe Lys Tyr Asp Ser Glu Asn Ile Ser Ala
                500                 505                 510

His Asn Leu Tyr Cys Met Ser Glu Met Trp Phe Val Ser Gly Ile Val
            515                 520                 525

Ser Met Ala Met Ile Cys Leu Leu Leu Ser Val Leu Ile Val Met Trp
    530                 535                 540

Gly Cys His Ser Leu Asn Gln Ser Ser Lys Leu Pro Met
545                 550                 555

<210> SEQ ID NO 5
<211> LENGTH: 3369
<212> TYPE: DNA
<213> ORGANISM: Strongyloides stercoralis

<400> SEQUENCE: 5
atgtctaagt ctgggcttca tcttgtagcc tacatattat tgatattttt aatttcaact      60
aatatagcat ctaaaatttc tggtgttcca ttatgcaaca aagatacttc accagtattt     120
acacttcaac ataattctac taatggtatt ttagctagat ctcttccaca accaggatta     180
attgattgtt cagaacattg ttcctcttcg tcagattgta ttggcgttga atattggcag     240
ggaatttgta gagttatttc tcaagataaa acttctattt atacaccaac agatgaaact     300
tcaatacttt taacaaaatc atgtgttaaa agtgatcgta tatgttcatc accattccat     360
tttgatgttt atgaacaaaa aatattagtt ggatttgcta gagaagttgt accagctgag     420
tctattgaaa tttgtatggc tgcttgtttg aatgcttttg atacatatgg ttttgaatgt     480
gaatcagcta tgtattatcc agttgatagt gaatgtattc ttaatactga agatagactt     540
gatcgaccag atcttttttgt tgttgaaaaa gaagatgttg tttattatct tgattctaat     600
tgtgctggtt cacaatgtta tgctccatac attacacaat atattgctgt tgaaaataaa     660
caaatagaaa atgaattaga tagaaaattt gaaaatattg atttccaaac atgtgaagaa     720
ttatgtactg gtagaattac tgttacacaa aatgatttta cttgtaaatc atttatgtat     780
aatcctgaaa caaaagtttg ttatctttct gatgaacgtt caaagcctct tggacgggct     840
aaattaagtg atgctaatgg atttacttat tatgaaaaaa aatgttttgc atctccaaga     900
acatgccgtc aaacaccatc atttaataga gtaccacaaa tgattcttgt tggttttgct     960
gcatttgtta tggaaaatgt accatctgtt actatgtgcc ttgatcaatg tacaaatcca    1020
ccaccagaga caggtgaaaa atttgtctgt aaatctgtta tgtactatta taatgaacaa    1080
gaatgtattc ttaatgctga acaagacat acaaagccag atcttttttat tacagaagga    1140
gatgaatttc ttgttgatta ttttgatatt tcatgtcatc ttgaaccaga acatgtcct    1200
aaaggaacat atttaaaagg aattaaatct atcaattctg cacttcctga gggtgaaggc    1260
tcacttcatg ttattgagtc tgctggaaaa tcattagaag aatgtatgga aaaatgtaac    1320
caacttcatc cagaaaaatg tagatcattt aattttgaaa atcatctgg attatgtaat    1380
cttttatatc ttgatggaaa aaatacttta aaaccatttta ttaaaatgg atttgatctt    1440
gttgatttac aatgtttatc aactaaaaaa gattgctcta caaaaaagaa tgatattaat    1500
```

```
tttgttaaat atctttactc tcattttgtt aaatatcttt actctcaaca acctggaatt     1560
ccaacaaaaa cagaaaaagt tattggtatt tctaaatgtc ttgatttatg tactgatagt     1620
gaacgttgtg aaggacttaa ttataataga agaactggag aatgtcaatt atttgaaatt     1680
attgatggac cttctaatct taaaaaatct gagcatatag attttatca aaatctttgt      1740 tctactaaag aaaatgaagc tggtgtttca tctgcattaa atgtaccaca atcatctgtt     1800
attcctattt catcatcaca aaatattagt aaaagtgatg ttttgccaa aaaaaatctt      1860 aataaagatg gtaataatca agtaaacatt tatgaaccag aaaaaaaata ccatccaaaa     1920
ggatcaaaaa atgaaacatc atatgaaaca ggaactgtaa ataaatcaaa tgttgaagag     1980
gtttctgaaa cttttaactaa tagtggagtt gaaagtggaa gtcttgaaaa aaatattatt    2040
acagcaccac catctatacc aaaaattcct gaaggtccac taccagtgcc aattttaatt    2100
ccagctgatc aagtacaaac tatttgtgat tatgaaggta ttaaagtaca aattaaatca     2160
ccacaatcat ttactggtgt tatctttgtt aaaaatcact atgaaacatg tcgtgttgaa    2220
gtttccaact ctgatgcagc tactcttgag cttggtcttc cagcttcatt tggaatgaaa     2280
ccagttacac tgtctgctac atcttcagat tctacctctt cacagaatat tacttctaat    2340
agtggacata aagttgttgg aagagcacgc cgtgatacac aagaaaaatc ttgtggtctt    2400
acagaaattg aaaatggaaa atataaaagt actgttgtta tacaaacaaa taaccttgga    2460
attcctggac ttgtaacatc aacagatcaa atttatgaaa ttggttgtga ttatagtagt    2520
atgttaggag gaaaaattac tacagcagct aatatgactg taaatggacc aacaccaact    2580
gatattaaac ctagaggtaa aattgaactt ggaaatcctg ttcttatgca aatgaatgct    2640
ggtacaggtg atcatcagcc aattttacaa gctaaacttg gagatattct tgaattaaga    2700
tgggaaatta tggctatgga tgaagaactt gatttctttg ttaaagattg tcatgcagaa    2760
cctggtactg gtgctggagg agatgaaaaa cttcagctta ttgaaggtgg atgcccaaca    2820
ccagctgttg ctcaaaaact tattccacaa ccaataaaat tacaatcatc agctgtcaaa    2880
attgcccatc ttcaagcttt ccgttttgat tcatcctctt cagttagaat aacatgtaat    2940
attgaaattt gtaagggaga ttgtaaacca gcaacatgtg atatgcacgg agaatcaaaa    3000
caatcatggg gaagaaaaaa gagacatatt gaagatgata caattacaga atttgagaca    3060
aatcgttata agttccaag attttcacaa gcaacaacat ctctttaat tcttgatcca     3120 cttcaaaata acattgaacc agcatcatta atgtcaaaag tatcatctct tgatttgtta    3180
gctgaagatc ctgcaaaaac attacttaag attaaagaga ctgcacattt gaatggaaat     3240 cttttgtatgg gaaaaattac actttttctca gtatttggtg ttcttcttc attaattgtt    3300 gttcaagcaa ttgtcgtaac aaattatatt tttaaaagag ttatgtcaag cagaaagatt    3360
accaattaa                                                             3369
```

<210> SEQ ID NO 6
<211> LENGTH: 1674
<212> TYPE: DNA
<213> ORGANISM: Strongyloides stercoralis

<400> SEQUENCE: 6

```
atgaactggc tatctatagc ttcaatttgt acattcttaa ttataccaat atctgctgtc         60
tttgaatgtt caggatcaga aactacagca tttattagaa tatccagagc acgccttgat        120
gggacaccag tagttatttc tacagcagga catgacttga cttgtgcaca atattgtaga       180
```

```
aataatattg aaccaacaac tggtgctcaa cgtgtctgtg catcatttaa ttttgatggt      240
cgtgaaacat gctactttt tgatgatgct gcctcacctg ctgggactgg ggagttgaat      300
gaagcaccat cagctaataa ttttattat gaaaaagttt gccttccagc tatctctgct      360
catgaagcat gtacttatag atcatttca tttgaaagaa ctagaaatac tcaattagaa      420
ggttttgtta aaaatcact acaagttaca tcacgtgaag aatgcctttc tacatgttta      480
aaagaaagtg aatttgtatg tagatcagtt aactataatt atgaaaactt tatgtgtgaa      540 cttcaacag aaagatcgcg ttctaaacca caaatatga gaatgtcagc agctccagtt      600
gattattatg ataataattg tttaaataga caaaatagat gtggtgaatc tggtggaaat      660 ttgatttta ttaaaacaac acaatttgaa attcattatt atgatcatac tcaatcaatg      720
gaagcacaag aatcattctg tttacaaaaa tgtttagatt cattaaacac cttctgtaga      780
tctgttgaat attctccatc tgaaaaaaat tgtattgttt ctgatgaaga tacatattca      840
agagctgatc aacaaggtga agttaataat aaagattatt atgaacctgt ttgtgttgct      900
gctgatctta gttcatctac atgtcgtcaa caagctgctt ttgaaagatt tattggttct      960
gctattgaag gtaccccagt tgctacagca caacaagtaa ccatttctga ttgtatttca     1020 cttgtttcc aaaatttgaa ttgtaaatca attaattatg atcgtacaca atctacatgt     1080
tatatttatg ctgttggaag acaagaatct aatgttaaaa atgatgcaag tttcgattat     1140
tatgaattta caattattga taatggatgc caagatatc ctgctcttgt agggccagtt     1200
ttacaagatt tcgacaaaaa tcgtcttaaa tctgaaatga aagcattccg tttagatgga     1260
tcatatgata ttcaaattga atgttctgtt atgttttgtg ctggtccaat gggttgtcca     1320
ccatctaatt gccttgattc aggaacaaat gaattatttg cttcacatgg aagaaagaaa     1380
agaagtattg ttgattcaa aaatacaaca acatctgcag aaacattatc tgctataatt     1440
agagtacttg ctgctggaga agaagaatta gaagttgaag aattttatag aaatgatact     1500
aattttaaat atgattctga agaaaatatc tcagctcata acttatactg tatgtctgaa     1560
atgtggtttg tatcaggaat tgtttcaatg gctatgatct gtcttcttct ttctgttctt     1620
atagttatgt ggggctgtca ttcattaaat caatcttcaa attaccaat gtga           1674

<210> SEQ ID NO 7
<211> LENGTH: 3847
<212> TYPE: DNA
<213> ORGANISM: Meloidogyne javanica
<220> FEATURE:
<221> NAME/KEY: CDS
<222> LOCATION: (181)...(3810)

<400> SEQUENCE: 7
gcgtcgatag tccgattttt taaggtttaa ttacccaagc ttaaggaata tttgaagctt       60 attttttaaag aaaaataaa ttaataaga gattagcaca acaacaacag aaattttct        120 tgaatttaca acaaaataat ttttttcttaa ttaaattcct ttaaattatc cacaacttct     180 atg gtt aca aaa atc cca act ttt ccc ctc ctt ttt att ttc cca ttt        228
Met Val Thr Lys Ile Pro Thr Phe Pro Leu Leu Phe Ile Phe Pro Phe
  1               5                  10                  15 tta ttt aca ttt tta acg aca aaa tgt cag gct tat tct ata cca tta        276
Leu Phe Thr Phe Leu Thr Thr Lys Cys Gln Ala Tyr Ser Ile Pro Leu
             20                  25                  30 ata tca gaa tgt aat tcg gaa gaa gcc cca gtt ttt ctt ttg caa cgg        324
Ile Ser Glu Cys Asn Ser Glu Glu Ala Pro Val Phe Leu Leu Gln Arg
         35                  40                  45
```

```
aat gtt tct tct atc gcc gga act gag cct tta aga act gtt cct gtt      372
Asn Val Ser Ser Ile Ala Gly Thr Glu Pro Leu Arg Thr Val Pro Val
    50              55                  60 aca ggg gga ttt ttg gaa tgt gcg gaa ctt tgt tca gca gca aat aat      420
Thr Gly Gly Phe Leu Glu Cys Ala Glu Leu Cys Ser Ala Ala Asn Asn
65              70                  75                  80 tgt gtt gct gtt aaa ttt tct att gaa aaa caa tgc caa ttg ttg ggg      468
Cys Val Ala Val Lys Phe Ser Ile Glu Lys Gln Cys Gln Leu Leu Gly
                85                  90                  95 aaa aca act atg aca gca aca act tta tct tta caa gac att aat ttg      516
Lys Thr Thr Met Thr Ala Thr Thr Leu Ser Leu Gln Asp Ile Asn Leu
            100                 105                 110 aca cta gct aga tta gct act aaa agt tgt gtt aag agc aaa aaa atc      564
Thr Leu Ala Arg Leu Ala Thr Lys Ser Cys Val Lys Ser Lys Lys Ile
        115                 120                 125 tgt tct tcc ccc ttc cat ttt gat gtt cac gaa caa aaa ata ctt gtt      612
Cys Ser Ser Pro Phe His Phe Asp Val His Glu Gln Lys Ile Leu Val
130             135                 140 ggt ttt gct aga gaa gtt gta tca gca gaa tct ata cat caa tgt tta      660
Gly Phe Ala Arg Glu Val Val Ser Ala Glu Ser Ile His Gln Cys Leu
145             150                 155                 160 act gct tgt tta gat gct gtt gat act ttt ggc ttt gaa tgc gag tca      708
Thr Ala Cys Leu Asp Ala Val Asp Thr Phe Gly Phe Glu Cys Glu Ser
                165                 170                 175 gta atg tat tat cca ttg gat gcc gaa tgt att tta aat aca gaa gac      756
Val Met Tyr Tyr Pro Leu Asp Ala Glu Cys Ile Leu Asn Thr Glu Asp
            180                 185                 190 aga ctt gac cgt cca gat ttg ttt gtt gat gag aag gaa gat act gtt      804
Arg Leu Asp Arg Pro Asp Leu Phe Val Asp Glu Lys Glu Asp Thr Val
        195                 200                 205 gtt tat ttg gat aat aat tgt gct gga tcc caa tgt cat gcc cct tat      852
Val Tyr Leu Asp Asn Asn Cys Ala Gly Ser Gln Cys His Ala Pro Tyr
210                 215                 220 gta acc caa tat gta gct gtt gaa gga aaa caa tta gct gag gaa ttg      900
Val Thr Gln Tyr Val Ala Val Glu Gly Lys Gln Leu Ala Glu Glu Leu
225             230                 235                 240 gat cat aat ttt gag gga atg gag ttg aca gaa tgt gaa cag ctt tgt      948
Asp His Asn Phe Glu Gly Met Glu Leu Thr Glu Cys Glu Gln Leu Cys
                245                 250                 255 aat caa aga ttg agt gtt tct gca aat gac ttt aat tgc aaa gca ttt      996
Asn Gln Arg Leu Ser Val Ser Ala Asn Asp Phe Asn Cys Lys Ala Phe
            260                 265                 270 atg tac aat aac caa aca aga tct tgt att ctt tct gat gaa cgt tca     1044
Met Tyr Asn Asn Gln Thr Arg Ser Cys Ile Leu Ser Asp Glu Arg Ser
        275                 280                 285 aga cct ttg ggt aga gct aat ttg aca gat gct aaa gga tgg act tat     1092
Arg Pro Leu Gly Arg Ala Asn Leu Thr Asp Ala Lys Gly Trp Thr Tyr
290                 295                 300 cac gag aaa aaa tgt ttt gcc tcc cca cgt aca tgc cga aat gtt cct     1140
His Glu Lys Lys Cys Phe Ala Ser Pro Arg Thr Cys Arg Asn Val Pro
305             310                 315                 320 tct ttt acc cgc gtc cct caa atg tta tta gtt gga ttt gcc tct ttt     1188
Ser Phe Thr Arg Val Pro Gln Met Leu Leu Val Gly Phe Ala Ser Phe
                325                 330                 335 gta atg gaa aat gtc cct tca gta act atg tgt ttg gat caa tgt aca     1236
Val Met Glu Asn Val Pro Ser Val Thr Met Cys Leu Asp Gln Cys Thr
            340                 345                 350 aat cct ccc cca gaa act gga caa agt ttt gtt tgt aaa tct gtc atg     1284
Asn Pro Pro Pro Glu Thr Gly Gln Ser Phe Val Cys Lys Ser Val Met
        355                 360                 365
```

```
                                                              -continued tat tat tat aat gag caa gaa tgt att tta aat gct gaa tca cgt cat      1332
Tyr Tyr Tyr Asn Glu Gln Glu Cys Ile Leu Asn Ala Glu Ser Arg His
        370                 375                 380 tcc aag cca gat tta ttt att ccc gaa gaa gac gat ttt gtt gta gat      1380
Ser Lys Pro Asp Leu Phe Ile Pro Glu Glu Asp Asp Phe Val Val Asp
385                 390                 395                 400 tat ttt gat ata aat tgc cgt cta gaa caa gaa caa tgt atc gat gga      1428
Tyr Phe Asp Ile Asn Cys Arg Leu Glu Gln Glu Gln Cys Ile Asp Gly
            405                 410                 415 aga acg ccc caa tta gtt aga aca att aat tct gca ctt cca gaa ggg      1476
Arg Thr Pro Gln Leu Val Arg Thr Ile Asn Ser Ala Leu Pro Glu Gly
        420                 425                 430 gag ggg tct ata cat gtt ttg gaa aca att aag gga gga gtt cag caa      1524
Glu Gly Ser Ile His Val Leu Glu Thr Ile Lys Gly Gly Val Gln Gln
    435                 440                 445 tgt gct aaa aaa tgt tct gaa cgc gcc cca gac aaa tgt cgc tct ttc      1572
Cys Ala Lys Lys Cys Ser Glu Arg Ala Pro Asp Lys Cys Arg Ser Phe
450                 455                 460 aat ttt gat aaa caa gct ggt aat tgt aat tta ctt tat ttg gat gga      1620
Asn Phe Asp Lys Gln Ala Gly Asn Cys Asn Leu Leu Tyr Leu Asp Gly
465                 470                 475                 480 caa ggg tct tta cga cca gag caa aag aca caa ttc gat tta tac gat      1668
Gln Gly Ser Leu Arg Pro Glu Gln Lys Thr Gln Phe Asp Leu Tyr Asp
            485                 490                 495 gtt cat tgt ttg agt gga aca tct caa ctt tta gga gaa aat tct aaa      1716
Val His Cys Leu Ser Gly Thr Ser Gln Leu Leu Gly Glu Asn Ser Lys
        500                 505                 510 cat tct ccc tct gct tgt gtt gac cca gaa ggg gct att ttt agt cgt      1764
His Ser Pro Ser Ala Cys Val Asp Pro Glu Gly Ala Ile Phe Ser Arg
    515                 520                 525 ttc ctc tac act cgt tgg gta gca aat tct ccc aat cgt gaa att tca      1812
Phe Leu Tyr Thr Arg Trp Val Ala Asn Ser Pro Asn Arg Glu Ile Ser
530                 535                 540 agt tta cca ctt tcc aaa tgt tta aat ctt tgt tcg gtt gga gga gaa      1860
Ser Leu Pro Leu Ser Lys Cys Leu Asn Leu Cys Ser Val Gly Gly Glu
545                 550                 555                 560 caa tgt gag ggt gtt aat tac aat cgc cga aat ggt tct tgt caa tta      1908
Gln Cys Glu Gly Val Asn Tyr Asn Arg Arg Asn Gly Ser Cys Gln Leu
            565                 570                 575 ttt act tcc ctt cta tta aac tct tct cca aat tct caa caa gac aaa      1956
Phe Thr Ser Leu Leu Leu Asn Ser Ser Pro Asn Ser Gln Gln Asp Lys
        580                 585                 590 gac gaa cat gtt gat ttt tac aga aat att tgt aga gtt aag gaa tcg      2004
Asp Glu His Val Asp Phe Tyr Arg Asn Ile Cys Arg Val Lys Glu Ser
    595                 600                 605 aaa agt gat agt ggg gct gct aat gta ccc aaa aca caa caa gca acg      2052
Lys Ser Asp Ser Gly Ala Ala Asn Val Pro Lys Thr Gln Gln Ala Thr
610                 615                 620 gct gca cct ccc cct tct gtt caa tta act act aaa cct cca caa att      2100
Ala Ala Pro Pro Pro Ser Val Gln Leu Thr Thr Lys Pro Pro Gln Ile
625                 630                 635                 640 cgt gat tta aac aac aac aat aaa aca aca cac aaa gaa cca aat att      2148
Arg Asp Leu Asn Asn Asn Asn Lys Thr Thr His Lys Glu Pro Asn Ile
            645                 650                 655 aaa ctt cca cca caa tca gca aaa cct ata aat gga aaa act gga aag      2196
Lys Leu Pro Pro Gln Ser Ala Lys Pro Ile Asn Gly Lys Thr Gly Lys
        660                 665                 670 gaa caa ctt cct gta ggg tca aaa tct ttt ggg gtt act aat acg cgt      2244
Glu Gln Leu Pro Val Gly Ser Lys Ser Phe Gly Val Thr Asn Thr Arg
```

-continued

```
                675             680             685
gat gat ggg gag aat tca ata act gga act gct cct cct cct gta gat    2292
Asp Asp Gly Glu Asn Ser Ile Thr Gly Thr Ala Pro Pro Pro Val Asp
690             695             700 ggc aaa tta att att aaa cct tca cca caa gtt tct att ccc tcc cct    2340
Gly Lys Leu Ile Ile Lys Pro Ser Pro Gln Val Ser Ile Pro Ser Pro
705             710             715             720 gta ctt att ccg gca caa gaa gta cat act att tgt aat tat gaa gga    2388
Val Leu Ile Pro Ala Gln Glu Val His Thr Ile Cys Asn Tyr Glu Gly
            725             730             735 att agt gtt caa att aaa cat tct tct cca ttc tct ggc gtt gtt ttt    2436
Ile Ser Val Gln Ile Lys His Ser Ser Pro Phe Ser Gly Val Val Phe
            740             745             750 gtt cga aat aaa tat gat act tgc cgt gtg aag ttg aag gaa agg aca    2484
Val Arg Asn Lys Tyr Asp Thr Cys Arg Val Lys Leu Lys Glu Arg Thr
            755             760             765 gcg ttg ttt tgg ttt tgg ggc ttc cag caa att ttg gaa atg aag cca    2532
Ala Leu Phe Trp Phe Trp Gly Phe Gln Gln Ile Leu Glu Met Lys Pro
770             775             780 att gct tta att aat tca caa aaa cat gga aaa ggg aat aaa aca cac    2580
Ile Ala Leu Ile Asn Ser Gln Lys His Gly Lys Gly Asn Lys Thr His
785             790             795             800 gga gat act tta ctt tct att gaa ggt tcc aaa aaa caa att gaa ggg    2628
Gly Asp Thr Leu Leu Ser Ile Glu Gly Ser Lys Lys Gln Ile Glu Gly
            805             810             815 ggt tct tca act gaa gat att caa tta ata aat tct caa aaa gac ctt    2676
Gly Ser Ser Thr Glu Asp Ile Gln Leu Ile Asn Ser Gln Lys Asp Leu
            820             825             830 aaa cgt tca aga aga caa tta caa aga gat tgt gga tta caa gat atg    2724
Lys Arg Ser Arg Arg Gln Leu Gln Arg Asp Cys Gly Leu Gln Asp Met
            835             840             845 gac aat gga act tac aaa act gtt att gtt gtc caa aca aat aat ttg    2772
Asp Asn Gly Thr Tyr Lys Thr Val Ile Val Val Gln Thr Asn Asn Leu
850             855             860 gga att ccg gga ctt gtt act tct atg gac caa ctt tat gag att tcc    2820
Gly Ile Pro Gly Leu Val Thr Ser Met Asp Gln Leu Tyr Glu Ile Ser
865             870             875             880 tgt aac tat tca agt atg ttg gga ggc aaa gtc caa aca gca gct gca    2868
Cys Asn Tyr Ser Ser Met Leu Gly Gly Lys Val Gln Thr Ala Ala Ala
            885             890             895 tta cgt gtt cac ggt ccc caa cct tca cta atc cag cct cgc ggc aaa    2916
Leu Arg Val His Gly Pro Gln Pro Ser Leu Ile Gln Pro Arg Gly Lys
            900             905             910 ata gaa ttg gga aat cct gtt ttg atg caa atg ggg cct gta cgt agt    2964
Ile Glu Leu Gly Asn Pro Val Leu Met Gln Met Gly Pro Val Arg Ser
            915             920             925 gaa agg caa agt ggg gaa ggg cct tta att caa gct aaa ttg ggg gat    3012
Glu Arg Gln Ser Gly Glu Gly Pro Leu Ile Gln Ala Lys Leu Gly Asp
930             935             940 att ctt gaa tta aaa tgg gaa att atg gca atg gat gaa gaa ttg gac    3060
Ile Leu Glu Leu Lys Trp Glu Ile Met Ala Met Asp Glu Glu Leu Asp
945             950             955             960 ttt tta gtt cgt gat tgt ttt gca gag ccg gga act tct gga aat caa    3108
Phe Leu Val Arg Asp Cys Phe Ala Glu Pro Gly Thr Ser Gly Asn Gln
            965             970             975 ggg gaa aga ctt cct tta att gag aat ggt tgt cca aca cca gca gta    3156
Gly Glu Arg Leu Pro Leu Ile Glu Asn Gly Cys Pro Thr Pro Ala Val
            980             985             990 gca caa aaa tta att cca aat cca ata aaa gca att aat tct gca gtt    3204
```

-continued

| | |
|---|---|
| Ala Gln Lys Leu Ile Pro Asn Pro Ile Lys Ala Ile Asn Ser Ala Val<br>        995                 1000                 1005 | |
| aaa tta act tat tta caa gca ttc aga ttt gac agt tct cca gct att<br>Lys Leu Thr Tyr Leu Gln Ala Phe Arg Phe Asp Ser Ser Pro Ala Ile<br>1010               1015               1020 | 3252 |
| aga ata act tgt cat tta gaa tta tgt aaa gaa aat tgt aaa tcg gtt<br>Arg Ile Thr Cys His Leu Glu Leu Cys Lys Glu Asn Cys Lys Ser Val<br>1025               1030               1035               1040 | 3300 |
| aat tgt aaa ttt aat gat gga att aaa gaa tcg tgg ggc aga aaa cgc<br>Asn Cys Lys Phe Asn Asp Gly Ile Lys Glu Ser Trp Gly Arg Lys Arg<br>                 1045               1050               1055 | 3348 |
| cgt ttt gct att gac aat aac att aat agg aaa aat gaa gtt aaa gaa<br>Arg Phe Ala Ile Asp Asn Asn Ile Asn Arg Lys Asn Glu Val Lys Glu<br>                 1060               1065               1070 | 3396 |
| ttc gaa act cgc cgt ttt gtc gtt ccc cgt ttt gcc caa gca aca act<br>Phe Glu Thr Arg Arg Phe Val Val Pro Arg Phe Ala Gln Ala Thr Thr<br>                 1075               1080               1085 | 3444 |
| tct tta gtt att gta gac cct tta caa caa caa aat tct gtt ata aaa<br>Ser Leu Val Ile Val Asp Pro Leu Gln Gln Gln Asn Ser Val Ile Lys<br>1090               1095               1100 | 3492 |
| aca gaa caa caa caa caa cca ttt att tca cat tcc tca ata tct aaa<br>Thr Glu Gln Gln Gln Gln Pro Phe Ile Ser His Ser Ser Ile Ser Lys<br>1105               1110               1115               1120 | 3540 |
| caa ata ttt gaa aat aat aaa aaa gaa aat aat aaa aat ata aca aaa<br>Gln Ile Phe Glu Asn Asn Lys Lys Glu Asn Asn Lys Asn Ile Thr Lys<br>                 1125               1130               1135 | 3588 |
| aca gct aaa aaa tcc tct tct ctt ttt gaa gct ttt act gag gct gct<br>Thr Ala Lys Lys Ser Ser Ser Leu Phe Glu Ala Phe Thr Glu Ala Ala<br>                 1140               1145               1150 | 3636 |
| ggt gga agg aaa att aat tta gaa tta aca aca aca aat tca gaa caa<br>Gly Gly Arg Lys Ile Asn Leu Glu Leu Thr Thr Thr Asn Ser Glu Gln<br>                 1155               1160               1165 | 3684 |
| caa caa ctt tgt tta cat aaa tgg aca ctt ggg ggt gtt ttt gga act<br>Gln Gln Leu Cys Leu His Lys Trp Thr Leu Gly Gly Val Phe Gly Thr<br>        1170               1175               1180 | 3732 |
| ctt tta aca tta att gtt gtt caa agc ggg gtt gct gct aaa cat tta<br>Leu Leu Thr Leu Ile Val Val Gln Ser Gly Val Ala Ala Lys His Leu<br>1185               1190               1195               1200 | 3780 |
| att aat cga ttt att gtt gga aaa aga att taaaaaaaaa aaaaaaagta<br>Ile Asn Arg Phe Ile Val Gly Lys Arg Ile<br>                 1205               1210 | 3830 |
| ctagtcgacg cgtggcc | 3847 |

<210> SEQ ID NO 8
<211> LENGTH: 752
<212> TYPE: DNA
<213> ORGANISM: Heterodera glycines
<220> FEATURE:
<221> NAME/KEY: CDS
<222> LOCATION: (1)...(750)

<400> SEQUENCE: 8

| | |
|---|---|
| gag cag aag att ttg gtg ggt ttc gcg cgg gag gtg gtc tcc gcc gac<br>Glu Gln Lys Ile Leu Val Gly Phe Ala Arg Glu Val Val Ser Ala Asp<br> 1              5                 10                15 | 48 |
| tca gtc cac cgc tgt ctg tcc gct tgt ctg aat gcg ttc gat acg ttc<br>Ser Val His Arg Cys Leu Ser Ala Cys Leu Asn Ala Phe Asp Thr Phe<br>               20                 25                30 | 96 |
| ggc ttc gaa tgc gag tcg gtc atg tat tac cct gtg gac gcg gaa tgc<br>Gly Phe Glu Cys Glu Ser Val Met Tyr Tyr Pro Val Asp Ala Glu Cys<br>           35                 40                45 | 144 |

```
att ttg aac acg gag gac cga ttg gat cgg cct gac ctt ttc gtg gac      192
Ile Leu Asn Thr Glu Asp Arg Leu Asp Arg Pro Asp Leu Phe Val Asp
    50                  55                  60 gag cac gag gac acg gtc atc tac ttg gac aac aat tgc gcc gga tgt      240
Glu His Glu Asp Thr Val Ile Tyr Leu Asp Asn Asn Cys Ala Gly Cys
65                  70                  75                  80 gag tgc cat tgg cat ttt gac aat ttc aaa aca agc ggc att ttg aac      288
Glu Cys His Trp His Phe Asp Asn Phe Lys Thr Ser Gly Ile Leu Asn
                85                  90                  95 gac caa caa ttc gca att gca gca caa tgt tac gca ccg tac gta acg      336
Asp Gln Gln Phe Ala Ile Ala Ala Gln Cys Tyr Ala Pro Tyr Val Thr
            100                 105                 110 caa tac gtg gcg gtg gaa gga cgc caa ttg tcg gac gaa ttg gac cac      384
Gln Tyr Val Ala Val Glu Gly Arg Gln Leu Ser Asp Glu Leu Asp His
        115                 120                 125 agt ttt gaa ggg ttg gag ctg agc gaa tgt gaa gag ttg tgc acg caa      432
Ser Phe Glu Gly Leu Glu Leu Ser Glu Cys Glu Glu Leu Cys Thr Gln
    130                 135                 140 cgg tta agt gtt acg gca aac gac ttc aac tgc aaa tcg ttc atg tac      480
Arg Leu Ser Val Thr Ala Asn Asp Phe Asn Cys Lys Ser Phe Met Tyr
145                 150                 155                 160 agt aac ttg acg cgc agt tgc gtt ttg tcg gac gaa cgc tcg cgc cct      528
Ser Asn Leu Thr Arg Ser Cys Val Leu Ser Asp Glu Arg Ser Arg Pro
                165                 170                 175 ttg ggc cgt gcc aat ttg gcc gaa gtg ccg gga tgg act tat ttc gag      576
Leu Gly Arg Ala Asn Leu Ala Glu Val Pro Gly Trp Thr Tyr Phe Glu
            180                 185                 190 agc cgc ggc gtt ccg tcg ttt acg cga gtg ccg caa atg ctt ttg gtg      624
Ser Arg Gly Val Pro Ser Phe Thr Arg Val Pro Gln Met Leu Leu Val
        195                 200                 205 ggc ttt gcc tct ttt gtg atg gaa aat gtg ccg tca gtg aca atg tgt      672
Gly Phe Ala Ser Phe Val Met Glu Asn Val Pro Ser Val Thr Met Cys
    210                 215                 220 ttg gac caa tgc aca agc cct cct cct gag acg gga caa aac ttt gtg      720
Leu Asp Gln Cys Thr Ser Pro Pro Pro Glu Thr Gly Gln Asn Phe Val
225                 230                 235                 240 tgt aaa tcg gtg atg tac tac tac aac gag ca                           752
Cys Lys Ser Val Met Tyr Tyr Tyr Asn Glu
                245                 250

<210> SEQ ID NO 9
<211> LENGTH: 2808
<212> TYPE: DNA
<213> ORGANISM: Brugia malayi
<220> FEATURE:
<221> NAME/KEY: CDS
<222> LOCATION: (166)...(2808)

<400> SEQUENCE: 9
cgactggagc acgaggacac tgacatggac tgaaggagta gaaaatttct gttgttcatt     60
tcttatcaga ctgtcccatt catcatcgtg accactacca gtattacttc aggacagtaa    120
tattcgggta aatttcggct gctcaatcgg taggaccgct ttaat atg cat ctt tcc    177
                                                 Met His Leu Ser
                                                   1 aac cat gcc tca tca ctt ctg cat tac tat tca cat ctc atc ata att      225
Asn His Ala Ser Ser Leu Leu His Tyr Tyr Ser His Leu Ile Ile Ile
  5                  10                  15                  20 gca tac ttt tct gta ttt gct tca atc gaa ata caa gaa att cca tca      273
Ala Tyr Phe Ser Val Phe Ala Ser Ile Glu Ile Gln Glu Ile Pro Ser
                25                  30                  35
```

-continued

| | |
|---|---|
| tat cca gca tgt agc aat ggc gaa tca cct gtc ttt tta ctc caa cac<br>Tyr Pro Ala Cys Ser Asn Gly Glu Ser Pro Val Phe Leu Leu Gln His<br>             40                           45                     50 | 321 |
| aat gct aca gca ggt aat gtt ctg aag cga gct tca act tca cat ctg<br>Asn Ala Thr Ala Gly Asn Val Leu Lys Arg Ala Ser Thr Ser His Leu<br> 55                           60                          65 | 369 |
| gtc gac tgc act gac ctt tgt tca gct aac gat gaa tgt ttg gcg ata<br>Val Asp Cys Thr Asp Leu Cys Ser Ala Asn Asp Glu Cys Leu Ala Ile<br>       70                      75                     80 | 417 |
| acc tat gaa gat aaa gaa tgc aaa atg ttg tca agc att gga gaa tcg<br>Thr Tyr Glu Asp Lys Glu Cys Lys Met Leu Ser Ser Ile Gly Glu Ser<br> 85                           90                        95                100 | 465 |
| aca gga cat tta aat gat tat gta ttg ctg agt aaa aat tgt gct aaa<br>Thr Gly His Leu Asn Asp Tyr Val Leu Leu Ser Lys Asn Cys Ala Lys<br>                      105                     110                     115 | 513 |
| agt gcg cgg atc tgc tca tcg cca ttt caa ttc gat gta cac aga caa<br>Ser Ala Arg Ile Cys Ser Ser Pro Phe Gln Phe Asp Val His Arg Gln<br>            120                     125                     130 | 561 |
| aaa att ttg gtt ggg ttt gct cgc gag gtt gtg tca gct gat tca tta<br>Lys Ile Leu Val Gly Phe Ala Arg Glu Val Val Ser Ala Asp Ser Leu<br>135                          140                     145 | 609 |
| tcg tta tgt cta tca gct tgc ttg aat gca ttt gat tct ttc ggt ttt<br>Ser Leu Cys Leu Ser Ala Cys Leu Asn Ala Phe Asp Ser Phe Gly Phe<br>          150                     155                     160 | 657 |
| gaa tgt gag tcg gta atg tac tat cca gtt gat tca gaa tgc atc cta<br>Glu Cys Glu Ser Val Met Tyr Tyr Pro Val Asp Ser Glu Cys Ile Leu<br>165                          170                     175                180 | 705 |
| aac acc gaa gat cgt ctg gat cga cct gac ttg ttt ggg gat gaa tta<br>Asn Thr Glu Asp Arg Leu Asp Arg Pro Asp Leu Phe Gly Asp Glu Leu<br>                     185                     190                     195 | 753 |
| gat gat aac gtc att tat ttg gat aac aac tgt gct gga tca cag tgt<br>Asp Asp Asn Val Ile Tyr Leu Asp Asn Asn Cys Ala Gly Ser Gln Cys<br>          200                     205                     210 | 801 |
| tat gct cca tac ata aca caa tac att gcc gtc gca aat cgt cag cta<br>Tyr Ala Pro Tyr Ile Thr Gln Tyr Ile Ala Val Ala Asn Arg Gln Leu<br>            215                     220                     225 | 849 |
| gct aac gag ttg gac aga caa ctg atc gct gat cgt gaa tca tgc gag<br>Ala Asn Glu Leu Asp Arg Gln Leu Ile Ala Asp Arg Glu Ser Cys Glu<br>230                          235                     240 | 897 |
| tcg tta tgt act cag cga ctg tct aca acg aca aac gat ttc aac tgt<br>Ser Leu Cys Thr Gln Arg Leu Ser Thr Thr Thr Asn Asp Phe Asn Cys<br>245                          250                     255                260 | 945 |
| aaa tca ttt atg cat aat ccg gaa act aac gtt tgc ata ctt tct gat<br>Lys Ser Phe Met His Asn Pro Glu Thr Asn Val Cys Ile Leu Ser Asp<br>                  265                     270                     275 | 993 |
| gaa cgt tct aaa cca ctt ggt cga ggc aat cta gtg aaa gct gac ggt<br>Glu Arg Ser Lys Pro Leu Gly Arg Gly Asn Leu Val Lys Ala Asp Gly<br>            280                     285                     290 | 1041 |
| ttc aca tat tat gag aag aaa tgt ttt gca tca cca cga aca tgt cgc<br>Phe Thr Tyr Tyr Glu Lys Lys Cys Phe Ala Ser Pro Arg Thr Cys Arg<br>               295                     300                     305 | 1089 |
| aat gta ccg tcg ttt gag cgc ata cct cag atg ata ctt gtt ggt ttt<br>Asn Val Pro Ser Phe Glu Arg Ile Pro Gln Met Ile Leu Val Gly Phe<br>310                          315                     320 | 1137 |
| gct gca ttt gtt atg gaa aat gta cct tca gta acg atg tgc ctc gat<br>Ala Ala Phe Val Met Glu Asn Val Pro Ser Val Thr Met Cys Leu Asp<br>325                          330                     335                340 | 1185 |
| cag tgc aca aat cct cca ccg gaa act gga gaa aat ttc gaa tgc aaa<br>Gln Cys Thr Asn Pro Pro Pro Glu Thr Gly Glu Asn Phe Glu Cys Lys | 1233 |

-continued

```
                345                   350                   355
tct gtg atg tat tat tat aac gaa cag gaa tgt att tta aac gct gaa       1281
Ser Val Met Tyr Tyr Tyr Asn Glu Gln Glu Cys Ile Leu Asn Ala Glu
            360                   365                   370 aca cga gaa aat aaa tcg gaa ttg ttt ata ccg gag gga gaa gaa ttc       1329
Thr Arg Glu Asn Lys Ser Glu Leu Phe Ile Pro Glu Gly Glu Glu Phe
        375                   380                   385 caa gtc gat tat ttt gat atc act tgt cat ctg cgc cct gaa aca tgt       1377
Gln Val Asp Tyr Phe Asp Ile Thr Cys His Leu Arg Pro Glu Thr Cys
    390                   395                   400 cca aat ggc aca aca tta cat act gta cgt acg gtt aat gca gca ctc       1425
Pro Asn Gly Thr Thr Leu His Thr Val Arg Thr Val Asn Ala Ala Leu
405                   410                   415                   420 cct gaa ggc gaa gga tcg atc cat att ttg cag tca gcc ggg aat tcg       1473
Pro Glu Gly Glu Gly Ser Ile His Ile Leu Gln Ser Ala Gly Asn Ser
                    425                   430                   435 gtt gct gat tgc atg aca aaa tgt tac gag atg gct ccc gag aaa tgt       1521
Val Ala Asp Cys Met Thr Lys Cys Tyr Glu Met Ala Pro Glu Lys Cys
                440                   445                   450 cgc gca ttc aat ttt gat aag cag aca tct gac tgt gac ctg ctg tac       1569
Arg Ala Phe Asn Phe Asp Lys Gln Thr Ser Asp Cys Asp Leu Leu Tyr
            455                   460                   465 gtt gat ggg aag aca acc tta cga cca gca gtc cac tcg ggc att gat       1617
Val Asp Gly Lys Thr Thr Leu Arg Pro Ala Val His Ser Gly Ile Asp
    470                   475                   480 ctc tac gac ctt cat tgc cta gag cag aca aaa gtt tgc gct cag aaa       1665
Leu Tyr Asp Leu His Cys Leu Glu Gln Thr Lys Val Cys Ala Gln Lys
485                   490                   495                   500 aac aac gta aca cga ttt tcg aga tat ttg tac agt ata tat gat gca       1713
Asn Asn Val Thr Arg Phe Ser Arg Tyr Leu Tyr Ser Ile Tyr Asp Ala
                    505                   510                   515 gtg cca tcg caa ttc tac gaa gca act gcc ctc aca aat tgt ctt aat       1761
Val Pro Ser Gln Phe Tyr Glu Ala Thr Ala Leu Thr Asn Cys Leu Asn
                520                   525                   530 ctt tgc gca tat acc gag cgt tgc gaa ggt gta aat tac aac aga agg       1809
Leu Cys Ala Tyr Thr Glu Arg Cys Glu Gly Val Asn Tyr Asn Arg Arg
            535                   540                   545 aat ggt cgt tgt gaa tta ttt gat aag gtc gaa gga aat gga aag cca       1857
Asn Gly Arg Cys Glu Leu Phe Asp Lys Val Glu Gly Asn Gly Lys Pro
    550                   555                   560 agt gat ttc acg gat ttt tac aaa aat ctt tgt ctg gtg gaa gaa gta       1905
Ser Asp Phe Thr Asp Phe Tyr Lys Asn Leu Cys Leu Val Glu Glu Val
565                   570                   575                   580 gaa tca gaa tat agc gcc gca gct aat gtt ccc aaa cat ctc ctt ccg       1953
Glu Ser Glu Tyr Ser Ala Ala Ala Asn Val Pro Lys His Leu Leu Pro
                    585                   590                   595 aat gtt tca cat tct gca gtt act cag aaa caa gaa gct aaa tta cac       2001
Asn Val Ser His Ser Ala Val Thr Gln Lys Gln Glu Ala Lys Leu His
                600                   605                   610 att atc tca gca aaa aca aag cct ttc cta cgc gaa cag gaa gca cag       2049
Ile Ile Ser Ala Lys Thr Lys Pro Phe Leu Arg Glu Gln Glu Ala Gln
            615                   620                   625 cga cga gct cca gaa aca ata aca gcg aag tcg tct tca gct tcc gga       2097
Arg Arg Ala Pro Glu Thr Ile Thr Ala Lys Ser Ser Ser Ala Ser Gly
    630                   635                   640 aaa gta agt ggt gaa gca gga tca tca act aca ttc agc att tct tca       2145
Lys Val Ser Gly Glu Ala Gly Ser Ser Thr Thr Phe Ser Ile Ser Ser
645                   650                   655                   660 tcc gga agg ctt cca ggg cca gta gtc caa att gct cca aat gca gtg       2193
```

-continued

```
Ser Gly Arg Leu Pro Gly Pro Val Val Gln Ile Ala Pro Asn Ala Val
            665                 670                 675 caa aca gtt tgc aat tat gaa ggc atc aaa gtg cag atg gag aac ccc      2241
Gln Thr Val Cys Asn Tyr Glu Gly Ile Lys Val Gln Met Glu Asn Pro
            680                 685                 690 aaa gcc ttt tcg gga gtg ata ttt gtt aaa aat agg tat gaa acc tgt      2289
Lys Ala Phe Ser Gly Val Ile Phe Val Lys Asn Arg Tyr Glu Thr Cys
            695                 700                 705 cga gta gag gtt acg gat agt gaa agt gca cca cta gta att ggt tta      2337
Arg Val Glu Val Thr Asp Ser Glu Ser Ala Pro Leu Val Ile Gly Leu
            710                 715                 720 cca ccg aat ttt ggt tca aaa atg gta gct gat gaa aag gtt gcc gca      2385
Pro Pro Asn Phe Gly Ser Lys Met Val Ala Asp Glu Lys Val Ala Ala
725                 730                 735                 740 agc gaa gca aat att caa cca gaa ata tcc gga ggc gac aaa ctg gat      2433
Ser Glu Ala Asn Ile Gln Pro Glu Ile Ser Gly Gly Asp Lys Leu Asp
            745                 750                 755 aaa ccc gct gat gaa ctg cgc ata aga cga caa gct tta gag cta cac      2481
Lys Pro Ala Asp Glu Leu Arg Ile Arg Arg Gln Ala Leu Glu Leu His
            760                 765                 770 aga gat tgc gga atc cag gat atg aac aat ggt act tat aaa tca acg      2529
Arg Asp Cys Gly Ile Gln Asp Met Asn Asn Gly Thr Tyr Lys Ser Thr
            775                 780                 785 gtg gtt gta caa aca aat aac ttg ggt ata cct gga ctg gta act tcc      2577
Val Val Val Gln Thr Asn Asn Leu Gly Ile Pro Gly Leu Val Thr Ser
            790                 795                 800 atg gat cag att ttt gaa gtg agc tgt gat tat agt tca atg ctt ggt      2625
Met Asp Gln Ile Phe Glu Val Ser Cys Asp Tyr Ser Ser Met Leu Gly
805                 810                 815                 820 gga aaa gtt act gct ggt gcc aat ctc aca att gat ggt ccc gaa gca      2673
Gly Lys Val Thr Ala Gly Ala Asn Leu Thr Ile Asp Gly Pro Glu Ala
            825                 830                 835 tct ctt att caa ccc cga gga aaa atc gaa ctt ggt aac ccg gtg ctt      2721
Ser Leu Ile Gln Pro Arg Gly Lys Ile Glu Leu Gly Asn Pro Val Leu
            840                 845                 850 atg cag atg ttg agt gga caa gga gaa cct gtc cta caa gca aaa cta      2769
Met Gln Met Leu Ser Gly Gln Gly Glu Pro Val Leu Gln Ala Lys Leu
            855                 860                 865 ggt gac att ctg cag cta cga tgg gaa atc atg gcg atg                  2808
Gly Asp Ile Leu Gln Leu Arg Trp Glu Ile Met Ala Met
            870                 875                 880

<210> SEQ ID NO 10
<211> LENGTH: 1210
<212> TYPE: PRT
<213> ORGANISM: Meloidogyne javanica

<400> SEQUENCE: 10

Met Val Thr Lys Ile Pro Thr Phe Pro Leu Leu Phe Ile Phe Pro Phe
1               5                   10                  15

Leu Phe Thr Phe Leu Thr Thr Lys Cys Gln Ala Tyr Ser Ile Pro Leu
            20                  25                  30

Ile Ser Glu Cys Asn Ser Glu Glu Ala Pro Val Phe Leu Leu Gln Arg
        35                  40                  45

Asn Val Ser Ser Ile Ala Gly Thr Glu Pro Leu Arg Thr Val Pro Val
    50                  55                  60

Thr Gly Gly Phe Leu Glu Cys Ala Glu Leu Cys Ser Ala Ala Asn Asn
65                  70                  75                  80

Cys Val Ala Val Lys Phe Ser Ile Glu Lys Gln Cys Gln Leu Leu Gly
```

-continued

```
                85                  90                  95
Lys Thr Thr Met Thr Ala Thr Thr Leu Ser Leu Gln Asp Ile Asn Leu
                100                 105                 110

Thr Leu Ala Arg Leu Ala Thr Lys Ser Cys Val Lys Ser Lys Lys Ile
            115                 120                 125

Cys Ser Ser Pro Phe His Phe Asp Val His Glu Gln Lys Ile Leu Val
130                 135                 140

Gly Phe Ala Arg Glu Val Val Ser Ala Glu Ser Ile His Gln Cys Leu
145                 150                 155                 160

Thr Ala Cys Leu Asp Ala Val Asp Thr Phe Gly Phe Glu Cys Glu Ser
                165                 170                 175

Val Met Tyr Tyr Pro Leu Asp Ala Glu Cys Ile Leu Asn Thr Glu Asp
                180                 185                 190

Arg Leu Asp Arg Pro Asp Leu Phe Val Asp Glu Lys Glu Asp Thr Val
            195                 200                 205

Val Tyr Leu Asp Asn Asn Cys Ala Gly Ser Gln Cys His Ala Pro Tyr
210                 215                 220

Val Thr Gln Tyr Val Ala Val Glu Gly Lys Gln Leu Ala Glu Glu Leu
225                 230                 235                 240

Asp His Asn Phe Glu Gly Met Glu Leu Thr Glu Cys Glu Gln Leu Cys
                245                 250                 255

Asn Gln Arg Leu Ser Val Ser Ala Asn Asp Phe Asn Cys Lys Ala Phe
                260                 265                 270

Met Tyr Asn Asn Gln Thr Arg Ser Cys Ile Leu Ser Asp Glu Arg Ser
            275                 280                 285

Arg Pro Leu Gly Arg Ala Asn Leu Thr Asp Ala Lys Gly Trp Thr Tyr
290                 295                 300

His Glu Lys Lys Cys Phe Ala Ser Pro Arg Thr Cys Arg Asn Val Pro
305                 310                 315                 320

Ser Phe Thr Arg Val Pro Gln Met Leu Leu Val Gly Phe Ala Ser Phe
                325                 330                 335

Val Met Glu Asn Val Pro Ser Val Thr Met Cys Leu Asp Gln Cys Thr
                340                 345                 350

Asn Pro Pro Pro Glu Thr Gly Gln Ser Phe Val Cys Lys Ser Val Met
            355                 360                 365

Tyr Tyr Tyr Asn Glu Gln Glu Cys Ile Leu Asn Ala Glu Ser Arg His
370                 375                 380

Ser Lys Pro Asp Leu Phe Ile Pro Glu Glu Asp Asp Phe Val Val Asp
385                 390                 395                 400

Tyr Phe Asp Ile Asn Cys Arg Leu Glu Gln Glu Gln Cys Ile Asp Gly
                405                 410                 415

Arg Thr Pro Gln Leu Val Arg Thr Ile Asn Ser Ala Leu Pro Glu Gly
                420                 425                 430

Glu Gly Ser Ile His Val Leu Glu Thr Ile Lys Gly Val Gln Gln
            435                 440                 445

Cys Ala Lys Lys Cys Ser Glu Arg Ala Pro Asp Lys Cys Arg Ser Phe
450                 455                 460

Asn Phe Asp Lys Gln Ala Gly Asn Cys Asn Leu Leu Tyr Leu Asp Gly
465                 470                 475                 480

Gln Gly Ser Leu Arg Pro Glu Gln Lys Thr Gln Phe Asp Leu Tyr Asp
                485                 490                 495

Val His Cys Leu Ser Gly Thr Ser Gln Leu Leu Gly Glu Asn Ser Lys
                500                 505                 510
```

-continued

His Ser Pro Ser Ala Cys Val Asp Pro Glu Gly Ala Ile Phe Ser Arg
            515                 520                 525

Phe Leu Tyr Thr Arg Trp Val Ala Asn Ser Pro Asn Arg Glu Ile Ser
        530                 535                 540

Ser Leu Pro Leu Ser Lys Cys Leu Asn Leu Cys Ser Val Gly Gly Glu
545                 550                 555                 560

Gln Cys Glu Gly Val Asn Tyr Asn Arg Arg Asn Gly Ser Cys Gln Leu
                565                 570                 575

Phe Thr Ser Leu Leu Leu Asn Ser Ser Pro Asn Ser Gln Gln Asp Lys
            580                 585                 590

Asp Glu His Val Asp Phe Tyr Arg Asn Ile Cys Arg Val Lys Glu Ser
        595                 600                 605

Lys Ser Asp Ser Gly Ala Ala Asn Val Pro Lys Thr Gln Gln Ala Thr
    610                 615                 620

Ala Ala Pro Pro Pro Ser Val Gln Leu Thr Thr Lys Pro Pro Gln Ile
625                 630                 635                 640

Arg Asp Leu Asn Asn Asn Asn Lys Thr Thr His Lys Glu Pro Asn Ile
                645                 650                 655

Lys Leu Pro Pro Gln Ser Ala Lys Pro Ile Asn Gly Lys Thr Gly Lys
            660                 665                 670

Glu Gln Leu Pro Val Gly Ser Lys Ser Phe Gly Val Thr Asn Thr Arg
        675                 680                 685

Asp Asp Gly Glu Asn Ser Ile Thr Gly Thr Ala Pro Pro Val Asp
    690                 695                 700

Gly Lys Leu Ile Ile Lys Pro Ser Pro Gln Val Ser Ile Pro Ser Pro
705                 710                 715                 720

Val Leu Ile Pro Ala Gln Glu Val His Thr Ile Cys Asn Tyr Glu Gly
                725                 730                 735

Ile Ser Val Gln Ile Lys His Ser Ser Pro Phe Ser Gly Val Val Phe
            740                 745                 750

Val Arg Asn Lys Tyr Asp Thr Cys Arg Val Lys Leu Lys Glu Arg Thr
        755                 760                 765

Ala Leu Phe Trp Phe Trp Gly Phe Gln Gln Ile Leu Glu Met Lys Pro
    770                 775                 780

Ile Ala Leu Ile Asn Ser Gln Lys His Gly Lys Gly Asn Lys Thr His
785                 790                 795                 800

Gly Asp Thr Leu Leu Ser Ile Glu Gly Ser Lys Lys Gln Ile Glu Gly
                805                 810                 815

Gly Ser Ser Thr Glu Asp Ile Gln Leu Ile Asn Ser Gln Lys Asp Leu
            820                 825                 830

Lys Arg Ser Arg Arg Gln Leu Gln Arg Asp Cys Gly Leu Gln Asp Met
        835                 840                 845

Asp Asn Gly Thr Tyr Lys Thr Val Ile Val Gln Thr Asn Asn Leu
    850                 855                 860

Gly Ile Pro Gly Leu Val Thr Ser Met Asp Gln Leu Tyr Glu Ile Ser
865                 870                 875                 880

Cys Asn Tyr Ser Ser Met Leu Gly Gly Lys Val Gln Thr Ala Ala Ala
                885                 890                 895

Leu Arg Val His Gly Pro Gln Pro Ser Leu Ile Gln Pro Arg Gly Lys
            900                 905                 910

Ile Glu Leu Gly Asn Pro Val Leu Met Gln Met Gly Pro Val Arg Ser
        915                 920                 925

-continued

Glu Arg Gln Ser Gly Glu Gly Pro Leu Ile Gln Ala Lys Leu Gly Asp
        930                 935                 940

Ile Leu Glu Leu Lys Trp Glu Ile Met Ala Met Asp Glu Glu Leu Asp
945                 950                 955                 960

Phe Leu Val Arg Asp Cys Phe Ala Glu Pro Gly Thr Ser Gly Asn Gln
            965                 970                 975

Gly Glu Arg Leu Pro Leu Ile Glu Asn Gly Cys Pro Thr Pro Ala Val
        980                 985                 990

Ala Gln Lys Leu Ile Pro Asn Pro Ile Lys Ala Ile Asn Ser Ala Val
    995                 1000                1005

Lys Leu Thr Tyr Leu Gln Ala Phe Arg Phe Asp Ser Ser Pro Ala Ile
    1010                1015                1020

Arg Ile Thr Cys His Leu Glu Leu Cys Lys Glu Asn Cys Lys Ser Val
1025                1030                1035                1040

Asn Cys Lys Phe Asn Asp Gly Ile Lys Glu Ser Trp Gly Arg Lys Arg
            1045                1050                1055

Arg Phe Ala Ile Asp Asn Asn Ile Asn Arg Lys Asn Glu Val Lys Glu
            1060                1065                1070

Phe Glu Thr Arg Arg Phe Val Val Pro Arg Phe Ala Gln Ala Thr Thr
            1075                1080                1085

Ser Leu Val Ile Val Asp Pro Leu Gln Gln Asn Ser Val Ile Lys
    1090                1095                1100

Thr Glu Gln Gln Gln Gln Pro Phe Ile Ser His Ser Ser Ile Ser Lys
1105                1110                1115                1120

Gln Ile Phe Glu Asn Asn Lys Lys Glu Asn Asn Lys Asn Ile Thr Lys
            1125                1130                1135

Thr Ala Lys Lys Ser Ser Ser Leu Phe Glu Ala Phe Thr Glu Ala Ala
        1140                1145                1150

Gly Gly Arg Lys Ile Asn Leu Glu Leu Thr Thr Thr Asn Ser Glu Gln
        1155                1160                1165

Gln Gln Leu Cys Leu His Lys Trp Thr Leu Gly Gly Val Phe Gly Thr
    1170                1175                1180

Leu Leu Thr Leu Ile Val Val Gln Ser Gly Val Ala Ala Lys His Leu
1185                1190                1195                1200

Ile Asn Arg Phe Ile Val Gly Lys Arg Ile
            1205                1210

<210> SEQ ID NO 11
<211> LENGTH: 250
<212> TYPE: PRT
<213> ORGANISM: Heterodera glycines

<400> SEQUENCE: 11

Glu Gln Lys Ile Leu Val Gly Phe Ala Arg Glu Val Val Ser Ala Asp
 1               5                  10                  15

Ser Val His Arg Cys Leu Ser Ala Cys Leu Asn Ala Phe Asp Thr Phe
            20                  25                  30

Gly Phe Glu Cys Glu Ser Val Met Tyr Tyr Pro Val Asp Ala Glu Cys
        35                  40                  45

Ile Leu Asn Thr Glu Asp Arg Leu Asp Arg Pro Asp Leu Phe Val Asp
    50                  55                  60

Glu His Glu Asp Thr Val Ile Tyr Leu Asp Asn Asn Cys Ala Gly Cys
65                  70                  75                  80

Glu Cys His Trp His Phe Asp Asn Phe Lys Thr Ser Gly Ile Leu Asn
                85                  90                  95

```
Asp Gln Gln Phe Ala Ile Ala Ala Gln Cys Tyr Ala Pro Tyr Val Thr
                100                 105                 110

Gln Tyr Val Ala Val Glu Gly Arg Gln Leu Ser Asp Glu Leu Asp His
            115                 120                 125

Ser Phe Glu Gly Leu Glu Leu Ser Glu Cys Glu Leu Cys Thr Gln
130                 135                 140

Arg Leu Ser Val Thr Ala Asn Asp Phe Asn Cys Lys Ser Phe Met Tyr
145                 150                 155                 160

Ser Asn Leu Thr Arg Ser Cys Val Leu Ser Asp Glu Arg Ser Arg Pro
                165                 170                 175

Leu Gly Arg Ala Asn Leu Ala Glu Val Pro Gly Trp Thr Tyr Phe Glu
            180                 185                 190

Ser Arg Gly Val Pro Ser Phe Thr Arg Val Pro Gln Met Leu Leu Val
        195                 200                 205

Gly Phe Ala Ser Phe Val Met Glu Asn Val Pro Ser Val Thr Met Cys
    210                 215                 220

Leu Asp Gln Cys Thr Ser Pro Pro Glu Thr Gly Gln Asn Phe Val
225                 230                 235                 240

Cys Lys Ser Val Met Tyr Tyr Asn Glu
                245                 250

<210> SEQ ID NO 12
<211> LENGTH: 881
<212> TYPE: PRT
<213> ORGANISM: Brugia malayi

<400> SEQUENCE: 12

Met His Leu Ser Asn His Ala Ser Ser Leu Leu His Tyr Tyr Ser His
 1               5                  10                  15

Leu Ile Ile Ile Ala Tyr Phe Ser Val Phe Ala Ser Ile Glu Ile Gln
            20                  25                  30

Glu Ile Pro Ser Tyr Pro Ala Cys Ser Asn Gly Glu Ser Pro Val Phe
        35                  40                  45

Leu Leu Gln His Asn Ala Thr Ala Gly Asn Val Leu Lys Arg Ala Ser
    50                  55                  60

Thr Ser His Leu Val Asp Cys Thr Asp Leu Cys Ser Ala Asn Asp Glu
65                  70                  75                  80

Cys Leu Ala Ile Thr Tyr Glu Asp Lys Glu Cys Lys Met Leu Ser Ser
                85                  90                  95

Ile Gly Glu Ser Thr Gly His Leu Asn Asp Tyr Val Leu Leu Ser Lys
            100                 105                 110

Asn Cys Ala Lys Ser Ala Arg Ile Cys Ser Ser Pro Phe Gln Phe Asp
        115                 120                 125

Val His Arg Gln Lys Ile Leu Val Gly Phe Ala Arg Glu Val Val Ser
    130                 135                 140

Ala Asp Ser Leu Ser Leu Cys Leu Ser Ala Cys Leu Asn Ala Phe Asp
145                 150                 155                 160

Ser Phe Gly Phe Glu Cys Glu Ser Val Met Tyr Pro Val Asp Ser
                165                 170                 175

Glu Cys Ile Leu Asn Thr Glu Asp Arg Leu Asp Arg Pro Asp Leu Phe
            180                 185                 190

Gly Asp Glu Leu Asp Asp Asn Val Ile Tyr Leu Asp Asn Asn Cys Ala
        195                 200                 205

Gly Ser Gln Cys Tyr Ala Pro Tyr Ile Thr Gln Tyr Ile Ala Val Ala
```

-continued

```
            210                 215                 220
Asn Arg Gln Leu Ala Asn Glu Leu Asp Arg Gln Leu Ile Ala Asp Arg
225                 230                 235                 240
Glu Ser Cys Glu Ser Leu Cys Thr Gln Arg Leu Ser Thr Thr Thr Asn
                245                 250                 255
Asp Phe Asn Cys Lys Ser Phe Met His Asn Pro Glu Thr Asn Val Cys
                260                 265                 270
Ile Leu Ser Asp Glu Arg Ser Lys Pro Leu Gly Arg Gly Asn Leu Val
                275                 280                 285
Lys Ala Asp Gly Phe Thr Tyr Tyr Glu Lys Lys Cys Phe Ala Ser Pro
290                 295                 300
Arg Thr Cys Arg Asn Val Pro Ser Phe Glu Arg Ile Pro Gln Met Ile
305                 310                 315                 320
Leu Val Gly Phe Ala Ala Phe Val Met Glu Asn Val Pro Ser Val Thr
                325                 330                 335
Met Cys Leu Asp Gln Cys Thr Asn Pro Pro Glu Thr Gly Glu Asn
                340                 345                 350
Phe Glu Cys Lys Ser Val Met Tyr Tyr Tyr Asn Glu Gln Glu Cys Ile
                355                 360                 365
Leu Asn Ala Glu Thr Arg Glu Asn Lys Ser Glu Leu Phe Ile Pro Glu
370                 375                 380
Gly Glu Glu Phe Gln Val Asp Tyr Phe Asp Ile Thr Cys His Leu Arg
385                 390                 395                 400
Pro Glu Thr Cys Pro Asn Gly Thr Thr Leu His Thr Val Arg Thr Val
                405                 410                 415
Asn Ala Ala Leu Pro Glu Gly Glu Gly Ser Ile His Ile Leu Gln Ser
                420                 425                 430
Ala Gly Asn Ser Val Ala Asp Cys Met Thr Lys Cys Tyr Glu Met Ala
                435                 440                 445
Pro Glu Lys Cys Arg Ala Phe Asn Phe Asp Lys Gln Thr Ser Asp Cys
                450                 455                 460
Asp Leu Leu Tyr Val Asp Gly Lys Thr Thr Leu Arg Pro Ala Val His
465                 470                 475                 480
Ser Gly Ile Asp Leu Tyr Asp Leu His Cys Leu Glu Gln Thr Lys Val
                485                 490                 495
Cys Ala Gln Lys Asn Asn Val Thr Arg Phe Ser Arg Tyr Leu Tyr Ser
                500                 505                 510
Ile Tyr Asp Ala Val Pro Ser Gln Phe Tyr Glu Ala Thr Ala Leu Thr
                515                 520                 525
Asn Cys Leu Asn Leu Cys Ala Tyr Thr Glu Arg Cys Glu Gly Val Asn
                530                 535                 540
Tyr Asn Arg Arg Asn Gly Arg Cys Glu Leu Phe Asp Lys Val Glu Gly
545                 550                 555                 560
Asn Gly Lys Pro Ser Asp Phe Thr Asp Phe Tyr Lys Asn Leu Cys Leu
                565                 570                 575
Val Glu Glu Val Glu Ser Glu Tyr Ser Ala Ala Ala Asn Val Pro Lys
                580                 585                 590
His Leu Leu Pro Asn Val Ser His Ser Ala Val Thr Gln Lys Gln Glu
                595                 600                 605
Ala Lys Leu His Ile Ile Ser Ala Lys Thr Lys Pro Phe Leu Arg Glu
                610                 615                 620
Gln Glu Ala Gln Arg Arg Ala Pro Glu Thr Ile Thr Ala Lys Ser Ser
625                 630                 635                 640
```

-continued

```
Ser Ala Ser Gly Lys Val Ser Gly Glu Ala Gly Ser Ser Thr Thr Phe
            645                 650                 655

Ser Ile Ser Ser Ser Gly Arg Leu Pro Gly Pro Val Val Gln Ile Ala
            660                 665                 670

Pro Asn Ala Val Gln Thr Val Cys Asn Tyr Glu Gly Ile Lys Val Gln
            675                 680                 685

Met Glu Asn Pro Lys Ala Phe Ser Gly Val Ile Phe Val Lys Asn Arg
            690                 695                 700

Tyr Glu Thr Cys Arg Val Glu Val Thr Asp Ser Glu Ser Ala Pro Leu
705                 710                 715                 720

Val Ile Gly Leu Pro Pro Asn Phe Gly Ser Lys Met Val Ala Asp Glu
                725                 730                 735

Lys Val Ala Ala Ser Glu Ala Asn Ile Gln Pro Glu Ile Ser Gly Gly
                740                 745                 750

Asp Lys Leu Asp Lys Pro Ala Asp Glu Leu Arg Ile Arg Arg Gln Ala
                755                 760                 765

Leu Glu Leu His Arg Asp Cys Gly Ile Gln Asp Met Asn Asn Gly Thr
            770                 775                 780

Tyr Lys Ser Thr Val Val Gln Thr Asn Asn Leu Gly Ile Pro Gly
785                 790                 795                 800

Leu Val Thr Ser Met Asp Gln Ile Phe Glu Val Ser Cys Asp Tyr Ser
                805                 810                 815

Ser Met Leu Gly Gly Lys Val Thr Ala Gly Ala Asn Leu Thr Ile Asp
                820                 825                 830

Gly Pro Glu Ala Ser Leu Ile Gln Pro Arg Gly Lys Ile Glu Leu Gly
            835                 840                 845

Asn Pro Val Leu Met Gln Met Leu Ser Gly Gln Gly Glu Pro Val Leu
            850                 855                 860

Gln Ala Lys Leu Gly Asp Ile Leu Gln Leu Arg Trp Glu Ile Met Ala
865                 870                 875                 880

Met
```

<210> SEQ ID NO 13
<211> LENGTH: 3633
<212> TYPE: DNA
<213> ORGANISM: Meloidogyne javanica

<400> SEQUENCE: 13

```
atggttacaa aaatcccaac ttttcccctc cttttatttt tcccatttttt atttacattt      60
ttaacgacaa aatgtcaggc ttattctata ccattaatat cagaatgtaa ttcggaagaa     120
gccccagttt ttcttttgca acggaatgtt tcttctatcg ccggaactga gcctttaaga     180
actgttcctg ttacaggggg attttttggaa tgtgcggaac tttgttcagc agcaaataat     240
tgtgttgctg ttaaatttttc tattgaaaaa caatgccaat tgttgggaa acaactatg      300
acagcaacaa ctttatcttt acaagacatt aatttgacac tagctagatt agctactaaa     360
agttgtgtta agagcaaaaa aatctgttct tccccctttcc atttgatgt tcacgaacaa     420
aaaatacttg ttggttttgc tagagaagtt gtatcagcag aatctataca tcaatgttta     480
actgcttgtt tagatgctgt tgatactttt ggctttgaat gcgagtcagt aatgtattat     540
ccattggatg ccgaatgtat tttaaataca gaagacagac ttgaccgtcc agatttgttt     600
gttgatgaga aggaagatac tgttgtttat ttggataata attgtgctgg atcccaatgt     660
catgcccctt atgtaaccca atatgtagct gttgaaggaa aacaattagc tgaggaattg     720
```

```
gatcataatt ttgagggaat ggagttgaca gaatgtgaac agctttgtaa tcaaagattg    780
agtgtttctg caaatgactt taattgcaaa gcatttatgt acaataacca aacaagatct    840
tgtattcttt ctgatgaacg ttcaagacct ttgggtagag ctaatttgac agatgctaaa    900
ggatggactt atcacgagaa aaaatgtttt gcctccccac gtacatgccg aaatgttcct    960
tcttttaccc gcgtccctca aatgttatta gttggatttg cctcttttgt aatggaaaat   1020
gtcccttcag taactatgtg tttggatcaa tgtacaaatc ctcccccaga aactggacaa   1080
agttttgttt gtaaatctgt catgtattat tataatgagc aagaatgtat tttaaatgct   1140
gaatcacgtc attccaagcc agatttattt attcccgaag aagacgattt tgttgtagat   1200
tattttgata taaattgccg tctagaacaa gaacaatgta tcgatggaag aacgccccaa   1260
ttagttagaa caattaattc tgcacttcca gaaggggagg ggtctataca tgttttggaa   1320
acaattaagg gaggagttca gcaatgtgct aaaaaatgtt ctgaacgcgc cccagacaaa   1380
tgtcgctctt tcaattttga taaacaagct ggtaattgta atttactttt tttggatgga   1440
caagggtctt tacgaccaga gcaaaagaca caattcgatt tatacgatgt tcattgtttg   1500
agtggaacat ctcaactttt aggagaaaat tctaaacatt ctccctctgc ttgtgttgac   1560
ccagaagggg ctattttttag tcgtttcctc tacactcgtt gggtagcaaa ttctcccaat   1620
cgtgaaattt caagtttacc actttccaaa tgtttaaatc tttgttcggt tggaggagaa   1680
caatgtgagg gtgttaatta caatcgccga aatggttctt gtcaattatt tacttcccct   1740
ctattaaact cttctccaaa ttctcaacaa gacaaagacg aacatgttga ttttttacaga   1800 aatatttgta gagttaagga atcgaaaagt gatagtgggg ctgctaatgt acccaaaaca   1860
caacaagcaa cggctgcacc tccccctttct gttcaattaa ctactaaacc tccacaaatt   1920
cgtgatttaa acaacaacaa taaaacaaca cacaaagaac caaatattaa acttccacca   1980
caatcagcaa aacctataaa tggaaaaact ggaaaggaac aacttcctgt agggtcaaaa   2040
tcttttgggg ttactaatac gcgtgatgat ggggagaatt caataactgg aactgctcct   2100
cctcctgtag atggcaaatt aattattaaa ccttcaccac aagtttctat tccctcccct   2160
gtacttattc cggcacaaga agtacatact atttgtaatt atgaaggaat tagtgttcaa   2220
attaaacatt cttctccatt ctctggcgtt gttttttgttc gaaataaata tgatacttgc   2280
cgtgtgaagt tgaaggaaag gacagcgttg ttttggtttt ggggcttcca gcaaattttg   2340
gaaatgaagc caattgcttt aattaattca caaaaacatg gaaaagggaa taaaacacac   2400
ggagatactt tactttctat tgaaggttcc aaaaaacaaa ttgaagggg ttcttcaact   2460 gaagatattc aattaataaa ttctcaaaaa gaccttaaac gttcaagaag acaattacaa   2520
agagattgtg gattacaaga tatggacaat ggaacttaca aaactgttat tgttgtccaa   2580
acaaataatt tgggaattcc gggacttgtt acttctatgg accaacttta tgagatttcc   2640
tgtaactatt caagtatgtt gggaggcaaa gtccaaacag cagctgcatt acgtgttcac   2700
ggtccccaac cttcactaat ccagcctcgc ggcaaaatag aattgggaaa tcctgttttg   2760
atgcaaatgg ggcctgtacg tagtgaaagg caaagtgggg aagggccttt aattcaagct   2820 aaattgggggg atattcttga attaaaatgg gaaattatgg caatggatga agaattggac   2880 ttttagttc gtgattgttt tgcagagccg ggaacttctg gaaatcaagg ggaaagactt   2940
cctttaattg agaatggttg tccaacacca gcagtagcac aaaaattaat tccaaatcca   3000
ataaaagcaa ttaattctgc agttaaatta acttatttac aagcattcag atttgacagt   3060
```

-continued

```
tctccagcta ttagaataac ttgtcattta gaattatgta aagaaaattg taaatcggtt   3120
aattgtaaat ttaatgatgg aattaaagaa tcgtggggca gaaaacgccg ttttgctatt   3180
gacaataaca ttaataggaa aaatgaagtt aaagaattcg aaactcgccg ttttgtcgtt   3240
ccccgttttg cccaagcaac aacttcttta gttattgtag accctttaca acaacaaaat   3300
tctgttataa aaacagaaca acaacaacaa ccatttattt cacattcctc aatatctaaa   3360
caaatatttg aaaataataa aaaagaaaat aataaaaata taacaaaaac agctaaaaaa   3420
tcctcttctc tttttgaagc ttttactgag gctgctggtg gaaggaaaat taatttagaa   3480
ttaacaacaa caaattcaga acaacaacaa ctttgtttac ataaatggac acttgggggt   3540
gtttttggaa ctcttttaac attaattgtt gttcaaagcg gggttgctgc taaacattta   3600
attaatcgat ttattgttgg aaaaagaatt taa                                3633
```

<210> SEQ ID NO 14
<211> LENGTH: 750
<212> TYPE: DNA
<213> ORGANISM: Heterodera glycines

<400> SEQUENCE: 14

```
gagcagaaga ttttggtggg tttcgcgcgg gaggtggtct ccgccgactc agtccaccgc     60
tgtctgtccg cttgtctgaa tgcgttcgat acgttcggct tcgaatgcga gtcggtcatg    120
tattaccctg tggacgcgga atgcattttg aacacggagg accgattgga tcggcctgac    180
cttttcgtgg acgagcacga ggacacggtc atctacttgg acaacaattg cgccggatgt    240
gagtgccatt ggcattttga caatttcaaa acaagcggca ttttgaacga ccaacaattc    300
gcaattgcag cacaatgtta cgcaccgtac gtaacgcaat acgtggcggt ggaaggacgc    360
caattgtcgg acgaattgga ccacagtttt gaagggttgg agctgagcga atgtgaagag    420
ttgtgcacgc aacggttaag tgttacggca aacgacttca actgcaaatc gttcatgtac    480
agtaacttga cgcgcagttg cgttttgtcg gacgaacgct cgcgcccttt gggccgtgcc    540
aatttggccg aagtgccggg atggacttat ttcgagagcc gcggcgttcc gtcgtttacg    600
cgagtgccgc aaatgctttt ggtgggcttt gcctcttttg tgatggaaaa tgtgccgtca    660
gtgacaatgt gtttggacca atgcacaagc cctcctcctg agacgggaca aaactttgtg    720
tgtaaatcgg tgatgtacta ctacaacgag                                     750
```

<210> SEQ ID NO 15
<211> LENGTH: 2643
<212> TYPE: DNA
<213> ORGANISM: Brugia malayi

<400> SEQUENCE: 15

```
atgcatcttt ccaaccatgc ctcatcactt ctgcattact attcacatct catcataatt     60
gcatactttt ctgtatttgc ttcaatcgaa atacaagaaa ttccatcata tccagcatgt    120
agcaatggcg aatcacctgt ctttttactc caacacaatg ctacagcagg taatgttctg    180
aagcgagctt caacttcaca tctggtcgac tgcactgacc tttgttcagc taacgatgaa    240
tgtttggcga taacctatga agataaagaa tgcaaaatgt tgtcaagcat tggagaatcg    300
acaggacatt taaatgatta tgtattgctg agtaaaaatt gtgctaaaag tgcgcggatc    360
tgctcatcgc catttcaatt cgatgtacac agacaaaaaa ttttggttgg gtttgctcgc    420
gaggttgtgt cagctgattc attatcgtta tgtctatcag cttgcttgaa tgcatttgat    480
tctttcggtt ttgaatgtga gtcggtaatg tactatccag ttgattcaga atgcatccta    540
```

```
aacaccgaag atcgtctgga tcgacctgac ttgtttgggg atgaattaga tgataacgtc    600
atttatttgg ataacaactg tgctggatca cagtgttatg ctccatacat aacacaatac    660
attgccgtcg caaatcgtca gctagctaac gagttggaca dacaactgat cgctgatcgt    720
gaatcatgcg agtcgttatg tactcagcga ctgtctacaa cgacaaacga tttcaactgt    780
aaatcattta tgcataatcc ggaaactaac gtttgcatac tttctgatga acgttctaaa    840
ccacttggtc gaggcaatct agtgaaagct gacggtttca catattatga aagaaatgt     900 tttgcatcac cacgaacatg tcgcaatgta ccgtcgtttg agcgcatacc tcagatgata    960
cttgttggtt ttgctgcatt tgttatggaa aatgtacctt cagtaacgat gtgcctcgat   1020
cagtgcacaa atcctccacc ggaaactgga gaaaatttcg aatgcaaatc tgtgatgtat   1080
tattataacg aacaggaatg tattttaaac gctgaaacac gagaaaataa atcggaattg   1140
tttataccgg agggagaaga attccaagtc gattattttg atatcacttg tcatctgcgc   1200
cctgaaacat gtccaaatgg cacaacatta catactgtac gtacggttaa tgcagcactc   1260
cctgaaggcg aaggatcgat ccatattttg cagtcagccg ggaattcggt tgctgattgc   1320
atgacaaaat gttacgagat ggctcccgag aaatgtcgcg cattcaattt tgataagcag   1380
acatctgact gtgacctgct gtacgttgat gggaagacaa ccttacgacc agcagtccac   1440
tcgggcattg atctctacga ccttcattgc ctagagcaga caaaagtttg cgctcagaaa   1500
aacaacgtaa cacgattttc gagatatttg tacagtatat atgatgcagt gccatcgcaa   1560
ttctacgaag caactgccct cacaaattgt cttaatcttt gcgcatatac cgagcgttgc   1620
gaaggtgtaa attacaacag aaggaatggt cgttgtgaat tatttgataa ggtcgaagga   1680 aatgaaagc caagtgattt cacggatttt tacaaaaatc tttgtctggt ggaagaagta    1740
gaatcagaat atagcgccgc agctaatgtt cccaaacatc tccttccgaa tgtttcacat   1800
tctgcagtta ctcagaaaca agaagctaaa ttacacatta tctcagcaaa aacaaagcct   1860
ttcctacgcg aacaggaagc acagcgacga gctccagaaa caataacagc gaagtcgtct   1920
tcagcttccg gaaaagtaag tggtgaagca ggatcatcaa ctacattcag catttcttca   1980
tccggaaggc ttccagggcc agtagtccaa attgctccaa atgcagtgca aacagtttgc   2040
aattatgaag gcatcaaagt gcagatggag accccaaag cctttcggg agtgatattt      2100 gttaaaaata ggtatgaaac ctgtcgagta gaggttacgg atagtgaaag tgcaccacta   2160
gtaattggtt taccaccgaa ttttggttca aaaatggtag ctgatgaaaa ggttgccgca   2220
agcgaagcaa atattcaacc agaaatatcc ggaggcgaca aactggataa acccgctgat   2280
gaactgcgca taagacgaca agctttagag ctacacagag attgcggaat ccaggatatg   2340
aacaatggta cttataaatc aacggtggtt gtacaaacaa ataacttggg tatacctgga   2400
ctggtaactt ccatggatca gattttgaa gtgagctgtg attatagttc aatgcttggt     2460
ggaaaagtta ctgctggtgc caatctcaca attgatggtc ccgaagcatc tcttattcaa   2520
ccccgaggaa aaatcgaact tggtaacccg gtgcttatgc agatgttgag tggacaagga   2580
gaacctgtcc tacaagcaaa actaggtgac attctgcagc tacgatggga aatcatggcg   2640
atg                                                                  2643
```

<210> SEQ ID NO 16
<211> LENGTH: 1065
<212> TYPE: PRT
<213> ORGANISM: Caenorhabditis elegans -continued

```
<400> SEQUENCE: 16

Met Lys Val Phe Ala Val Leu Ala Leu Val Val Ala Ser Val Leu Ala
1               5                   10                  15

Asp Thr Leu Pro Ser Val Thr Leu Cys Pro Pro Glu Thr Gln Thr Ile
                20                  25                  30

Phe Val Leu Gln His Asn Thr Thr Val Gly Ala Arg Ile Arg Thr Ile
                35                  40                  45

Pro Thr Ser Asn Leu Ala Glu Cys Ser Asp His Cys Ser Ala Ser Leu
        50                  55                  60

Asp Cys Gln Gly Val Glu Phe Lys Asp Gly Ser Cys Ala Val Phe Arg
65                  70                  75                  80

Ala Gly Ser Glu Lys Ala Thr Ala Gly Ser Gln Leu Leu Thr Lys Thr
                85                  90                  95

Cys Val Lys Ser Asp Arg Val Cys Gln Ser Pro Phe Gln Phe Asp Leu
                100                 105                 110

Phe Glu Gln Arg Ile Leu Val Gly Phe Ala Arg Glu Val Val Pro Ala
                115                 120                 125

Ala Asn Ile Gln Ile Cys Met Ala Ala Cys Leu Asn Ala Phe Asp Thr
                130                 135                 140

Phe Gly Phe Glu Cys Glu Ser Ala Met Phe Tyr Pro Val Asp Gln Glu
145                 150                 155                 160

Cys Ile Leu Asn Thr Glu Asp Arg Leu Asp Arg Pro Ser Leu Phe Val
                165                 170                 175

Glu Glu Ser Asp Asp Thr Val Ile Tyr Met Asp Asn Asn Cys Ala Gly
                180                 185                 190

Phe Pro Leu Val Phe Lys Asn Tyr Asn Tyr Gln Lys Thr Thr Phe Ser
                195                 200                 205

Lys Ser Gln Cys Tyr Pro Pro Tyr Ile Thr Gln Tyr Ile Ala Val Glu
                210                 215                 220

Gly Lys Gln Leu Lys Asn Glu Leu Asp Arg Ile Ile Asn Val Asp Leu
225                 230                 235                 240

Asp Ser Cys Gln Ala Leu Cys Thr Gln Arg Leu Ser Ile Ser Ser Asn
                245                 250                 255

Asp Phe Asn Cys Lys Ser Phe Met Tyr Asn Asn Lys Thr Arg Thr Cys
                260                 265                 270

Ile Leu Ala Asp Glu Arg Ser Lys Pro Leu Gly Arg Ala Asp Leu Ile
                275                 280                 285

Ala Thr Glu Gly Phe Thr Tyr Phe Glu Lys Lys Cys Phe Ala Ser Pro
                290                 295                 300

Asn Thr Cys Arg Asn Val Pro Ser Phe Lys Arg Val Pro Gln Met Ile
305                 310                 315                 320

Leu Val Gly Phe Ala Ala Phe Val Met Glu Asn Val Pro Ser Val Thr
                325                 330                 335

Met Cys Leu Asp Gln Cys Thr Asn Pro Pro Glu Thr Gly Asp Gly
                340                 345                 350

Phe Val Cys Lys Ser Val Met Tyr Tyr Tyr Asn Glu Gln Glu Cys Ile
                355                 360                 365

Leu Asn Ser Glu Thr Arg Glu Ser Lys Pro Glu Leu Phe Ile Pro Glu
                370                 375                 380

Gly Glu Glu Phe Leu Val Asp Tyr Phe Asp Ile Thr Cys His Leu Lys
385                 390                 395                 400

Gln Glu Lys Cys Pro Thr Gly Gln His Leu Lys Ala Ile Arg Thr Ile
                405                 410                 415
```

```
Asn Ala Ala Leu Pro Glu Gly Glu Ser Glu Leu His Val Leu Lys Ala
            420                 425                 430

Ser Ala Ala Lys Gly Ile Lys Glu Cys Val Ala Lys Cys Phe Gly Leu
            435                 440                 445

Ala Pro Glu Lys Cys Arg Ser Phe Asn Tyr Asp Lys Lys Thr Lys Ser
            450                 455                 460

Cys Asp Leu Leu Tyr Leu Asp Gly His Asn Thr Leu Gln Pro Gln Val
465                 470                 475                 480

Arg Gln Gly Val Asp Leu Tyr Asp Leu His Cys Leu Ala Val Glu Asn
                485                 490                 495

Asp Cys Ser Ala Asn Lys Asp Ala Leu Phe Ser Arg Tyr Leu His
            500                 505                 510

Thr Lys Gln Arg Gly Ile Pro Ala Lys Val Tyr Lys Val Val Ser Leu
            515                 520                 525

Asn Ser Cys Leu Glu Val Cys Ala Gly Asn Pro Thr Cys Ala Gly Ala
            530                 535                 540

Asn Tyr Asn Arg Arg Leu Gly Asp Cys Thr Leu Phe Asp Ala Ile Asp
545                 550                 555                 560

Asp Asp Ala Glu Ile Asn Glu His Thr Asp Phe Tyr Lys Asn Leu Cys
                565                 570                 575

Val Thr Lys Glu Ile Asp Thr Gly Ala Ser Ala Ala Asn Val Pro
            580                 585                 590

Glu Thr Lys His Arg Val Ser Gly Thr Val Val Glu Gly Lys Asp Ser
            595                 600                 605

Lys Ser Gln Leu Leu Ala Thr Lys Val Lys Lys Pro Thr Ile Lys
            610                 615                 620

Asn Thr Glu His Arg Arg Ala Pro Glu Ser Thr Val Pro Ile Gly Pro
625                 630                 635                 640

Pro Val Glu Val Lys Ala Glu Ala Ile Gln Thr Ile Cys Asn Tyr Glu
                645                 650                 655

Gly Ile Lys Val Gln Ile Asn Asn Gly Glu Pro Phe Ser Gly Val Ile
            660                 665                 670

Phe Val Lys Asn Lys Phe Asp Thr Cys Arg Val Glu Val Ala Asn Ser
            675                 680                 685

Asn Ala Ala Thr Leu Val Leu Gly Leu Pro Lys Asp Phe Gly Met Arg
            690                 695                 700

Pro Ile Ser Leu Asp Asn Ile Asp Asp Asn Glu Thr Gly Lys Asn Lys
705                 710                 715                 720

Thr Lys Lys Gly Glu Glu Thr Pro Leu Lys Asp Glu Ile Glu Glu Phe
                725                 730                 735

Arg Gln Lys Arg Gln Ala Ala Glu Phe Arg Asp Cys Gly Leu Val Asp
            740                 745                 750

Leu Leu Asn Gly Thr Tyr Lys Ser Thr Val Val Ile Gln Thr Asn Asn
            755                 760                 765

Leu Gly Ile Pro Gly Leu Val Thr Ser Met Asp Gln Leu Tyr Glu Val
            770                 775                 780

Ser Cys Asp Tyr Ser Ser Met Leu Gly Gly Arg Val Gln Ala Gly Tyr
785                 790                 795                 800

Asn Met Thr Val Thr Gly Pro Glu Ala Asn Leu Ile Gln Pro Arg Gly
                805                 810                 815

Lys Ile Glu Leu Gly Asn Pro Val Leu Met Gln Leu Leu Asn Gly Asp
            820                 825                 830
```

```
Gly Thr Glu Gln Pro Leu Val Gln Ala Lys Leu Gly Asp Ile Leu Glu
        835                 840                 845

Leu Arg Trp Glu Ile Met Ala Met Asp Asp Glu Leu Asp Phe Phe Val
    850                 855                 860

Lys Asn Cys His Ala Glu Pro Gly Val Ala Gly Gly Lys Ala Gly Ala
865                 870                 875                 880

Gly Glu Lys Leu Arg Leu Ile Asp Gly Gly Cys Pro Thr Pro Ala Val
            885                 890                 895

Ala Gln Lys Leu Ile Pro Gly Ala Ile Glu Ile Lys Ser Ser Ala Val
            900                 905                 910

Lys Thr Thr Lys Met Gln Ala Phe Arg Phe Asp Ser Ser Ala Ser Ile
            915                 920                 925

Arg Val Thr Cys Glu Val Glu Ile Cys Lys Gly Asp Cys Glu Pro Val
            930                 935                 940

Glu Cys Ala Leu Thr Gly Gly Val Lys Lys Ser Phe Gly Arg Lys Lys
945                 950                 955                 960

Arg Glu Val Ser Asn Asn Ile Glu Glu Phe Glu Thr Asn Arg Tyr Leu
                965                 970                 975

Ile Pro Arg Arg Ser His Ala Thr Thr Ser Ile Val Ile Asp Pro
            980                 985                 990

Leu Gln Gln Val Asn Glu Pro Val Ala Met Ser Arg Ala Ser Thr Leu
            995                 1000                1005

Asp Leu Leu Arg Glu Asp Ala His Glu Val Gln Met Ile Glu Glu Gly
            1010                1015                1020

Ser Ile Cys Leu Asn Ser Val Thr Val Phe Ala Ile Phe Gly Thr Leu
1025                1030                1035                1040

Ala Val Leu Ile Leu Gly Gln Thr Val Val Ile Ala His Tyr Ala Val
                1045                1050                1055

Arg Arg Phe Ser Ser Glu Lys Thr Ala
            1060                1065

<210> SEQ ID NO 17
<211> LENGTH: 1069
<212> TYPE: PRT
<213> ORGANISM: Caenorhabditis elegans

<400> SEQUENCE: 17

Met Lys Val Phe Ala Val Leu Ala Leu Val Val Ala Ser Val Leu Ala
1               5                   10                  15

Asp Thr Leu Pro Ser Val Thr Leu Cys Pro Pro Glu Thr Gln Thr Ile
            20                  25                  30

Phe Val Leu Gln His Asn Thr Thr Val Gly Ala Arg Ile Arg Thr Ile
        35                  40                  45

Pro Thr Ser Asn Leu Ala Glu Cys Ser Asp His Cys Ser Ala Ser Leu
    50                  55                  60

Asp Cys Gln Gly Val Glu Phe Lys Asp Gly Ser Cys Ala Val Phe Arg
65                  70                  75                  80

Ala Gly Ser Glu Lys Ala Thr Ala Gly Ser Gln Leu Leu Thr Lys Thr
                85                  90                  95

Cys Val Lys Ser Asp Arg Val Cys Gln Ser Pro Phe Gln Phe Asp Leu
            100                 105                 110

Phe Glu Gln Arg Ile Leu Val Gly Phe Ala Arg Glu Val Val Pro Ala
        115                 120                 125

Ala Asn Ile Gln Ile Cys Met Ala Ala Cys Leu Asn Ala Phe Asp Thr
    130                 135                 140
```

```
Phe Gly Phe Glu Cys Glu Ser Ala Met Phe Tyr Pro Val Asp Gln Glu
145                 150                 155                 160

Cys Ile Leu Asn Thr Glu Asp Arg Leu Asp Arg Pro Ser Leu Phe Val
                165                 170                 175

Glu Glu Ser Asp Asp Thr Val Ile Tyr Met Asp Asn Asn Cys Ala Gly
            180                 185                 190

Phe Pro Leu Val Phe Lys Asn Tyr Asn Tyr Gln Lys Thr Thr Phe Ser
            195                 200                 205

Lys Ser Gln Cys Tyr Pro Pro Tyr Ile Thr Gln Tyr Ile Ala Val Glu
210                 215                 220

Gly Lys Gln Leu Lys Asn Glu Leu Asp Arg Ile Ile Asn Val Asp Leu
225                 230                 235                 240

Asp Ser Cys Gln Ala Leu Cys Thr Gln Arg Leu Ser Ile Ser Ser Asn
                245                 250                 255

Asp Phe Asn Cys Lys Ser Phe Met Tyr Asn Asn Lys Thr Arg Thr Cys
                260                 265                 270

Ile Leu Ala Asp Glu Arg Ser Lys Pro Leu Gly Arg Ala Asp Leu Ile
                275                 280                 285

Ala Thr Glu Gly Phe Thr Tyr Phe Glu Lys Lys Cys Phe Ala Ser Pro
                290                 295                 300

Asn Thr Cys Arg Asn Val Pro Ser Phe Lys Arg Val Pro Gln Met Ile
305                 310                 315                 320

Leu Val Gly Phe Ala Ala Phe Val Met Glu Asn Val Pro Ser Val Thr
                325                 330                 335

Met Cys Leu Asp Gln Cys Thr Asn Pro Pro Glu Thr Gly Asp Gly
                340                 345                 350

Phe Val Cys Lys Ser Val Met Tyr Tyr Tyr Asn Glu Gln Glu Cys Ile
                355                 360                 365

Leu Asn Ser Glu Thr Arg Glu Ser Lys Pro Glu Leu Phe Ile Pro Glu
                370                 375                 380

Gly Glu Glu Phe Leu Val Asp Tyr Phe Asp Ile Thr Cys His Leu Lys
385                 390                 395                 400

Gln Glu Lys Cys Pro Thr Gly Gln His Leu Lys Ala Ile Arg Thr Ile
                405                 410                 415

Asn Ala Ala Leu Pro Glu Gly Glu Ser Glu Leu His Val Leu Lys Ala
                420                 425                 430

Ser Ala Ala Lys Gly Ile Lys Glu Cys Val Ala Lys Cys Phe Gly Leu
                435                 440                 445

Ala Pro Glu Lys Cys Arg Ser Phe Asn Tyr Asp Lys Lys Thr Lys Ser
                450                 455                 460

Cys Asp Leu Leu Tyr Leu Asp Gly His Asn Thr Leu Gln Pro Gln Val
465                 470                 475                 480

Arg Gln Gly Val Asp Leu Tyr Asp Leu His Cys Leu Ala Ala Met Pro
                485                 490                 495

Leu Val Glu Asn Asp Cys Ser Ala Asn Lys Asp Ala Leu Phe Ser
                500                 505                 510

Arg Tyr Leu His Thr Lys Gln Arg Gly Ile Pro Ala Lys Val Tyr Lys
            515                 520                 525

Val Val Ser Leu Asn Ser Cys Leu Glu Val Cys Ala Gly Asn Pro Thr
                530                 535                 540

Cys Ala Gly Ala Asn Tyr Asn Arg Arg Leu Gly Asp Cys Thr Leu Phe
545                 550                 555                 560
```

-continued

```
Asp Ala Ile Asp Asp Ala Glu Ile Asn Glu His Thr Asp Phe Tyr
            565                 570                 575

Lys Asn Leu Cys Val Thr Lys Glu Ile Asp Thr Gly Ala Ser Ala Ala
        580                 585                 590

Ala Asn Val Pro Glu Thr Lys His Arg Val Ser Gly Thr Val Val Glu
    595                 600                 605

Gly Lys Asp Ser Lys Ser Gln Leu Leu Ala Thr Lys Val Lys Lys
610                 615                 620

Pro Thr Ile Lys Asn Thr Glu His Arg Arg Ala Pro Glu Ser Thr Val
625                 630                 635                 640

Pro Ile Gly Pro Pro Val Glu Val Lys Ala Glu Ala Ile Gln Thr Ile
                645                 650                 655

Cys Asn Tyr Glu Gly Ile Lys Val Gln Ile Asn Asn Gly Glu Pro Phe
            660                 665                 670

Ser Gly Val Ile Phe Val Lys Asn Lys Phe Asp Thr Cys Arg Val Glu
        675                 680                 685

Val Ala Asn Ser Asn Ala Ala Thr Leu Val Leu Gly Leu Pro Lys Asp
    690                 695                 700

Phe Gly Met Arg Pro Ile Ser Leu Asp Asn Ile Asp Asp Asn Glu Thr
705                 710                 715                 720

Gly Lys Asn Lys Thr Lys Lys Gly Glu Thr Pro Leu Lys Asp Glu
                725                 730                 735

Ile Glu Glu Phe Arg Gln Lys Arg Gln Ala Ala Glu Phe Arg Asp Cys
            740                 745                 750

Gly Leu Val Asp Leu Leu Asn Gly Thr Tyr Lys Ser Thr Val Val Ile
        755                 760                 765

Gln Thr Asn Asn Leu Gly Ile Pro Gly Leu Val Thr Ser Met Asp Gln
    770                 775                 780

Leu Tyr Glu Val Ser Cys Asp Tyr Ser Ser Met Leu Gly Gly Arg Val
785                 790                 795                 800

Gln Ala Gly Tyr Asn Met Thr Val Thr Gly Pro Glu Ala Asn Leu Ile
                805                 810                 815

Gln Pro Arg Gly Lys Ile Glu Leu Gly Asn Pro Val Leu Met Gln Leu
            820                 825                 830

Leu Asn Gly Asp Gly Thr Glu Gln Pro Leu Val Gln Ala Lys Leu Gly
        835                 840                 845

Asp Ile Leu Glu Leu Arg Trp Glu Ile Met Ala Met Asp Asp Glu Leu
    850                 855                 860

Asp Phe Phe Val Lys Asn Cys His Ala Glu Pro Gly Val Ala Gly Gly
865                 870                 875                 880

Lys Ala Gly Ala Gly Glu Lys Leu Arg Leu Ile Asp Gly Gly Cys Pro
                885                 890                 895

Thr Pro Ala Val Ala Gln Lys Leu Ile Pro Gly Ala Ile Glu Ile Lys
            900                 905                 910

Ser Ser Ala Val Lys Thr Thr Lys Met Gln Ala Phe Arg Phe Asp Ser
        915                 920                 925

Ser Ala Ser Ile Arg Val Thr Cys Glu Val Glu Ile Cys Lys Gly Asp
    930                 935                 940

Cys Glu Pro Val Glu Cys Ala Leu Thr Gly Gly Val Lys Lys Ser Phe
945                 950                 955                 960

Gly Arg Lys Lys Arg Glu Val Ser Asn Asn Ile Glu Glu Phe Glu Thr
                965                 970                 975

Asn Arg Tyr Leu Ile Pro Arg Arg Ser His Ala Thr Thr Ser Ile Val
```

-continued

```
                980                 985                 990
Ile Ile Asp Pro Leu Gln Gln Val Asn Glu Pro Val Ala Met Ser Arg
            995                1000                1005

Ala Ser Thr Leu Asp Leu Leu Arg Glu Asp Ala His Glu Val Gln Met
        1010                1015                1020

Ile Glu Glu Gly Ser Ile Cys Leu Asn Ser Val Thr Val Phe Ala Ile
1025                1030                1035                1040

Phe Gly Thr Leu Ala Val Leu Ile Leu Gly Gln Thr Val Val Ile Ala
                1045                1050                1055

His Tyr Ala Val Arg Arg Phe Ser Ser Glu Lys Thr Ala
            1060                1065

<210> SEQ ID NO 18
<211> LENGTH: 741
<212> TYPE: PRT
<213> ORGANISM: Caenorhabditis elegans

<400> SEQUENCE: 18

Met Trp Gly Val Ile Phe Leu Leu Ser Ile Val Pro Ala Ala Gln
1               5                   10                  15

Ser Val Phe Glu Cys Ser Ser His Glu Thr Thr Ala Phe Val Arg Ile
            20                  25                  30

Pro Arg Ala Arg Leu Asp Gly Thr Pro Val Val Ile Ser Thr Ala Gly
        35                  40                  45

His Asp Leu Thr Cys Ala Gln Tyr Cys Arg Asn Asn Ile Glu Pro Thr
    50                  55                  60

Thr Gly Ala Gln Arg Val Cys Ala Ser Phe Asn Phe Asp Gly Arg Glu
65                  70                  75                  80

Thr Cys Tyr Phe Phe Asp Asp Ala Ala Thr Pro Ala Gly Thr Ser Gln
                85                  90                  95

Leu Thr Ala Asn Pro Ser Ala Asn Asn Phe Tyr Tyr Glu Lys Thr Cys
            100                 105                 110

Ile Pro Asn Val Ser Ala His Glu Ala Cys Thr Tyr Arg Ser Phe Ser
        115                 120                 125

Phe Glu Arg Ala Arg Asn Thr Gln Leu Glu Gly Phe Val Lys Lys Ser
    130                 135                 140

Val Thr Val Glu Asn Arg Glu His Cys Leu Ser Ala Cys Leu Lys Glu
145                 150                 155                 160

Lys Glu Phe Val Cys Lys Ser Val Asn Phe His Tyr Asp Thr Ser Leu
                165                 170                 175

Cys Glu Leu Ser Val Glu Asp Lys Arg Ser Lys Pro Thr His Val Arg
            180                 185                 190

Met Ser Glu Lys Ile Asp Tyr Tyr Asp Asn Asn Cys Leu Ser Arg Gln
        195                 200                 205

Asn Arg Cys Gly Pro Ser Gly Gly Asn Leu Val Phe Lys Thr Thr
    210                 215                 220

Asn Phe Glu Ile Arg Tyr Tyr Asp His Thr Gln Ser Val Glu Ala Gln
225                 230                 235                 240

Glu Ser Tyr Cys Leu Gln Lys Cys Leu Asp Ser Leu Asn Thr Phe Cys
                245                 250                 255

Arg Ser Val Glu Phe Asn Pro Lys Glu Lys Asn Cys Ile Val Ser Asp
            260                 265                 270

Glu Asp Thr Phe Ser Arg Ala Asp Gln Gln Gly Gln Val Val Gly Lys
        275                 280                 285
```

-continued

```
Asp Tyr Tyr Glu Pro Ile Cys Val Ala Ala Asp Leu Ser Ser Thr
    290                 295                 300
Cys Arg Gln Gln Ala Ala Phe Glu Arg Phe Ile Gly Ser Ser Ile Glu
305                 310                 315                 320
Gly Glu Val Val Ala Ser Ala Gln Gly Val Thr Ile Ser Asp Cys Ile
                325                 330                 335
Ser Leu Cys Phe Gln Asn Leu Asn Cys Lys Ser Ile Asn Tyr Asp Arg
                340                 345                 350
Thr Ala Ser Ser Cys Phe Ile Tyr Ala Val Gly Arg Gln Asp Ala Asn
                355                 360                 365
Ile Lys Ala Asn Pro Ser Met Asp Tyr Tyr Glu Phe Asn Cys Glu Ser
370                 375                 380
Gln Phe Gly Gly Met Ala Leu Cys Thr Asn Glu Gly Ile Arg Phe Ile
385                 390                 395                 400
Val Asn Thr Lys Glu Pro Tyr Thr Gly Ala Ile Tyr Ala Ala Glu Arg
                405                 410                 415
Phe Ser Thr Cys Ser Gln Val Val Glu Asn Ala Lys Gln Ile Ser Ile
                420                 425                 430
Thr Phe Pro Pro Thr Val Ser Ser Asp Cys Gly Thr Val Ile Arg
                435                 440                 445
Asp Gly Lys Met Glu Ala Leu Val Val Ser Leu Asp Gly Val Leu
450                 455                 460
Pro His Gln Val Thr Thr Glu Trp Asp Arg Phe Tyr Arg Val Ser Cys
465                 470                 475                 480
Asp Val Ser Met Asp Lys Met Val Lys Glu Gly Ser Val Val Thr
                485                 490                 495
Thr Ile Tyr Glu Ala Ser Ser Gln Asn Thr Thr Val Leu Asp Val Ala
                500                 505                 510
Thr Pro Pro Val Ser Ala Glu Leu Gln Ile Leu Asn Gln Leu Glu
                515                 520                 525
Glu Pro Leu His Lys Ala Ser Ile Gly Asp Pro Leu Leu Val Ile
530                 535                 540
Thr Ser Glu Gln Ala Gly Pro His Asn Met Met Val Thr Glu Cys Thr
545                 550                 555                 560
Ala Thr Arg Val Gly Gly Phe Gly Asp Thr Val Pro Phe Thr Leu Ile
                565                 570                 575
Glu Asn Gly Cys Pro Arg Tyr Pro Ala Leu Val Gly Pro Val Glu Gln
                580                 585                 590
Asp Phe Asp Lys Asn Arg Leu Lys Ser Asp Leu Arg Ala Phe Arg Leu
                595                 600                 605
Asp Gly Ser Tyr Asp Val Gln Ile Val Cys Ser Ile Met Phe Cys Ala
610                 615                 620
Gly Pro Asn Gly Cys Pro Val Ser Asn Cys Leu Asp Ser Gly Thr Asn
625                 630                 635                 640
Glu Leu Phe Met Ser His Gly Arg Lys Lys Arg Ser Ala Asp Leu Glu
                645                 650                 655
Ala Gly Glu Thr Glu Glu Lys Leu Ser Ala Ile Ile Arg Val Phe Ala
                660                 665                 670
Lys Gly Glu Asp Glu Glu Met Glu Met Ala Asn Asn Thr Met Met
                675                 680                 685
Thr Ser Met Ser Asp Ser Thr Glu Leu Leu Cys Ile Ala Glu Pro Phe
                690                 695                 700
Phe Val Ser Ser Val Val Ser Leu Ser Val Leu Cys Phe Ala Leu Ser
```

```
                705                 710                 715                 720
Ala Ile Ile Ala Ile Trp Gly Cys His Ser Leu His Ser Lys Pro Val
                    725                 730                 735
Lys Gln Val Ala Ala
        740
```

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ggccacgcgt cgactagtac                                         20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gggtttaatt acccaagttt ga                                      22

<210> SEQ ID NO 21
<211> LENGTH: 37
<212> TYPE: DNA
<213> ORGANISM: Artificial Sequence
<220> FEATURE:
<223> OTHER INFORMATION: Primer

<400> SEQUENCE: 21
ggccacgcgt cgactagtac tttttttttt ttttttt                      37

<210> SEQ ID NO 22
<211> LENGTH: 44
<212> TYPE: RNA
<213> ORGANISM: Artificial Sequence
<220> FEATURE:
<223> OTHER INFORMATION: Primer

<400> SEQUENCE: 22
cgacuggagc acgaggacac ugacauggac ugaaggagua gaaa              44

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ccgtccaaga ggctttgaac                                         20

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
gatctggtcg atcaagtc                                           18

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
cgactggagc acgaggacac tga                                              23

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
ggacactgac atggactgaa ggagta                                           26

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tcagtgacgt tatgtcctcc                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tgacagatgg aacattctcc                                                  20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
acttcaggac acgacttgac                                                  20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
caatcagaga tggtaactcc                                                  20

<210> SEQ ID NO 31
<211> LENGTH: 26
<212> TYPE: DNA
<213> ORGANISM: Artificial Sequence
<220> FEATURE:

```
<223> OTHER INFORMATION: Primer

<400> SEQUENCE: 31
cgttgtagac agtcgctgag tacata                                         26

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
ccaactcgtt agctagctga cg                                             22

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
cgaacatgtc gcaatgtac                                                 19

<210> SEQ ID NO 34
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 4
<223> OTHER INFORMATION: n = a, t, c, or g

<400> SEQUENCE: 34
catngccatd atytccca                                                  18

<210> SEQ ID NO 35
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 6
<223> OTHER INFORMATION: n = a, t, c, or g

<400> SEQUENCE: 35
ttyggnttyg artgygar                                                  18

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
gatcgaggca catcgttac                                                 19

<210> SEQ ID NO 37
<211> LENGTH: 19
<212> TYPE: DNA
<213> ORGANISM: Artificial Sequence
```

-continued

```
<220> FEATURE:
<223> OTHER INFORMATION: Primer

<400> SEQUENCE: 37
gtttagatgc tgttgatac                                                    19

<210> SEQ ID NO 38
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 9, 15
<223> OTHER INFORMATION: n = a, t, c, or g

<400> SEQUENCE: 38
tcdatyttnc cyctnggytg                                                   20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
caagatatgg acaatggaac                                                   20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
atacattcgg catccaatgg                                                   20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
actgactcgc attcaaagcc                                                   20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tagctaatct agctagtgtc                                                   20

<210> SEQ ID NO 43
<211> LENGTH: 17
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: 15
<223> OTHER INFORMATION: n = a, t, c, or g

<400> SEQUENCE: 43
garcaraara tgctngt                                                      17

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tgytcrttrt artartacat                                                   20

<210> SEQ ID NO 45
<211> LENGTH: 1068
<212> TYPE: PRT
<213> ORGANISM: Caenorhabditis briggsae

<400> SEQUENCE: 45
```

Met Lys Val Phe Ala Val Val Ala Leu Leu Ala Val Ser Ala Leu Ala
 1               5                  10                  15

Asp Thr Leu Pro Ser Val Thr Ile Cys Pro Glu Thr Gln Thr Ile
             20                  25                  30

Phe Val Leu Gln His Asn Ser Thr Val Gly Ala Arg Ile Arg Thr Ile
         35                  40                  45

Pro Thr Ser Asn Leu Ala Glu Cys Ser Asp His Cys Ala Ala Ser Leu
     50                  55                  60

Asp Cys Gln Gly Val Glu Phe Lys Asp Gly Ser Cys Ala Val Phe Arg
 65                  70                  75                  80

Ala Gly Ser Glu Lys Ala Thr Lys Gly Ser Gln Leu Leu Thr Lys Ser
                 85                  90                  95

Cys Val Lys Ser Asp Arg Val Cys Gln Ser Pro Phe Gln Phe Asp Leu
            100                 105                 110

Phe Glu Gln Lys Ile Leu Val Gly Phe Ala Arg Glu Val Val Pro Ala
        115                 120                 125

Glu Asn Ile Gln Val Cys Met Ala Ala Cys Leu Asn Ala Phe Asp Thr
    130                 135                 140

Phe Gly Phe Glu Cys Glu Ser Ala Met Phe Tyr Pro Val Asp Gln Glu
145                 150                 155                 160

Cys Ile Leu Asn Thr Glu Asp Arg Leu Asp Arg Pro Ser Leu Phe Val
                165                 170                 175

Asp Glu Ala Asp Asp Thr Val Ile Tyr Met Asp Asn Asn Cys Ala Gly
            180                 185                 190

Cys Lys Phe Gln Asn Pro Cys Ser His Val Asp Leu Tyr Phe Ser Leu
        195                 200                 205

Ala Gln Cys Tyr Pro Pro Tyr Ile Thr Gln Tyr Ile Ala Val Glu Gly
    210                 215                 220

Lys Gln Leu Lys Asn Glu Leu Asp Arg Ile Ile Asn Val Asp Leu Asp
225                 230                 235                 240

Ser Cys Gln Ala Leu Cys Thr Gln Arg Leu Ser Ile Ser Ser Asn Asp
                245                 250                 255

Phe Asn Cys Lys Ser Phe Met Tyr Asn Asn Lys Thr Arg Thr Cys Ile
            260                 265                 270

-continued

```
Leu Ala Asp Glu Arg Ser Lys Pro Leu Gly Arg Ala Asp Leu Val Ala
        275                 280                 285
Thr Glu Gly Phe Thr Tyr Phe Glu Lys Lys Cys Phe Ala Ser Pro Asn
    290                 295                 300
Thr Cys Arg Asn Val Pro Ser Phe Lys Arg Val Pro Gln Met Ile Leu
305                 310                 315                 320
Val Gly Phe Ala Ala Phe Val Met Glu Asn Val Pro Ser Val Thr Met
                325                 330                 335
Cys Leu Asp Gln Cys Thr Asn Pro Pro Glu Thr Gly Asp Gly Phe
            340                 345                 350
Val Cys Lys Ser Val Met Tyr Tyr Asn Glu Gln Glu Cys Ile Leu
        355                 360                 365
Asn Ser Glu Thr Arg Glu Ser Lys Pro Glu Leu Phe Ile Pro Glu Gly
    370                 375                 380
Glu Glu Phe Leu Val Asp Tyr Phe Asp Ile Thr Cys His Leu Lys Gln
385                 390                 395                 400
Glu Lys Cys Pro Ala Gly Gln His Leu Lys Ala Ile Arg Thr Ile Asn
                405                 410                 415
Ala Ala Leu Pro Glu Gly Glu Ser Glu Leu His Val Leu Lys Ser Ser
            420                 425                 430
Ala Ala Lys Gly Ile Lys Glu Cys Val Ala Lys Cys Phe Gly Leu Ala
        435                 440                 445
Pro Glu Lys Cys Arg Ser Phe Asn Tyr Asp Lys Lys Thr Lys Ser Cys
    450                 455                 460
Asp Leu Leu Tyr Leu Asp Gly His Asn Thr Leu Gln Pro Gln Val Arg
465                 470                 475                 480
Gln Gly Val Asp Leu Tyr Asp Leu His Cys Leu Ala Ala Leu Pro Leu
                485                 490                 495
Val Glu Asn Asp Cys Ser Ala Asn Lys Asp Ala Leu Phe Ser Arg
            500                 505                 510
Tyr Leu His Thr Lys Gln Arg Gly Ile Pro Ala Lys Ser Tyr Lys Val
        515                 520                 525
Val Ser Leu Asn Ser Cys Leu Glu Val Cys Ala Gly Asn Pro Thr Cys
    530                 535                 540
Ala Gly Ala Asn Tyr Asn Arg Arg Leu Gly Asp Cys Ser Leu Phe Asp
545                 550                 555                 560
Ala Ile Asp Lys Asp Ala Glu Val Asn Glu His Thr Asp Phe Tyr Lys
                565                 570                 575
Asn Leu Cys Val Thr Lys Glu Val Asp Thr Gly Ala Ser Ala Ala Ala
            580                 585                 590
Asn Val Pro Glu Thr Lys His Arg Val Ser Gly Thr Val Val Glu Gly
        595                 600                 605
Lys Asp Ser Lys Ala Gln Leu Leu Ala Thr Lys Val Lys Lys Pro
    610                 615                 620
Thr Ile Lys Asn Thr Glu His Arg Arg Ala Pro Glu Ser Thr Val Pro
625                 630                 635                 640
Leu Gly Pro Pro Val Glu Val Lys Ala Glu Ala Ile Gln Thr Ile Cys
                645                 650                 655
Asn Tyr Glu Gly Ile Lys Val Gln Ile Asn Asn Gly Glu Pro Phe Ser
            660                 665                 670
Gly Val Ile Phe Val Lys Asn Lys Phe Asp Thr Cys Arg Val Glu Val
        675                 680                 685
Ala Asn Ser Asn Ala Ala Thr Leu Val Leu Gly Leu Pro Lys Asp Phe
```

```
                690             695             700
Gly Met Arg Pro Ile Ser Leu Asp Asn Leu Asp Asp Asn Glu Thr Gly
705                 710                 715                 720

Lys Asn Lys Thr Lys Lys Gly Glu Glu Thr Pro Leu Lys Glu Ile
                725                 730                 735

Glu Glu Phe Arg Gln Lys Arg Gln Ala Ala Glu Phe Arg Asp Cys Gly
            740                 745                 750

Leu Val Asp Leu Leu Asn Gly Thr Tyr Lys Ser Thr Val Val Ile Gln
                755                 760                 765

Thr Asn Asn Leu Gly Ile Pro Gly Leu Val Thr Ser Met Asp Gln Leu
    770                 775                 780

Tyr Glu Val Ser Cys Asp Tyr Ser Ser Met Leu Gly Gly Arg Val Gln
785                 790                 795                 800

Ala Gly Tyr Asn Met Thr Val Thr Gly Pro Glu Ala Asn Leu Ile Gln
                805                 810                 815

Pro Arg Gly Lys Ile Glu Leu Gly Asn Pro Val Leu Met Gln Leu Leu
            820                 825                 830

Asn Gly Asp Gly Thr Glu Gln Pro Leu Val Gln Ala Lys Leu Gly Asp
                835                 840                 845

Ile Leu Glu Leu Arg Trp Glu Ile Met Ala Met Asp Asp Glu Leu Asp
850                 855                 860

Phe Val Lys Asn Cys His Ala Glu Pro Gly Leu Ala Gly Gly Lys
865                 870                 875                 880

Ala Gly Ala Gly Glu Lys Leu Gln Leu Ile Asp Gly Gly Cys Pro Thr
                885                 890                 895

Pro Ala Val Ala Gln Lys Leu Ile Pro Gly Ala Ile Glu Val Lys Ser
            900                 905                 910

Ser Ala Val Lys Thr Thr Lys Met Gln Ala Phe Arg Phe Asp Ser Ser
    915                 920                 925

Ala Ser Ile Arg Val Thr Cys Glu Val Glu Ile Cys Lys Gly Asp Cys
930                 935                 940

Glu Ala Val Glu Cys Ala Leu Thr Gly Gly Val Lys Lys Ser Phe Gly
945                 950                 955                 960

Arg Lys Lys Arg Glu Val Asn Asn Ile Glu Glu Phe Glu Thr Asn
                965                 970                 975

Arg Tyr Leu Ile Pro Arg Arg Ser His Ala Thr Thr Ser Ile Val Ile
            980                 985                 990

Ile Asp Pro Leu Gln Gln Val Asn Glu Pro Val Ala Met Ser Arg Ala
            995                 1000                1005

Ser Thr Leu Asp Leu Leu Arg Glu Glu Ala His Glu Val Gln Val Ile
    1010                1015                1020

Glu Glu Gly Ser Ile Cys Leu Asn Arg Ile Thr Val Phe Ala Ile Phe
1025                1030                1035                1040

Gly Thr Leu Ala Val Leu Ile Leu Gly Gln Val Ile Val Val Ala His
                1045                1050                1055

Tyr Ala Val Arg Arg Phe Ser Thr Glu Lys Thr Ala
                1060                1065
```

<210> SEQ ID NO 46
<211> LENGTH: 742
<212> TYPE: PRT
<213> ORGANISM: Caenorhabditis briggsae

<400> SEQUENCE: 46

-continued

```
Met Ser Pro Arg Val Ile Phe Leu Leu Leu Gly Ser Phe Leu Thr Ala
 1               5                  10                  15

Gln Ala Val Phe Glu Cys Ser Ser His Glu Thr Thr Ala Phe Val Arg
                 20                  25                  30

Ile Pro Arg Ala Arg Leu Asp Gly Thr Pro Val Val Ile Ser Thr Ala
             35                  40                  45

Gly His Asp Leu Thr Cys Ala Gln Tyr Cys Arg Asn Asn Ile Glu Pro
 50                  55                  60

Thr Thr Gly Ala Gln Arg Val Cys Ala Ser Phe Asn Phe Asp Gly Arg
 65                  70                  75                  80

Glu Thr Cys Tyr Phe Phe Asp Asp Ala Ala Thr Pro Ala Gly Thr Ser
                 85                  90                  95

Gln Leu Thr Ala Asn Pro Ser Ala Asn Asn Phe Tyr Tyr Glu Lys Thr
                100                 105                 110

Cys Ile Pro Asn Val Ser Ala His Glu Ala Cys Thr Tyr Arg Ser Phe
            115                 120                 125

Ser Phe Glu Arg Ala Arg Asn Thr Gln Leu Glu Gly Phe Val Lys Lys
        130                 135                 140

Ser Val Thr Val Lys Asn Arg Glu His Cys Leu Ser Ala Cys Leu Lys
145                 150                 155                 160

Glu Lys Glu Phe Val Cys Lys Ser Val Asn Phe His Tyr Glu Asn Ser
                165                 170                 175

Leu Cys Glu Leu Ser Val Glu Asp Lys Arg Ser Lys Pro Thr His Val
                180                 185                 190

Arg Met Ser Glu Gly Ile Asp Tyr Tyr Asp Asn Asn Cys Leu Ser Arg
            195                 200                 205

Gln Asn Arg Cys Gly Pro Ser Gly Gly Asn Leu Val Phe Val Lys Thr
        210                 215                 220

Thr Asn Phe Glu Ile Arg Tyr Tyr Asp His Thr Gln Ser Val Glu Ala
225                 230                 235                 240

Gln Glu Ser Tyr Cys Leu Gln Lys Cys Leu Asp Ser Leu Asn Thr Phe
                245                 250                 255

Cys Arg Ser Val Glu Phe Asn Pro Lys Glu Lys Asn Cys Ile Val Ser
                260                 265                 270

Asp Glu Asp Thr Phe Ser Arg Ala Asp Gln Gln Gly Gln Val Val Gly
            275                 280                 285

Lys Asp Tyr Tyr Glu Pro Ile Cys Val Ala Ala Asp Leu Ser Ser Ser
        290                 295                 300

Thr Cys Arg Gln Gln Ala Ala Phe Glu Arg Phe Ile Gly Ser Ser Ile
305                 310                 315                 320

Glu Gly Glu Val Val Ala Ser Ala Gln Gly Val Thr Ile Ser Asp Cys
                325                 330                 335

Ile Ser Leu Cys Phe Gln Asn Leu Asn Cys Lys Ser Ile Asn Tyr Asp
            340                 345                 350

Arg Thr Ala Ser Ser Cys Phe Ile Tyr Ala Val Gly Arg Gln Asp Ala
        355                 360                 365

Asn Ile Lys Ala Asn Pro Ser Met Asp Tyr Tyr Glu Phe Asn Cys Glu
        370                 375                 380

Ser Gln Phe Gly Gly Met Ala Leu Cys Thr Asn Glu Gly Ile Arg Phe
385                 390                 395                 400

Ile Val Asn Thr Lys Glu Pro Tyr Thr Gly Ala Ile Tyr Ala Ala Glu
            405                 410                 415

Arg Phe Ser Thr Cys Ser Gln Val Val Glu Asn Ala Lys Gln Ile Ser
```

```
            420             425             430
Ile Thr Phe Pro Pro Thr Val Thr Ser Asp Cys Gly Thr Val Ile
        435                 440                 445
Arg Asp Gly Lys Met Glu Ala Leu Val Val Ser Leu Asp Gly Val
        450                 455                 460
Leu Pro His Gln Val Thr Thr Glu Trp Asp Arg Phe Tyr Arg Val Ser
465                 470                 475                 480
Cys Asp Val Ser Met Asp Lys Met Val Lys Glu Gly Ser Val Val Val
                485                 490                 495
Thr Thr Ile Tyr Glu Ala Ser Ser Gln Asn Thr Thr Val Leu Asp Val
                500                 505                 510
Ala Thr Pro Pro Val Thr Ala Glu Leu Gln Ile Leu Asn Gln Leu
        515                 520                 525
Glu Glu Pro Leu His Lys Ala Ser Ile Gly Asp Pro Leu Leu Val
        530                 535                 540
Ile Thr Ser Glu Gln Ala Gly Pro His Asn Met Met Val Thr Glu Cys
545                 550                 555                 560
Thr Ala Thr Arg Val Gly Gly Phe Gly Asp Thr Val Pro Phe Thr Leu
                565                 570                 575
Ile Glu Asn Gly Cys Pro Arg Tyr Pro Ala Leu Val Gly Pro Val Glu
                580                 585                 590
Gln Asp Phe Asp Lys Asn Arg Leu Lys Ser Asp Leu Arg Ala Phe Arg
        595                 600                 605
Leu Asp Gly Ser Tyr Asp Val Gln Ile Val Cys Ser Ile Met Phe Cys
        610                 615                 620
Ala Gly Pro Asn Gly Cys Pro Val Ser Asn Cys Leu Asp Ser Gly Thr
625                 630                 635                 640
Asn Glu Leu Phe Met Ser His Gly Arg Lys Lys Arg Ser Val Asp Leu
                645                 650                 655
Glu Ala Gly Glu Thr Glu Arg Leu Ser Ala Ile Ile Arg Val Phe
        660                 665                 670
Ala Lys Gly Glu Asp Glu Glu Ile Glu Met Gly Asn Asn Thr Leu
        675                 680                 685
Met Thr Ser Leu Ala Glu Ser Thr Asp Leu Leu Cys Ile Ala Glu Pro
690                 695                 700
Phe Phe Val Ser Ser Val Val Ser Leu Ser Val Leu Cys Phe Ala Leu
705                 710                 715                 720
Ser Ala Ile Ile Ala Ile Trp Gly Cys His Ala Leu His Ala Lys Pro
                725                 730                 735
Thr Lys Gln Val Ala Ala
            740

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
gtaatacgac tcactatagg gc                                              22

<210> SEQ ID NO 48
<211> LENGTH: 20
<212> TYPE: DNA
<213> ORGANISM: Artificial Sequence
```

```
<220> FEATURE:
<223> OTHER INFORMATION: Primer

<400> SEQUENCE: 48
aattaaccct cactaaaggg                                              20

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
gatttaggtg acactatag                                               19

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
ggccacgcgt cgactagtac ggggggggg                                    29

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tcagtgacgt tatgtcctcc                                              20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgacagatgg aacattctcc                                              20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
acttcaggac acgacttgac                                              20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
caatcagaga tggtaactcc                                              20
```